US012678498B2

(12) United States Patent
Karkera et al.

(10) Patent No.: US 12,678,498 B2
(45) Date of Patent: Jul. 14, 2026

(54) FGFR/PD-1 COMBINATION THERAPY FOR THE TREATMENT OF CANCER

(71) Applicant: ASTEX THERAPEUTICS LTD, Cambridge (GB)

(72) Inventors: Jayaprakash Karkera, Germantown, MD (US); Suso Jesus Platero, Washington Crossing, PA (US); Raluca Verona, Swarthmore, PA (US); Matthew V. Lorenzi, Philadelphia, PA (US)

(73) Assignee: ASTEX THERAPEUTICS LTD, Cambridge (GB)

( * ) Notice: Subject to any disclaimer, the term of this patent is extended or adjusted under 35 U.S.C. 154(b) by 81 days.

(21) Appl. No.: 17/655,519

(22) Filed: Mar. 18, 2022

(65) Prior Publication Data

US 2023/0030983 A1     Feb. 2, 2023

Related U.S. Application Data

(63) Continuation of application No. 16/661,671, filed on Oct. 23, 2019, now abandoned, which is a continuation of application No. 15/079,136, filed on Mar. 24, 2016, now Pat. No. 10,478,494.

(60) Provisional application No. 62/142,569, filed on Apr. 3, 2015.

(51) Int. Cl.
| | |
|---|---|
| *A61K 39/395* | (2006.01) |
| *A61K 31/498* | (2006.01) |
| *A61K 45/06* | (2006.01) |
| *C07K 16/28* | (2006.01) |
| *C12Q 1/6886* | (2018.01) |
| *G01N 33/574* | (2006.01) |

(52) U.S. Cl.
CPC ........ *A61K 39/3955* (2013.01); *A61K 31/498* (2013.01); *A61K 45/06* (2013.01); *C07K 16/2818* (2013.01); *C12Q 1/6886* (2013.01); *G01N 33/57492* (2013.01); *C12Q 2600/158* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | |
|---|---|---|
| 2,940,972 A | 6/1960 | Roch |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,457,105 A | 10/1995 | Barker |
| 5,700,823 A | 12/1997 | Hirth et al. |
| 5,710,158 A | 1/1998 | Myers et al. |
| 5,733,913 A | 3/1998 | Blankley et al. |
| 5,882,864 A | 3/1999 | An et al. |
| 6,060,498 A | 5/2000 | Ashizawa et al. |
| 6,218,529 B1 | 4/2001 | An et al. |
| 6,271,231 B1 | 8/2001 | Bergstrand et al. |
| 6,331,555 B1 | 12/2001 | Hirth et al. |
| 7,135,311 B1 | 11/2006 | David et al. |
| 7,432,279 B2 | 10/2008 | Green et al. |
| 8,409,577 B2 | 4/2013 | Thompson et al. |
| 8,628,796 B2 | 1/2014 | Kottayil et al. |
| 8,895,601 B2 | 11/2014 | Saxty et al. |
| 9,067,998 B1 | 6/2015 | Clube |
| 9,145,367 B2 | 9/2015 | Tazi et al. |
| 9,221,804 B2 | 12/2015 | Leonard et al. |
| 9,290,478 B2 | 3/2016 | Saxty et al. |
| 9,303,029 B2 | 4/2016 | Woodhead et al. |
| 9,303,030 B2 | 4/2016 | Angibaud et al. |
| 9,309,241 B2 | 4/2016 | Angibaud et al. |
| 9,309,242 B2 | 4/2016 | Berdini et al. |
| 9,399,028 B2 | 7/2016 | Tavazoie et al. |
| 9,439,896 B2 | 9/2016 | Berdini et al. |
| 9,447,098 B2 | 9/2016 | Saxty et al. |
| 9,464,071 B2 | 10/2016 | Saxty et al. |
| 9,493,426 B2 | 11/2016 | Angibaud et al. |
| 9,527,844 B2 | 12/2016 | Angibaud et al. |
| 9,737,544 B2 | 8/2017 | Angibaud et al. |

(Continued)

FOREIGN PATENT DOCUMENTS

| | | |
|---|---|---|
| CA | 2502825 A1 | 5/2004 |
| CA | 2524525 | 12/2004 |

(Continued)

OTHER PUBLICATIONS

Nozomu Fuse et al., The development of c-Met inhibitor, treatment of cancer molecule targets, vol. 7, No. 2, pp. 111 to 116 (2009). Interface on Cancer Therapy.

International Search Report for PCT/US2016/025482 dated Aug. 5, 2016.

Moreira Da Silva, R., "Novolumab: Anti-PD-1 monoclonal antibody cancer immunotherapy", *Drugs of the Future*, vol. 39, No. 1, pp. 15-24 (2014).

Ho, H.K., et al., "Current strategies for inhibiting FGFR activities in clinical applications: opportunities, challenges and toxicological considerations", *Drug Discovery Today*, vol. 19, Issue 1, Abstract only (2014).

(Continued)

*Primary Examiner* — Peter J Reddig
(74) *Attorney, Agent, or Firm* — HESLIN ROTHENBERG FARLEY & MESITI P.C.

(57) ABSTRACT

Provided herein are combination therapies for the treatment of cancer. In particular, the disclosed methods are directed to treatment of cancer in a patient comprising administering an antibody that blocks the interaction between PD-1 and PD-L1 and an FGFR inhibitor, wherein the antibody that blocks the interaction between PD-1 and PD-L1 and the FGFR inhibitor are administered if one or more FGFR variants are present in a biological sample from the patient.

36 Claims, 5 Drawing Sheets

Specification includes a Sequence Listing.

(56) References Cited

U.S. PATENT DOCUMENTS

| | | | |
|---|---|---|---|
| 9,757,364 B2 | 9/2017 | Angibaud et al. |
| 9,850,228 B2 | 12/2017 | Saxty et al. |
| 9,856,236 B2 | 1/2018 | Saxty et al. |
| 9,902,714 B2 | 2/2018 | Vermeulen |
| 10,039,759 B2 | 8/2018 | Berdini et al. |
| 10,045,982 B2 | 8/2018 | Berdini et al. |
| 10,052,320 B2 | 8/2018 | Woodhead et al. |
| 10,085,982 B2 | 10/2018 | Jovcheva et al. |
| 10,272,087 B2 | 4/2019 | Saxty et al. |
| 10,421,747 B2 | 9/2019 | Vermeulen et al. |
| 10,478,494 B2 | 11/2019 | Karkera et al. |
| 10,519,137 B2 | 12/2019 | Saxty et al. |
| 10,716,787 B2 | 7/2020 | Jovcheva et al. |
| 10,736,900 B2 | 8/2020 | Jovcheva et al. |
| 10,898,482 B2 | 1/2021 | Broggini |
| 2003/0207886 A1 | 11/2003 | Plücker et al. |
| 2003/0229067 A1 | 12/2003 | Castelhano et al. |
| 2003/0235628 A1 | 12/2003 | Taneja et al. |
| 2004/0204450 A1 | 10/2004 | Bechle et al. |
| 2005/0261307 A1 | 11/2005 | Cai et al. |
| 2005/0272727 A1 | 12/2005 | Dong et al. |
| 2005/0272728 A1 | 12/2005 | Altenbach et al. |
| 2005/0272736 A1 | 12/2005 | Altenbach et al. |
| 2006/0188568 A1 | 8/2006 | Bhamare et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0117097 A1 | 5/2009 | Igawa et al. |
| 2009/0118261 A1 | 5/2009 | Aquila et al. |
| 2009/0162352 A1 | 6/2009 | Adler et al. |
| 2009/0208575 A1 | 8/2009 | Gunupati et al. |
| 2009/0221591 A1 | 9/2009 | Hartmann et al. |
| 2009/0263397 A1 | 10/2009 | Buck et al. |
| 2010/0228026 A1 | 9/2010 | Yoshida et al. |
| 2010/0234347 A1 | 9/2010 | Dollinger et al. |
| 2011/0123545 A1 | 5/2011 | Marsh et al. |
| 2012/0172427 A1 | 7/2012 | Hauck |
| 2012/0302572 A1 | 11/2012 | Kan et al. |
| 2013/0072457 A1* | 3/2013 | Saxty ............... C07D 409/14 |
| | | 514/249 |
| 2013/0096021 A1 | 4/2013 | Chinnaiyan et al. |
| 2013/0267525 A1 | 10/2013 | Saxty et al. |
| 2013/0296326 A1 | 11/2013 | Pollock |
| 2014/0037642 A1 | 2/2014 | McCaffery et al. |
| 2014/0128430 A1 | 5/2014 | Frenkel et al. |
| 2014/0288053 A1 | 9/2014 | Berdini et al. |
| 2014/0296236 A1 | 10/2014 | Berdini et al. |
| 2015/0017637 A1 | 1/2015 | Chinnaiyan et al. |
| 2015/0031669 A1 | 1/2015 | Woodhead et al. |
| 2015/0031703 A1* | 1/2015 | Suzuki ............... A61P 35/00 |
| | | 435/6.12 |
| 2015/0057293 A1 | 2/2015 | Angibaud et al. |
| 2015/0086584 A1 | 3/2015 | Gilboa et al. |
| 2015/0105368 A1 | 4/2015 | Saxty et al. |
| 2015/0183875 A1 | 7/2015 | Cobbold et al. |
| 2015/0191791 A1 | 7/2015 | Shibata |
| 2015/0203589 A1* | 7/2015 | Iavarone ............... C07K 14/47 |
| | | 435/6.12 |
| 2015/0210769 A1* | 7/2015 | Freeman ............... A61P 1/04 |
| | | 435/254.2 |
| 2015/0239883 A1 | 8/2015 | Angibaud et al. |
| 2015/0291589 A1 | 10/2015 | Saxty et al. |
| 2015/0307945 A1 | 10/2015 | Nakanishi et al. |
| 2016/0031856 A1 | 2/2016 | Saxty et al. |
| 2016/0031990 A1 | 2/2016 | Steele et al. |
| 2016/0067336 A1 | 3/2016 | Fandi et al. |
| 2016/0075666 A1 | 3/2016 | Angibaud et al. |
| 2016/0090633 A1* | 3/2016 | Platero ............... C12Q 1/6886 |
| | | 536/24.31 |
| 2016/0108034 A1 | 4/2016 | Angibaud et al. |
| 2016/0122410 A1 | 5/2016 | Behrens et al. |
| 2016/0213677 A1 | 7/2016 | Angibaud et al. |
| 2016/0220564 A1 | 8/2016 | Woodhead et al. |
| 2016/0235744 A1 | 8/2016 | Berdini et al. |
| 2016/0243228 A1 | 8/2016 | Holash et al. |
| 2016/0287699 A1 | 10/2016 | Karkera et al. |
| 2016/0311800 A1 | 10/2016 | Saxty et al. |
| 2016/0347836 A1 | 12/2016 | Grosso |
| 2017/0000781 A1 | 1/2017 | Berdini et al. |
| 2017/0000796 A1 | 1/2017 | Saxty et al. |
| 2017/0021019 A1 | 1/2017 | Zibelman et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |
| 2017/0145102 A1 | 5/2017 | Pierce et al. |
| 2017/0145103 A1 | 5/2017 | Pierce et al. |
| 2018/0021332 A1 | 1/2018 | Broggini |
| 2018/0127397 A1 | 5/2018 | Saxty et al. |
| 2018/0186775 A1 | 7/2018 | Vermeulen et al. |
| 2018/0296558 A1 | 10/2018 | Jovcheva et al. |
| 2020/0108141 A1 | 4/2020 | Karkera et al. |
| 2020/0131153 A1 | 4/2020 | Saxty et al. |
| 2021/0038598 A1 | 2/2021 | Jovcheva et al. |
| 2021/0169877 A1 | 6/2021 | Broggini |
| 2022/0135544 A1 | 5/2022 | Saxty et al. |

FOREIGN PATENT DOCUMENTS

| | | |
|---|---|---|
| CA | 2524948 | 12/2004 |
| CN | 1128496 A | 8/1996 |
| CN | 1966500 A | 5/2007 |
| CN | 102036963 A | 4/2011 |
| CN | 105030777 A | 11/2015 |
| CN | 105147687 A | 12/2015 |
| EP | 0544445 A2 | 6/1993 |
| EP | 1001946 | 5/2000 |
| EP | 1659175 A1 | 5/2006 |
| EP | 1208231 B1 | 1/2007 |
| EP | 1964837 A1 | 9/2008 |
| EP | 1990342 | 11/2008 |
| EP | 2332939 | 6/2011 |
| EP | 2650293 A1 | 10/2013 |
| EP | 3027210 A1 | 6/2016 |
| EP | 3177321 A1 | 6/2017 |
| EP | 3179992 A1 | 6/2017 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 9909845 A1 | 3/1999 |
| WO | 99/17759 A2 | 4/1999 |
| WO | 99/42463 A1 | 8/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 03/086394 A1 | 10/2003 |
| WO | 2004/006355 A2 | 1/2004 |
| WO | 2004/011465 A1 | 2/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |

(56) References Cited

FOREIGN PATENT DOCUMENTS

| | | | |
|---|---|---|---|
| WO | 2006040568 A1 | 4/2006 |
| WO | 2006/066361 A1 | 6/2006 |
| WO | 2006084338 A1 | 8/2006 |
| WO | 2006/092430 A1 | 9/2006 |
| WO | 2006/120456 A1 | 11/2006 |
| WO | 2006121168 A1 | 11/2006 |
| WO | 2006124354 A2 | 11/2006 |
| WO | 2007/003419 A1 | 1/2007 |
| WO | 2007005874 A2 | 1/2007 |
| WO | 2007/023186 A1 | 3/2007 |
| WO | 2007/044729 A2 | 4/2007 |
| WO | 2007054556 A1 | 5/2007 |
| WO | 2007/075567 A1 | 7/2007 |
| WO | 2007/117607 A2 | 10/2007 |
| WO | 2007/125405 A2 | 11/2007 |
| WO | 2007/132227 A1 | 11/2007 |
| WO | 2007140222 A2 | 12/2007 |
| WO | 2008/003702 A2 | 1/2008 |
| WO | 2008/021389 A2 | 2/2008 |
| WO | 2008060907 A2 | 5/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008109465 A2 | 9/2008 |
| WO | 2008112408 A1 | 9/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009020990 A1 | 2/2009 |
| WO | 2009/064835 A1 | 5/2009 |
| WO | 2009/114335 A2 | 9/2009 |
| WO | 2009/137378 A1 | 11/2009 |
| WO | 2009/141386 A1 | 11/2009 |
| WO | 2010/056872 A2 | 5/2010 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2010/138661 A1 | 12/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012106556 A2 | 8/2012 |
| WO | 2012/118492 A1 | 9/2012 |
| WO | 2012/148540 A1 | 11/2012 |
| WO | 2013019906 A1 | 2/2013 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013076186 A1 | 5/2013 |
| WO | 2013087725 A1 | 6/2013 |
| WO | 2013089882 A2 | 6/2013 |
| WO | 2013133351 A1 | 9/2013 |
| WO | 2013/151913 A1 | 10/2013 |
| WO | 2013173485 A1 | 11/2013 |
| WO | 2013/179033 A1 | 12/2013 |
| WO | 2013/179034 A1 | 12/2013 |
| WO | 2014/011672 A1 | 1/2014 |
| WO | 2014007369 A1 | 1/2014 |
| WO | 2014018673 A2 | 1/2014 |
| WO | 2014018841 A1 | 1/2014 |
| WO | 2014051022 A1 | 4/2014 |
| WO | 2014071419 A2 | 5/2014 |
| WO | 2014113729 A2 | 7/2014 |
| WO | 2014/165422 A1 | 10/2014 |
| WO | 2014/174307 A1 | 10/2014 |
| WO | 2014165710 A2 | 10/2014 |
| WO | 2014/198337 A1 | 12/2014 |
| WO | 2014/201111 A1 | 12/2014 |
| WO | 2014193229 A2 | 12/2014 |
| WO | 2015/016718 A1 | 2/2015 |
| WO | 2015017607 A2 | 2/2015 |
| WO | 2015/077717 A1 | 5/2015 |
| WO | 2015/100257 A1 | 7/2015 |
| WO | 2015/112900 A1 | 7/2015 |
| WO | 2015144803 A1 | 10/2015 |
| WO | 2015144804 A1 | 10/2015 |
| WO | 2015144808 A1 | 10/2015 |
| WO | 2016/004218 A1 | 1/2016 |
| WO | 2016/004875 A1 | 1/2016 |
| WO | 2016/019472 A1 | 2/2016 |
| WO | 2016/024228 A1 | 2/2016 |
| WO | 2016/024231 A1 | 2/2016 |
| WO | 2016/040880 A1 | 3/2016 |
| WO | 2016/040882 A1 | 3/2016 |
| WO | 2016/044207 A1 | 3/2016 |
| WO | 2016048833 A2 | 3/2016 |
| WO | 2016/054555 A2 | 4/2016 |
| WO | 2016/061142 A1 | 4/2016 |
| WO | 2016/065409 A1 | 5/2016 |
| WO | 2016/094309 A1 | 6/2016 |
| WO | 2016/100882 A1 | 6/2016 |
| WO | 2016/118654 A1 | 7/2016 |
| WO | 2016/128912 A1 | 8/2016 |
| WO | 2016128411 A1 | 8/2016 |
| WO | 2016134234 A1 | 8/2016 |
| WO | 2016/137850 A1 | 9/2016 |
| WO | 2016/140717 A1 | 9/2016 |
| WO | 2016/141209 A1 | 9/2016 |
| WO | 2016/141218 A1 | 9/2016 |
| WO | 2016/153839 A1 | 9/2016 |
| WO | 2016/154068 A1 | 9/2016 |
| WO | 2016/154473 A1 | 9/2016 |
| WO | 2016/161239 A1 | 10/2016 |
| WO | 2016/168716 A1 | 10/2016 |
| WO | 2016/191751 A1 | 12/2016 |
| WO | 2016/196389 A1 | 12/2016 |
| WO | 2016/201425 A1 | 12/2016 |
| WO | 2016/210108 A1 | 12/2016 |
| WO | 2017/004192 A1 | 1/2017 |
| WO | 2017/013436 A1 | 1/2017 |
| WO | 2017/046746 A1 | 3/2017 |
| WO | 2017/091577 A1 | 6/2017 |
| WO | 2017/091580 A1 | 6/2017 |
| WO | 2017/093942 A1 | 6/2017 |
| WO | 2018/220206 A1 | 12/2018 |

OTHER PUBLICATIONS

Yan, L., et al., "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.

Thompson, A.M., et al. "Synthesis and Structure—Activity Relationships of 7-Substituted 3-(2,6-Dichlorophenyl)-1,6-napthyridin-2(1H)-ones as Selective Inhibitors of $pp60^{c\text{-}src}$", *Journal of Medicinal Chemistry*, vol. 43, No. 16, 2000, pp. 3134-3147.

Berge, S.M., et al. "Pharmaceutical Salts", *Journal of Pharmaceutical Sciences*, vol. 66, No. 1, 1977, pp. 1-19.

Deady, L.W. "Ring Nitrogen Oxidation of Amino Substituted Nitrogen Heterocycles with m-Chloroperbenzoic Acid", *Synthetic Communications*, vol. 7(8), 1977, pp. 509-514.

(56) References Cited

OTHER PUBLICATIONS

Knights, V., et al. "De-regulated FGF receptors as therapeutic targets in cancer", *Pharmacology & Therapeutics*, 2010; vol. 125(1), pp. 105-117.

Korc, M., et al. "The Role of Fibroblast Growth Factors in Tumor Growth", *Current Cancer Drug Targets*, vol. 9(5), 2009, pp. 639-651.

Angerer, L.M., et al. "Demonstration of Tissue-Specific Gene Expression by in Situ Hybridization", *Methods in Enzymology*, vol. 152, 1987, pp. 649-661.

Deprimo, S.E., et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, M., et al., "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

Zhou, W., et al., "A Structure-Guided Approach to Creating Covalent FGFR Inhibitors", *Chemistry & Biology*, vol. 17, pp. 285-295 (2010).

Avendaño, C., et al., "Drugs That Inhibit Signalling Pathways for Tumor Cell Growth and Proliferation", *Medicinal Chemistry of Anticancer Drugs*, pp. 251-305 (2008).

Garuti, L., et al., Irreversible Protein Kinase Inhibitors, *Current Medicinal Chemistry*, vol. 18, No. 20, Jul. 1, 2011, pp. 2981-2994.

Vippagunta, S.R. et al., "Crystalline Solids", *Advanced Drug Delivery Reviews*, vol. 48, pp. 3-26 (2001).

Jordan, V.C., "Tamoxifen: A Most Unlikely Pioneering Medicine", *Nature Reviews: Drug Discovery*, vol. 2, pp. 205-213 (2003).

Hackam, D.G., et al., "Translation of Research Evidence From Animals to Humans", *JAMA*, vol. 14, pp. 1731-1732 (2006).

"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).

V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).

"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).

Dorwald, F.Z., "Side Reactions in Organic Synthesis: A Guide to Successful Synthesis Design", Weinheim: WILEY-VCH Verlag GmbH & Co. KGaA, 2005, ISBN: 3-527-31021.5.

Lima, L.M., et al., "Bioisosterism: A Useful Strategy for Molecular Modification and Drug Design", *Current Medical Chemistry*, vol. 12(1), pp. 23-49 (2005).

Patani, G.A., et al., "Bioisosterism: A Rational Approach in Drug Design", *Chem. Rev.* vol. 96, pp. 3147-3176 (1996).

Dieci, M.V., et al., "Fibroblast Growth Factor Receptor Inhibitors as a Cancer Treatment: From a Biologic Rationale to Medical Perspectives", *Cancer Discovery*, vol. 3, No. 3, pp. 264-279 (Feb. 2013).

Gallick, G.E., et al., "Small-molecule protein tyrosine kinase inhibitors for the treatment of metastatic prostate cancer", *Future Medicinal Chemistry*, vol. 4, No. 1, pp. 107-119 (Jan. 2012).

Study to Assess the Relative Bioavailability of Orally Administered JNJ-42756493 Tablet Versus JNJ-42756493 Capsule in Healthy Participants, ClinicalTrials.gov, pp. 1-4 (2014).

Matsuda, Y., et al., "Fibroblast Growth Factor Receptor-2 IIIc as a Novel Molecular Target in Colorectal Cancer", *Current Colorectal Cancer Reports*, vol. 10, No. 1, pp. 20-26 (2014).

Carneiro, B.A., et al., "Emerging therapeutic targets in bladder cancer", *Cancer Treatment Reviews*, vol. 41, No. 2, pp. 170-178 (2015).

Fujita, M., et al., "Generation of Formaldehyde by Pharmaceutical Excipients and Its Absorption by Meglumine", *Chem. Pharm. Bull*, vol. 57, No. 10, pp. 1096-1099 (2009).

Adcock, J., et al., "Diversity oriented synthesis: substitution at C5 in unreactive pyrimidines by Claisen rearrangement and reactivity in nucleophilic substitution at C2 and C4 in pteridines and pyrido [2,3 -d]pyrimidines", *Tetrahedron*, vol. 67, pp. 3226-3237 (2011).

Database Caplus, Grina, et al., "Preparation of oxohydroquinazolinylaminophenylpropanesulfonamide derivatives and analogs for use as Raf inhibitors", Document No. 157:465574, Accession No. 2012:1301209 (2012).

Liang, G., et al., "Small molecule inhibition of fibroblast growth factor receptors in cancer", *Cytokine & Growth Factor Reviews*, vol. 24, pp. 467-475 (2013).

Golub, T.R., et al., "Molecular Classification of Cancer: Class Discovery and Class Prediction by Gene Expression Monitoring", *Science*, vol. 286, pp. 531-537 (1999).

Greulich, H., et al., "Targeting mutant fibroblast growth factor receptors in cancer", *Trends in Molecular Medicine*, vol. 17, No. 5, pp. 283-292 (2011).

Freshney, R.I., "Culture of Animal Cells, a Manual of Basic Technique", Published by Alan R. Liss, Inc, New York, pp. 1-6 (1983).

Cohen, P., "The development and therapeutic potential of protein kinase inhibitors", *Current Opinion in Chemical Biology*, vol. 3, pp. 459-465 (1999).

Cecil Textbook of Medicine, edited by Bennet, J.C., and Plum, F., 20th edition, vol. 1, pp. 1004-1010 (1996).

Hynes, N.E., et al., "Potential for Targeting the Fibroblast Growth Factor Receptors in Breast Cancer", *Cancer Research*, vol. 70, pp. 5199-5202 (2010).

Neidle, S., "Cancer Drug Design and Discovery", Elsevier/Academic Press, pp. 427-431 (2008).

Dermer, G.B., "Another Anniversary for the War on Cancer", *Biotechnology*, vol. 12, p. 320 (1994).

Katoh, Y., et al., "FGFR2-related pathogenesis and FGFR2-targeted therapeutics (Review)", *International Journal of Molecular Medicine*, vol. 23, pp. 307-311 (2009).

Jain, V.K., et al., "Challenges and opportunities in the targeting of fibroblast growth factor receptors in breast cancer", *Breast Cancer Research*, vol. 14, No. 208, pp. 1-9 (2012).

Sonpavde, G., et al., "Fibroblast growth factor receptors as therapeutic targets in clear-cell renal cell carcinoma", *Expert Opinion on Investigational Drugs*, vol. 23, Issue 3, pp. 305-315 (2014).

Rodriguez-Vida, A., et al., "Complexity of FGFR signaling in metastatic urothelial cancer," *Journal of Hematology & Oncology*, vol. 8, No., pp. 119 et seq. (2015).

Bronte et al., "Nintedanib in NSCLC: Evidence to Date and Place in Therapy," Therapeutic Advances in Medical Oncology, 2016, vol. 8[3], pp. 188-197.

Kathoh et al., "FGFR inhibitors: Effects on Cancer Cells, Tumor Microenvironment and Whole-Body Homeostasis (Review)," International Journal of Molecular Medicine 2016, 38(1), pp. 3-15.

D.A.Kharkevich, Farmakologiya (Pharmacology), 1996, M., Meditsina, p. 41, chapter 6.A (in Russian Only).

V.G.Belikov, Farmatsevticheskaya khimiya (Pharmaceutical Chemistry), M., Vysshaya shkola, 1993, p. 1, chapter 2.2, pp. 43-47) (in Russian only).

Amin et al., "Nivolumab (anti-PD-1; BMS-936558, ONO-4538) in combination with sunitinib or pazopanib in patients (pts) with metastatic renal cell carcinoma (mRCC)," Journal of Clinical Oncology 2014, vol. 32:15.

Phillips et al., "Therapeutic Uses of Anti-PD-1 and anti-PD-L1 Antibodies," International Immunology, Oct. 2014, vol. 27, No. 1, pp. 39-46.

Dienstmann et al., "Genomic Aberrations in the FGFR Pathway: Opportunities for Targeted Therapies in Solid Tumors," Annals of Oncology, vol. 25, Nov. 20, 2013, No. 3, pp. 552-563.

Parker et al., "Emergence of FGFR Family Gene Fusions as Therapeutic Targets in a Wide Spectrum of Solid Tumours," Journal of Pathology, Oct. 29, 2013, vol. 232, No. 1, pp. 4-15.

(56) References Cited

OTHER PUBLICATIONS

Arai et al., "Fibroblast Growth Factor Receptor 2 Tyrosine Kinase Fusions Define a Unique Molecular Subtype of Cholangiocarcinoma," Hepatology, Apr. 2014, vol. 59, No. 4, pp. 1427-1434.

Bahleda et al., "Phase 1 Study of JNJ-42756493, a Pan-Fibroblast Growth Factor Receptor (FGFR) Inhibitor, in Patients with Advanced Solid Tumors," Journal of Clinical Oncology, May 2014, vol. 32, No. 15, pp. 2501-2501.

Di Stefano et al., "Detection, Characterization, and Inhibition of FGFR-TACC Fusions in IDH Wild-Type Glioma," Clinical Cancer Research, Jan. 21, 2015, vol. 21, No. 14, pp. 3307-3317.

Angibaud et al., "Discovery of JNJ-42756493, A Potent Fibroblast Growth Factor Receptor (FGFR) Inhibitor Using a Fragment Based Approach," AACR Minisymposium, Small Molecule Design and Optimization San Diego, CA, Apr. 8, 2014, 16 pp.

Parker, B.C., et al., "The tumorigenic FGFR3-TACC3 gene fusion escapes miR-99a regulation in glioblastoma," The Journal of Clinical Investigation, 123 (2), pp. 855-865, Feb. 1, 2013.

Bello, et al., "E=3810 is a Potent Dual Inhibitor of VEGFR and FGFR that Exerts Antitumor Activity in Multiple Preclinical Models," vol. 71(4), pp. 1396-1405 (2011).

Database, Geneseq [Online], "FGFR3-TACC3 gene fusion PCR primer, FGFR3-TACC3(F18T11)_qPCR_F SEQ: 15," XP002753027, Database accession No. BAT14432 (2013).

Database, Geneseq [Online], "Human FGFR 2 mRNA target sequence for mdRNA, SEQ ID:3954," XP055257043, Database accession No. ATM46802 (2008).

Gavine, et al., "AZD4547: An Orally Bioavailable, Potent, and Selective Inhibitor of the Fibroblast Growth Factor Receptor Tyrosine Kinase Family," Cancer Research, vol. 72(8), pp. 2045-2056 (2012).

International Search Report from PCT/US2015/050996 dated Mar. 23, 2016.

Mengual, et al., BMC Research Notes 1:21, pp. 1-8 (Jun. 2008).

Millholland, et al., Research and Reports in Urology, 4: 33-40 (2012).

Sabnis, et al., "FGFR Fusions in the Driver's Seat," Cancer Discovery, vol. 3 (6), pp. 607-609 (2013).

Shinmura, et al., "A novel somatic FGFR3 mutation in primary lung cancer," Oncology Reports, vol. 31 (3), pp. 1219-1224 (2014).

Singh, et al., "Transforming Fusions of FGFR and TACC Genes in Human Glioblastoma," Science, vol. 337 (6099), pp. 1231-1235 (2012).

Trudel, et al., "Evaluation of XL999, a Potent Inhibitor of FGFR3, for the Potential Treatment of t(4;14) Positive Multiple Myeloma," Blood, vol. 110 (11), pp. 741A-742A (2007).

Williams, et al., "Oncogenic FGFR3 gene fusions in bladder cancer," Human Molecular Genetics, vol. 22 (4), pp. 795-803 (2013).

Wu, et al., "Identification of Targetable FGFR Gene Fusions in Diverse Cancers," Cancer Discovery, vol. 3 (6), pp. 636-647 (2013).

Fujita, Megumi et al., "Stabilization by Meglumine of an Amine Compound Degraded by Formaldehyde in Tablets." International Journal of Pharmaceutics 386.1-2 (2010): 195-200.

Singleton, KR et al., "A Receptor Tyrosine Kinase Network Composed of Fibroblast Growth Factor Receptors, Epidermal Growth Factor Receptor, v-erb-b2 Erythroblastic Leukemia Viral Oncogene Homolog 2, and Hepatocyte Growth Factor Receptor Drives Growth and Survival of Head and Neck Squamous Carcinoma Cell Lines", Molecular Pharmacology, Apr. 2013, vol. 83, No. 4, pp. 882-893.

Topalian et al., "Safety, Activity, and Immune Correlates of Anti-PD-1 Antibody in Cancer," The New England Journal of Medicine, Mar. 2, 2012, pp. 2443-2454.

André, Fabrice et al., "Rationale for targeting fibroblast growth factor receptor signaling in breast cancer," Breast Cancer Research and Treatment, vol. 150 No. 1, 2015, pp. 1-8.

Paola Corona et al., "Synthesis of N-(5,7-diamino-3-phenylquinoxalin-2-y1)-3,4,5-substituted anilines and N-[4[(5,7-diamino-3-phenylquinoxalin-2-y1)amino]benzoyl]-L-glutamic acid diethyl ester; Evaluation of in vitro anti-cancer and anti-folate activities," European Journal of Medicinal Chemistry 43 (2008) 189-203.

Paola Corona et al., "Synthesis and in vitro antitumor activity of new quinoxaline derivatives," European Journal of Medicinal Chemistry 44 (2009) 1579-1591.

Andrew M. Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem. 2000, 43, 4200-4211.

James M. Hamby et al., "Structure-Activity Relationships for a Novel Series of Pyrido[2,3-d]pyrimidine Tyrosine Kinase Inhibitors," Journal of Medicinal Chemistry, 1997, vol. 40, No. 15, 2296-2303.

Perera et al., "JNJ-42756493 is an inhibitor of FGFR-1, 2, 3 and 4 with nanomolar affinity for targeted therapy (Abstract 1738)", Cancer Research, vol. 74, No. 19, Supplement, Oct. 1, 2014 (Oct. 1, 2014), pp. 1738-1738.

Poole, R.M. Pembrolizumab: First Global Approval. Drugs 74, 1973-1981 (2014). https://doi.org10.1007/s40265-014-03145 (Abstract only).

Neil Howard Segal et al, "Preliminary data from a multi-arm expansion study of MEDI4736, an anti-PD-L1 antibody", Journal of Clinical Oncology 2014 32:15_suppl, 3002 (Abstract only).

Villaruz LC et al, "Immunotherapy in lung cancer", Transl Lung Cancer Res. Feb. 2014;3(1):2-14. doi: 10.3978/j.issn.2218-6751.2013.10.13. PMID: 25806276; PMCID: PMC4367610.

Palakurthi, et al., "The Combined Effect of FGFR Inhibition and PD-1 Blockade Promotes Tumor-Intrinsic Induction of Antitumor Immunity", Cancer Immunology Research 7 (9), (2019), 1457-1472.

Thibault Voron et al., VEGF-A modulates expression of inhibitory checkpoints on CD8+ T cells in tumors, J. Exp. Med. 2015 vol. 212 No. 2, pp. 139-148.

OncLive Team, The Role of Anti-PD-L1 Immunotherapy in Cancer, OncLive Jan. 2014.

* cited by examiner

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacctggacc gtgtccttac c                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttccccagt tccaggttct t                                          21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggacctgga ccgtgtcctt                                            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tataggtccg gtggacaggg                                                        20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggccatcctg ccccc                                                             15

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagcagtcca ggtcagccag                                                        20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctggaccgtg tccttaccgt                                                        20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcagcccagg attgaactgt                                                        20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggatcgaat tctcactctc aca                                                    23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccaagcaat ctgcgtattt g                                                      21

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggtagaaga cttggatcga attct                                    25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctcccggat tatttcttca aca                                      23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctcttcaat acagccctga tca                                      23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acttggatcg aattctcact ctca                                     24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggatcgaat tctcactctc aca                                      23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaaagcctg aattttcttg aataa                                    25

-continued

```
<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agggtgcatc aactcatgaa ttag                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acttggatcg aattctcact ctca                                          24

<210> SEQ ID NO 19
<211> LENGTH: 2850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgggcgccc ctgcctgcgc cctcgcgctc tgcgtggccg tggccatcgt ggccggcgcc       60
tcctcggagt ccttggggac ggagcagcgc gtcgtggggc gagcggcaga agtcccgggc      120
ccagagcccg gccagcagga gcagttggtc ttcggcagcg gggatgctgt ggagctgagc      180
tgtcccccgc ccggggtgg tcccatgggg cccactgtct gggtcaagga tggcacaggg       240
ctggtgccct cggagcgtgt cctggtgggg ccccagcggc tgcaggtgct gaatgcctcc      300
cacgaggact ccgggggccta cagctgccgg cagcggctca cgcagcgcgt actgtgccac      360
ttcagtgtgc gggtgacaga cgctccatcc tcgggagatg acgaagacgg ggaggacgag       420
gctgaggaca caggtgtgga cacaggggcc ccttactgga cacggcccga gcggatggac       480
aagaagctgc tggccgtgcc ggccgccaac accgtccgct tccgctgccc agccgctggc       540
aaccccactc cctccatctc ctggctgaag aacggcaggg agttccgcgg cgagcaccgc       600
attggaggca tcaagctgcg gcatcagcag tggagcctgg tcatggaaag cgtggtgccc       660
tcggaccgcg gcaactacac ctgcgtcgtg gagaacaagt ttggcagcat ccggcagacg       720
tacacgctgg acgtgctgga gcgctccccg caccggccca tcctgcaggc ggggctgccg       780
gccaaccaga cggcggtgct gggcagcgac gtggagttcc actgcaaggt gtacagtgac       840
gcacagcccc acatccagtg gctcaagcac gtggaggtga atggcagcaa ggtgggcccg       900
gacggcacac cctacgttac cgtgctcaag acggcgggcg ctaacaccac cgacaaggag       960
ctagaggttc tctccttgca caacgtcacc tttgaggacg ccggggagta cacctgcctg      1020
gcgggcaatt ctattgggtt ttctcatcac tctgcgtggc tggtggtgct gccagccgag      1080
gaggagctgg tggaggctga cgaggcgggc agtgtgtatg caggcatcct cagctacggg      1140
gtgggcttct tcctgttcat cctggtggtg gcggctgtga cgctctgccg cctgcgcagc      1200 cccccccaaga aaggcctggg ctccccccacc gtgcacaaga tctcccgctt cccgctcaag      1260
```

```
cgacaggtgt ccctggagtc caacgcgtcc atgagctcca acacaccact ggtgcgcatc      1320
gcaaggctgt cctcagggga gggccccacg ctggccaatg tctccgagct cgagctgcct      1380
gccgacccca aatgggagct gtctcgggcc cggctgaccc tgggcaagcc ccttggggag      1440
ggctgcttcg gccaggtggt catggcggag gccatcggca ttgacaagga ccgggccgcc      1500
aagcctgtca ccgtagccgt gaagatgctg aaagacgatg ccactgacaa ggacctgtcg      1560
gacctggtgt ctgagatgga gatgatgaag atgatcggga aacacaaaaa catcatcaac      1620
ctgctgggcg cctgcacgca gggcgggccc ctgtacgtgc tggtggagta cgcggccaag      1680
ggtaacctgc gggagtttct gcgggcgcgg cggcccccgg gcctggacta ctccttcgac      1740
acctgcaagc cgcccgagga gcagctcacc ttcaaggacc tggtgtcctg tgcctaccag      1800
gtggcccggg gcatggagta cttggcctcc cagaagtgca tccacaggga cctggctgcc      1860
cgcaatgtgc tggtgaccga ggacaacgtg atgaagatcg cagacttcgg gctggcccgg      1920
gacgtgcaca acctcgacta ctacaagaag acgaccaacg gccggctgcc cgtgaagtgg      1980
atggcgcctg aggccttgtt tgaccgagtc tacactcacc agagtgacgt ctggtccttt      2040
ggggtcctgc tctgggagat cttcacgctg gggggctccc cgtaccccgg catccctgtg      2100
gaggagctct tcaagctgct gaaggagggc caccgcatgg acaagcccgc caactgcaca      2160
cacgacctgt acatgatcat gcgggagtgc tggcatgccg cgccctccca gaggcccacc      2220
ttcaagcagc tggtggagga cctggaccgt gtccttaccg tgacgtccac cgacgtaaag      2280
gcgacacagg aggagaaccg ggagctgagg agcaggtgtg aggagctcca cgggaagaac      2340
ctggaactgg ggaagatcat ggacaggttc gaagaggttg tgtaccaggc catggaggaa      2400
gttcagaagc agaaggaact ttccaaagct gaaatccaga aagttctaaa agaaaaagac      2460
caacttacca cagatctgaa ctccatggag aagtccttct ccgacctctt caagcgtttt      2520
gagaaacaga aagaggtgat cgagggctac cgcaagaacg aagagtcact gaagaagtgc      2580
gtggaggatt acctggcaag gatcacccag gagggccaga ggtaccaagc cctgaaggcc      2640
cacgcggagg agaagctgca gctggcaaac gaggagatcg cccaggtccg gagcaaggcc      2700
caggcggaag cgttggccct ccaggccagc ctgaggaagg agcagatgcg catccagtcg      2760
ctggagaaga cagtggagca gaagactaaa gagaacgagg agctgaccag gatctgcgac      2820
gacctcatct ccaagatgga gaagatctga                                        2850
```

<210> SEQ ID NO 20
<211> LENGTH: 2955
<212> TYPE: DNA
<213> ORGANISM: Artificial Sequence
<220> FEATURE:
<223> OTHER INFORMATION: Description of Artificial Sequence: Synthetic
     polynucleotide <400> SEQUENCE: 20

```
atgggcgccc ctgcctgcgc cctcgcgctc tgcgtggccg tggccatcgt ggccggcgcc        60
tcctcggagt cccttgggga cggagcagcgc gtcgtggggc gagcggcaga agtcccgggc       120
ccagagcccg gccagcagga gcagttggtc ttcggcagcg gggatgctgt ggagctgagc       180
tgtcccccgc ccgggggtgg tcccatgggg cccactgtct gggtcaagga tggcacaggg       240
ctggtgccct cggagcgtgt cctggtgggg ccccagcggc tgcaggtgct gaatgcctcc       300
cacgaggact ccgggggccta cagctgccgg cagcggctca cgcagcgcgt actgtgccac       360
ttcagtgtgc gggtgacaga cgctccatcc tcgggagatg acgaagacgg ggaggacgag       420
```

-continued

```
gctgaggaca caggtgtgga cacaggggcc ccttactgga cacggcccga gcggatggac      480
aagaagctgc tggccgtgcc ggccgccaac accgtccgct tccgctgccc agccgctggc      540
aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt ttggcagcat ccggcagacg      720
tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga atggcagcaa ggtgggcccg      900
gacggcacac cctacgttac cgtgctcaag acggcgggcg ctaacaccac cgacaaggag      960
ctagaggttc tctccttgca caacgtcacc tttgaggacg ccggggagta cacctgcctg     1020
gcgggcaatt ctattgggtt ttctcatcac tctgcgtggc tggtggtgct gccagccgag     1080
gaggagctgg tggaggctga cgaggcgggc agtgtgtatg caggcatcct cagctacggg     1140
gtgggcttct tcctgttcat cctggtggtg gcggctgtga cgctctgccg cctgcgcagc     1200 cccccaaga aaggcctggg ctcccccacc gtgcacaaga tctcccgctt cccgctcaag     1260
cgacaggtgt ccctggagtc caacgcgtcc atgagctcca acaccact ggtgcgcatc      1320 gcaaggctgt cctcagggga gggccccacg ctggccaatg tctccgagct cgagctgcct     1380
gccgacccca atgggagct gtctcgggcc cggctgaccc tgggcaagcc ccttggggag      1440
ggctgcttcg ccaggtggt catggcggag gccatcggca ttgacaagga ccgggccgcc     1500
aagcctgtca ccgtagccgt gaagatgctg aaagacgatg ccactgacaa ggacctgtcg     1560
gacctggtgt ctgagatgga gatgatgaag atgatcggga aacacaaaaa catcatcaac     1620
ctgctgggcg cctgcacgca gggcgggccc ctgtacgtgc tggtggagta cgcggccaag     1680
ggtaacctgc gggagtttct gcgggcgcgg cggcccccgg gcctggacta ctccttcgac     1740
acctgcaagc cgcccgagga gcagctcacc ttcaaggacc tggtgtcctg tgcctaccag     1800
gtggcccggg gcatggagta cttggcctcc cagaagtgca tccacaggga cctggctgcc     1860
cgcaatgtgc tggtgaccga ggacaacgtg atgaagatcg cagacttcgg gctggcccgg     1920
gacgtgcaca acctcgacta ctacaagaag acgaccaacg gccggctgcc cgtgaagtgg     1980
atggcgcctg aggccttgtt tgaccgagtc tacactcacc agagtgacgt ctggtccttt     2040
ggggtcctgc tctgggagat cttcacgctg ggggggctccc cgtaccccgg catccctgtg     2100
gaggagctct tcaagctgct gaaggagggc accgcatgg acaagcccgc caactgcaca     2160
cacgacctgt acatgatcat gcgggagtgc tggcatgccg cgccctccca gaggcccacc     2220
ttcaagcagc tggtggagga cctggaccgt gtccttaccg tgacgtccac cgacgtgcca     2280
ggcccacccc caggtgttcc cgcgcctggg ggcccacccc tgtccaccgg acctatagtg     2340
gacctgctcc agtacagcca gaaggacctg atgcagtgg taaaggcgac acaggaggag     2400
aaccgggagc tgaggagcag gtgtgaggag ctccacggga agaacctgga actggggaag     2460
atcatggaca ggttcgaaga ggttgtgtac caggccatgg aggaagttca gaagcagaag     2520
gaactttcca aagctgaaat ccagaaagtt ctaaaagaaa aagaccaact taccacagat     2580
ctgaactcca tggagaagtc cttctccgac ctcttcaagc gttttgagaa acagaaagag     2640
gtgatcgagg gctaccgcaa gaacgaagag tcactgaaga agtgcgtgga ggattacctg     2700
gcaaggatca cccaggaggg ccagaggtac caagccctga ggcccacgc ggaggagaag     2760 ctgcagctgg caaacgagga gatcgcccag gtccggagca aggcccaggc ggaagcgttg     2820
```

```
gccctccagg ccagcctgag gaaggagcag atgcgcatcc agtcgctgga gaagacagtg      2880
gagcagaaga ctaaagagaa cgaggagctg accaggatct gcgacgacct catctccaag      2940
atggagaaga tctga                                                       2955

<210> SEQ ID NO 21
<211> LENGTH: 4462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgggcgccc ctgcctgcgc cctcgcgctc tgcgtggccg tggccatcgt ggccggcgcc        60
tcctcggagt ccttggggac ggagcagcgc gtcgtggggc gagcggcaga agtcccgggc       120
ccagagcccg gccagcagga gcagttggtc ttcggcagcg gggatgctgt ggagctgagc       180
tgtcccccgc ccgggggtgg tcccatgggg cccactgtct gggtcaagga tggcacaggg       240
ctggtgccct cggagcgtgt cctggtgggg ccccagcggc tgcaggtgct gaatgcctcc       300
cacgaggact ccggggccta cagctgccgg cagcggctca cgcagcgcgt actgtgccac       360
ttcagtgtgc gggtgacaga cgctccatcc tcgggagatg acgaagacgg ggaggacgag       420
gctgaggaca caggtgtgga cacaggggcc ccttactgga cacggcccga gcggatggac       480
aagaagctgc tggccgtgcc ggccgccaac accgtccgct tccgctgccc agccgctggc       540
aaccccactc cctccatctc ctggctgaag aacggcaggg agttccgcgg cgagcaccgc       600
attggaggca tcaagctgcg gcatcagcag tggagcctgg tcatggaaag cgtggtgccc       660
tcggaccgcg gcaactacac ctgcgtcgtg gagaacaagt ttggcagcat ccggcagacg       720
tacacgctgg acgtgctgga gcgctccccg caccggccca tcctgcaggc ggggctgccg       780
gccaaccaga cggcggtgct gggcagcgac gtggagttcc actgcaaggt gtacagtgac       840
gcacagcccc acatccagtg gctcaagcac gtggaggtga atggcagcaa ggtgggcccg       900
gacggcacac cctacgttac cgtgctcaag acggcgggcg ctaacaccac cgacaaggag       960
ctagaggttc tctccttgca caacgtcacc tttgaggacg ccggggagta cacctgcctg      1020
gcgggcaatt ctattgggtt ttctcatcac tctgcgtggc tggtggtgct gccagccgag      1080
gaggagctgg tggaggctga cgaggcgggc agtgtgtatg caggcatcct cagctacggg      1140
gtgggcttct tcctgttcat cctggtggtg gcggctgtga cgctctgccg cctgcgcagc      1200 cccccaaga aaggcctggg ctcccccacc gtgcacaaga tctcccgctt cccgctcaag      1260
cgacaggtgt ccctggagtc caacgcgtcc atgagctcca cacaccact ggtgcgcatc      1320 gcaaggctgt cctcagggga gggccccacg ctggccaatg tctccgagct cgagctgcct      1380
gccgacccca atgggagct gtctcgggcc cggctgaccc tgggcaagcc ccttggggag      1440
ggctgcttcg ccaggtggt catggcggag gccatcggca ttgacaagga ccgggccgcc      1500
aagcctgtca ccgtagccgt gaagatgctg aaagacgatg ccactgacaa ggacctgtcg      1560
gacctggtgt ctgagatgga gatgatgaag atgatcggga acacaaaaaa catcatcaac      1620
ctgctgggcg cctgcacgca gggcgggccc ctgtacgtgc tggtggagta cgcggccaag      1680
ggtaacctgc gggagtttct gcgggcgcgg cggcccccgg gcctggacta ctccttcgac      1740
acctgcaagc cgcccgagga gcagctcacc ttcaaggacc tggtgtcctg tgcctaccag      1800
gtggcccggg gcatggagta cttggcctcc cagaagtgca tccacaggga cctggctgcc      1860
```

```
cgcaatgtgc tggtgaccga ggacaacgtg atgaagatcg cagacttcgg gctggcccgg      1920
gacgtgcaca acctcgacta ctacaagaag acgaccaacg gccggctgcc cgtgaagtgg      1980
atggcgcctg aggccttgtt tgaccgagtc tacactcacc agagtgacgt ctggtccttt      2040
ggggtcctgc tctgggagat cttcacgctg gggggctccc cgtaccccgg catccctgtg      2100
gaggagctct tcaagctgct gaaggagggc caccgcatgg acaagcccgc caactgcaca      2160
cacgacctgt acatgatcat gcgggagtgc tggcatgccg cgccctccca gaggcccacc      2220
ttcaagcagc tggtggagga cctggaccgt gtccttaccg tgacgtccac cgacgtgagt      2280
gctggctctg gctggtgcc acccgcctat gcccctcccc ctgccgtccc cggccatcct      2340 gcccccaga gtgctgaggt gtggggcggg cctttctggc ccaggtgccc tggctgacct      2400
ggactgctca agctcttccc agagcccagg aagttctgag aaccaaatgg tgtctccagg      2460
aaaagtgtct ggcagccctg agcaagccgt ggaggaaaac cttagttcct attccttaga      2520
cagaagagtg acacccgcct ctgagaccct agaagaccct tgcaggacag agtcccagca      2580
caaagcggag actccgcacg gagccgagga agaatgcaaa gcggagactc cgcacggagc      2640
cgaggaggaa tgccggcacg gtggggtctg tgctcccgca gcagtggcca cttcgcctcc      2700
tggtgcaatc cctaaggaag cctgcggagg agcacccctg cagggtctgc ctggcgaagc      2760
cctgggctgc cctgcgggtg tgggcacccc cgtgccagca gatggcactc agaccccttac      2820 ctgtgcacac acctctgctc ctgagagcac agccccaacc aaccacctgg tggctggcag      2880
ggccatgacc ctgagtcctc aggaagaagt ggctgcaggc caaatggcca gctcctcgag      2940
gagcggacct gtaaaactag aatttgatgt atctgatggc gccaccagca aaagggcacc      3000
cccaccaagg agactgggag agaggtccgg cctcaagcct cccttgagga aagcagcagt      3060
gaggcagcaa aaggccccgc aggaggtgga ggaggacgac ggtaggagcg gagcaggaga      3120
ggaccccccc atgccagctt ctcggggctc ttaccacctc gactgggaca aaatggatga      3180
cccaaacttc atcccgttcg gaggtgacac caagtctggt tgcagtgagg cccagccccc      3240
agaaagccct gagaccaggc tgggccagcc agcggctgaa cagttgcatg ctgggcctgc      3300
cacggaggag ccaggtccct gtctgagcca gcagctgcat tcagcctcag cggaggacac      3360
gcctgtggtg cagttggcag ccgagacccc aacagcagag agcaaggaga gagccttgaa      3420
ctctgccagc acctcgcttc ccacaagctg tccaggcagt gagccagtgc ccacccatca      3480
gcaggggcag cctgccttgg agctgaaaga ggagagcttc agagaccccg ctgaggttct      3540
aggcacgggc gcgaggtgg attacctgga gcagtttgga acttcctcgt ttaaggagtc      3600
ggccttgagg aagcagtcct tatacctcaa gttcgacccc ctcctgaggg acagtcctgg      3660
tagaccagtg cccgtggcca ccgagaccag cagcatgcac ggtgcaaatg agactccctc      3720
aggacgtccg cgggaagcca agcttgtgga gttcgatttc ttgggagcac tggacattcc      3780
tgtgccaggc ccacccccag gtgttcccgc gcctgggggc ccacccctgt ccaccggacc      3840
tatagtggac ctgctccagt acagccagaa ggacctggat gcagtggtaa aggcgacaca      3900
ggaggagaac cgggagctga ggagcaggtg tgaggagctc cacgggaaga acctggaact      3960
ggggaagatc atggacaggt tcgaagaggt tgtgtaccag gccatggagg aagttcagaa      4020
gcagaaggaa ctttccaaag ctgaaatcca gaaagttcta aaagaaaaag accaacttac      4080
cacagatctg aactccatgg agaagtcctt ctccgacctc ttcaagcgtt ttgagaaaca      4140
gaaagaggtg atcgagggct accgcaagaa cgaagagtca ctgaagaagt gcgtggagga      4200
```

-continued

```
ttacctggca aggatcaccc aggagggcca gaggtaccaa gccctgaagg cccacgcgga      4260
ggagaagctg cagctggcaa acgaggagat cgcccaggtc cggagcaagg cccaggcgga      4320
agcgttggcc ctccaggcca gcctgaggaa ggagcagatg cgcatccagt cgctggagaa      4380
gacagtggag cagaagacta aagagaacga ggagctgacc aggatctgcg acgacctcat      4440
ctccaagatg gagaagatct ga                                              4462
```

```
<210> SEQ ID NO 22
<211> LENGTH: 3765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
```

```
atgggcgccc ctgcctgcgc cctcgcgctc tgcgtggccg tggccatcgt ggccggcgcc        60
tcctcggagt ccttggggac ggagcagcgc gtcgtggggc gagcggcaga agtcccgggc       120
ccagagcccg gccagcagga gcagttggtc ttcggcagcg gggatgctgt ggagctgagc       180 tgtccccgc  ccgggggtgg tcccatgggg cccactgtct gggtcaagga tggcacaggg       240
ctggtgccct cggagcgtgt cctggtgggg ccccagcggc tgcaggtgct gaatgcctcc       300
cacgaggact ccgggggccta cagctgccgg cagcggctca cgcagcgcgt actgtgccac       360
ttcagtgtgc gggtgacaga cgctccatcc tcgggagatg acgaagacgg ggaggacgag       420
gctgaggaca caggtgtgga cacaggggcc cctt actgga cacggcccga gcggatggac       480
aagaagctgc tggccgtgcc ggccgccaac accgtccgct tccgctgccc agccgctggc       540
aaccccactc cctccatctc ctggctgaag aacggcaggg agttccgcgg cgagcaccgc       600
attggaggca tcaagctgcg gcatcagcag tggagcctgg tcatggaaag cgtggtgccc       660
tcggaccgcg gcaactacac ctgcgtcgtg gagaacaagt ttggcagcat ccggcagacg       720
tacacgctgg acgtgctgga gcgctccccg caccggccca tcctgcaggc ggggctgccg       780
gccaaccaga cggcggtgct gggcagcgac gtggagttcc actgcaaggt gtacagtgac       840
gcacagcccc acatccagtg gctcaagcac gtggaggtga atggcagcaa ggtgggcccg       900
gacggcacac cctacgttac cgtgctcaag tcctggatca gtgagagtgt ggaggccgac       960
gtgcgcctcc gcctggccaa tgtgtcggag cgggacgggg cgagtacct ctgtcgagcc      1020 accaatttca taggcgtggc cgagaaggcc ttttggctga gcgttcacgg gccccgagca      1080
gccgaggagg agctggtgga ggctgacgag gcgggcagtg tgtatgcagg catcctcagc      1140 tacgggggtgg gcttcttcct gttcatcctg gtggtggcgg ctgtgacgct ctgccgcctg      1200
cgcagccccc caagaaagg cctgggctcc cccaccgtgc acaagatctc ccgcttcccg      1260
ctcaagcgac aggtgtccct ggagtccaac gcgtccatga ctccaacac accactggtg      1320 cgcatcgcaa ggctgtcctc aggggagggc cccacgctgg ccaatgtctc cgagctcgag      1380
ctgcctgccg accccaaatg ggagctgtct cgggcccggc tgaccctggg caagcccctt      1440
ggggagggct gcttcggcca ggtggtcatg gcggaggcca tcggcattga caaggaccgg      1500
gccgccaagc ctgtcaccgt agccgtgaag atgctgaaag acgatgccac tgacaaggac      1560
ctgtcggacc tggtgtctga gatggagatg atgaagatga tcgggaaaca caaaaacatc      1620
atcaacctgc tggcgcctg cacgcagggc gggccctgt acgtgctggt ggagtacgcg      1680
gccaagggta acctgcggga gtttctgcgg gcgcggcggc cccgggcct ggactactcc      1740
```

-continued

```
ttcgacacct gcaagccgcc cgaggagcag ctcaccttca aggacctggt gtcctgtgcc    1800
taccaggtgg cccgggggcat ggagtacttg gcctcccaga agtgcatcca cagggacctg    1860
gctgcccgca atgtgctggt gaccgaggac aacgtgatga agatcgcaga cttcgggctg    1920
gcccgggacg tgcacaacct cgactactac aagaagacga ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg gctccccgta ccccggcatc    2100
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt ggaggacctg gaccgtgtcc ttaccgtgac gtccaccgac    2280
aatgttatgg aacagttcaa tcctgggctg cgaaatttaa taaacctggg gaaaaattat    2340
gagaaagctg taaacgctat gatcctggca ggaaaagcct actacgatgg agtggccaag    2400
atcggtgaga ttgccactgg gtcccccgtg tcaactgaac tgggacatgt cctcatagag    2460
atttcaagta cccacaagaa actcaacgag agtcttgatg aaaattttaa aaaattccac    2520
aaagagatta tccatgagct ggagaagaag atagaacttg acgtgaaata tatgaacgca    2580
actctaaaaa gataccaaac agaacacaag aataaaattag agtctttgga gaaatcccaa    2640
gctgagttga agaagatcag aaggaaaagc caaggaagcc gaaacgcact caaatatgaa    2700
cacaaagaaa ttgagtatgt ggagaccgtt acttctcgtc agagtgaaat ccagaaattc    2760
attgcagatg gttgcaaaga ggctctgctt gaagagaaga ggcgcttctg ctttctggtt    2820
gataagcact gtggctttgc aaaccacata cattattatc acttacagtc tgcagaacta    2880
ctgaattcca agctgcctcg gtggcaggag acctgtgttg atgccatcaa agtgccagag    2940
aaaatcatga atatgatcga agaaataaag accccagcct ctaccccgt gtctggaact    3000 cctcaggctt cacccatgat cgagagaagc aatgtggtta ggaaagatta cgacaccctt    3060
tctaaatgct caccaaagat gcccccgct ccttcaggca gagcatatac cagtcccttg    3120
atcgatatgt ttaataaccc agccacggct gccccgaatt cacaaagggt aaataattca    3180
acaggtactt ccgaagatcc cagtttacag cgatcagttt cggttgcaac gggactgaac    3240
atgatgaaga agcagaaagt gaagaccatc ttcccgcaca ctgcgggctc caacaagacc    3300
ttactcagct ttgcacaggg agatgtcatc acgctgctca tccccgagga gaaggatggc    3360
tggctctatg gagaacacga cgtgtccaag gcgaggggtt ggttcccgtc gtcgtacacg    3420
aagttgctgg aagaaaatga gacagaagca gtgaccgtgc ccacgccaag ccccacacca    3480
gtgagaagca tcagcaccgt gaacttgtct gagaatagca gtgttgtcat cccccaccc    3540 gactacttgg aatgcttgtc catggggggca gctgccgaca ggagagcaga ttcggccagg    3600
acgacatcca cctttaaggc cccagcgtcc aagcccgaga ccgcggctcc taacgatgcc    3660
aacgggactg caaagccgcc ttttctcagc ggagaaaacc cctttgccac tgtgaaactc    3720
cgcccgactg tgacgaatga tcgctcggca cccatcattc gatga                     3765
```

<210> SEQ ID NO 23
<211> LENGTH: 4989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

-continued

```
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc caggggagtc gctagaggtg     180
cgctgcctgt tgaaagatgc cgccgtgatc agttggacta aggatggggt gcacttgggg     240
cccaacaata ggacagtgct tattggggag tacttgcaga taaagggcgc cacgcctaga     300
gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac caacacagaa     480
aagatggaaa agcggctcca tgctgtgcct gcggccaaca ctgtcaagtt tcgctgccca     540
gccgggggga acccaatgcc aaccatgcgg tggctgaaaa acgggaagga gtttaagcag     600
gagcatcgca ttggaggcta caaggtacga aaccagcact ggagcctcat tatggaaagt     660
gtggtcccat ctgacaaggg aaattatacc tgtgtagtgg agaatgaata cgggtccatc     720
aatcacacgt accacctgga tgttgtggag cgatcgcctc accggcccat cctccaagcc     780
ggactgccgg caaatgcctc cacagtggtc ggaggagacg tagagtttgt ctgcaaggtt     840
tacagtgatg cccagcccca catccagtgg atcaagcacg tggaaaagaa cggcagtaaa     900
tacgggcccg acgggctgcc ctacctcaag gttctcaagg ccgccggtgt taacaccacg     960
gacaaagaga ttgaggttct ctatattcgg aatgtaactt ttgaggacgc tggggaatat    1020
acgtgcttgg cgggtaattc tattgggata tcctttcact ctgcatggtt gacagttctg    1080
ccagcgcctg gaagagaaaa ggagattaca gcttccccag actacctgga gatagccatt    1140
tactgcatag gggtcttctt aatcgcctgt atggtggtaa cagtcatcct gtgccgaatg    1200
aagaacacga ccaagaagcc agacttcagc agccagccgg ctgtgcacaa gctgaccaaa    1260
cgtatccccc tgcggagaca ggtaacagtt tcggctgagt ccagctcctc catgaactcc    1320 aacacccgc tggtgaggat aacaacacgc ctctcttcaa cggcagacac ccccatgctg    1380
gcaggggtct ccgagtatga acttccagag acccaaaat gggagtttcc aagagataag    1440
ctgacactgg gcaagcccct gggagaaggt tgctttgggc aagtggtcat ggcggaagca    1500
gtgggaattg acaaagacaa gcccaaggag gcggtcaccg tggccgtgaa gatgttgaaa    1560
gatgatgcca cagagaaaga cctttctgat ctggtgtcag agatggagat gatgaagatg    1620
attgggaaac acaagaatat cataaatctt cttggagcct gcacacagga tgggcctctc    1680
tatgtcatag ttgagtatgc ctctaaaggc aacctccgag aatacctccg agcccggagg    1740
ccacccggga tggagtactc ctatgacatt aaccgtgttc ctgaggagca gatgaccttc    1800
aaggacttgg tgtcatgcac ctaccagctg gccagaggca tggagtactt ggcttcccaa    1860
aaatgtattc atcgagattt agcagccaga aatgttttgg taacagaaaa caatgtgatg    1920
aaaatagcag actttggact cgccagagat atcaacaata tagactatta caaaaagacc    1980
accaatgggc ggcttccagt caagtggatg gctccagaag ccctgtttga tagagtatac    2040
actcatcaga gtgatgtctg tgtccttcgg gtgttaatgt gggagatctt cacttagggg    2100
ggctcgccct acccagggat tcccgtggag gaactttta agctgctgaa ggaaggacac    2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga gatcatggag gaaacaaata cgcagattgc ttggccatca    2340
aaactgaaga tcggagccaa atccaagaaa gatccccata ttaaggtttc tggaaagaaa    2400
```

-continued

```
gaagatgtta aagaagccaa ggaaatgatc atgtctgtct tagacacaaa aagcaatcga   2460
gtcacactga agatggatgt ttcacataca gaacattcac atgtaatcgg caaaggtggc   2520
aacaatatta aaaaagtgat ggaagaaacc ggatgccata tccactttcc agattccaac   2580
aggaataacc aagcagaaaa aagcaaccag gtatctatag cgggacaacc agcaggagta   2640
gaatctgccc gagttagaat tcgggagctg cttcctttgg tgctgatgtt tgagctacca   2700
attgctggaa ttcttcaacc ggttcctgat cctaattccc cctctattca gcatatatca   2760
caaacgtaca atatttcagt atcatttaaa cagcgttccc gaatgtatgg tgctactgtc   2820
atagtacgag ggtctcagaa taacactagt gctgtgaagg aaggaactgc catgctgtta   2880
gaacatcttg ctgggagctt agcatcagct attcctgtga gcacacaact agatattgca   2940
gctcaacatc atctctttat gatgggtcga aatgggagca acatcaaaca tatcatgcag   3000
agaacaggtg ctcagatcca ctttcctgat cccagtaatc cacaaaagaa atctaccgtc   3060
tacctccagg gcaccattga gtctgtctgt cttgcaaggc aatatctcat gggttgtctt   3120
cctcttgtgt tgatgtttga tatgaaggaa gaaattgaag tagatccaca attcattgcg   3180
cagttgatga aacagcttga tgtcttcatc agtattaaac caaagcccaa acagccaagc   3240
aagtctgtga ttgtgaaaag tgttgagcga aatgccttaa atatgtatga agcaaggaaa   3300
tgtctcctcg gacttgaaag cagtgggggtt accatagcaa ccagtccatc cccagcatcc   3360
tgccctgccg gcctggcatg tcccagcctg gatatcttag cttcagcagg ccttggactc   3420
actggactag gtctttggg acccaccacc ttatctctga acacttcaac aaccccaaac   3480
tcactcttga atgctcttaa tagctcagtc agtcctttgc aaagtccaag ttctggtaca   3540
cccagcccca cattatgggc accccacctt gctaatactt caagtgccac aggtttttct   3600
gctataccac accttatgat tccatctact gcccaagcca cattaactaa tattttgttg   3660
tctggagtgc ccacctatgg gcacacagct ccatctcccc ctcctggctt gactcctgtt   3720
gatgtccata tcaacagtat gcagaccgaa ggcaaaaaaa tctctgctgc tttaaatgga   3780
catgcacagt ctccagatat aaaatatggt gcaatatcca cttcatcact tggagaaaaa   3840
gtgctgagtg caaatcacgg ggatccgtcc atccagacaa gtgggtctga gcagacatct   3900
cccaaatcaa gccccactga aggttgtaat gatgcttttg ttgaagtagg catgcctcga   3960
agtccttccc attctgggaa tgctggtgac ttgaaacaga tgatgtgtcc ctccaaggtt   4020
tcctgtgcca aaaggcagac agtggaacta ttgcaaggca cgaaaaactc acacttacac   4080
agcactgaca ggttgctctc agaccctgaa ctgagtgcta ccgaaagccc tttggctgac   4140
aagaaggctc caggggagtga gcgcgctgca gagagggcag cagctgccca gcaaaactcc   4200
gaaagggccc accttgctcc acggtcatca tatgtcaaca tgcaggcatt tgactatgaa   4260
cagaagaagc tattagccac caaagctatg ttaaagaaac cagtggtgac ggaggtcaga   4320
acgcccacaa atacctggag tggcctgggt ttttctaaat ccatgccagc tgaaactatc   4380
aaggagttga gaagggccaa tcatgtgtcc tataagccca caatgacaac cacttatgag   4440
ggctcatcca tgtcccttttc acggtccaac agtcgtgagc acttgggagg tggaagcgaa   4500
tctgataact ggagagaccg aaatggaatt ggacctggaa gtcatagtga atttgcagct   4560
tctattggca gccctaagcg taaacaaaac aaatcaacgg aacactatct cagcagtagc   4620
aattacatgg actgcatttc ctcgctgaca ggaagcaatg gctgtaactt aaatagctct   4680
ttcaaaggtt ctgacctccc tgagctcttc agcaaactgg gcctgggcaa atacacagat   4740
```

-continued

```
gttttccagc aacaagagat cgatcttcag acattcctca ctctcacaga tcaggatctg     4800
aaggagctgg gaataactac ttttggtgcc aggaggaaaa tgctgcttgc aatttcagaa     4860
ctaaataaaa accgaagaaa gcttttttgaa tcgccaaatg cacgcacctc tttcctggaa     4920
ggtggagcga gtggaaggct accccgtcag tatcactcag acattgctag tgtcagtggc     4980
cgctggtag                                                             4989
```

```
<210> SEQ ID NO 24
<211> LENGTH: 5109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
```

```
atggtcagct ggggtcgttt catctgcctg gtcgtggtca ccatggcaac cttgtccctg       60
gcccggccct ccttcagttt agttgaggat accacattag agccagaaga gccaccaacc      120
aaataccaaa tctctcaacc agaagtgtac gtggctgcgc caggggagtc gctagaggtg      180
cgctgcctgt tgaaagatgc cgccgtgatc agttggacta aggatggggt gcacttgggg      240
cccaacaata ggacagtgct tattggggag tacttgcaga taaagggcgc cacgcctaga      300
gactccggcc tctatgcttg tactgccagt aggactgtag acagtgaaac ttggtacttc      360
atggtgaatg tcacagatgc catctcatcc ggagatgatg aggatgacac cgatggtgcg      420
gaagattttg tcagtgagaa cagtaacaac aagagagcac catactggac caacacagaa      480
aagatggaaa agcggctcca tgctgtgcct gcggccaaca ctgtcaagtt tcgctgccca      540
gccgggggga acccaatgcc aaccatgcgg tggctgaaaa acgggaagga gtttaagcag      600
gagcatcgca ttggaggcta caaggtacga aaccagcact ggagcctcat tatggaaagt      660
gtggtcccat ctgacaaggg aaattatacc tgtgtagtgg agaatgaata cgggtccatc      720
aatcacacgt accacctgga tgttgtggag cgatcgcctc accggcccat cctccaagcc      780
ggactgccgg caaatgcctc cacagtggtc ggaggagacg tagagtttgt ctgcaaggtt      840
tacagtgatg cccagcccca tccagtggg atcaagcacg tggaaaagaa cggcagtaaa      900
tacgggcccg acgggctgcc ctacctcaag gttctcaagg ccgccggtgt taacaccacg      960
gacaaagaga ttgaggttct ctatattcgg aatgtaactt ttgaggacgc tggggaatat     1020
acgtgcttgg cgggtaattc tattgggata tcctttcact ctgcatggtt gacagttctg     1080
ccagcgcctg aagagaaaa ggagattaca gcttccccag actacctgga gatagccatt     1140
tactgcatag gggtcttctt aatcgcctgt atggtggtaa cagtcatcct gtgccgaatg     1200
aagaacacga ccaagaagcc agacttcagc agccagccgg ctgtgcacaa gctgaccaaa     1260 cgtatcccc tgcggagaca ggtaacagtt tcggctgagt ccagctcctc catgaactcc     1320 aacacccgc tggtgaggat aacaacacgc ctctcttcaa cggcagacac ccccatgctg     1380
gcaggggtct ccgagtatga acttccagag acccaaaat gggagtttcc aagagataag     1440
ctgacactgg gcaagcccct gggagaaggt tgctttgggc aagtggtcat ggcggaagca     1500
gtgggaattg acaaagacaa gcccaaggag gcggtcaccg tggccgtgaa gatgttgaaa     1560
gatgatgcca cagagaaaga cctttctgat ctggtgtcag agatggagat gatgaagatg     1620
attgggaaac acaagaatat cataaatctt cttggagcct gcacacagga tgggcctctc     1680
tatgtcatag ttgagtatgc ctctaaaggc aacctccgag aatacctccg agcccggagg     1740
```

-continued

```
ccacccggga tggagtactc ctatgacatt aaccgtgttc ctgaggagca gatgaccttc      1800
aaggacttgg tgtcatgcac ctaccagctg gccagaggca tggagtactt ggcttcccaa      1860
aaatgtattc atcgagattt agcagccaga aatgtttygg taacagaaaa caatgtgatg      1920
aaaatagcag actttggact cgccagagat atcaacaata tagactatta caaaaagacc      1980
accaatgggc ggcttccagt caagtggatg gctccagaag ccctgtttga tagagtatac      2040
actcatcaga gtgatgtctg gtccttcggg gtgttaatgt gggagatctt cactttaggg      2100
ggctcgccct acccagggat tcccgtggag gaactttta agctgctgaa ggaaggacac      2160
agaatggata agccagccaa ctgcaccaac gaactgtaca tgatgatgag ggactgttgg      2220
catgcagtgc cctcccagag accaacgttc aagcagttgg tagaagactt ggatcgaatt      2280
ctcactctca caaccaatga ggagagtaga tctggagaaa ccaacagctg tgttgaagaa      2340
ataatccggg agatgacctg gcttccacca ctttctgcta ttcaagcacc tggcaaagtg      2400
gaaccaacca aatttccatt tccaaataag gactctcagc ttgtatcctc tggacacaat      2460
aatccaaaga aaggtgatgc agagccagag agtccagaca gtggcacatc gaatacatca      2520
atgctggaag atgaccttaa gctaagcagt gatgaagagg agaatgaaca gcaggcagct      2580
cagagaacgg ctctccgcgc tctctctgac agcgccgtgg tccagcagcc caactgcaga      2640
acctcggtgc cttccagcaa gggcagcagc agcagcagca gcagcggcag cagcagctcc      2700
tccagcgact cagagagcag ctccggatct gactcggaga ccgagagcag ctccagcgag      2760
agtgagggca gcaagccccc ccacttctcc agccccgagg ctgaaccggc atcctctaac      2820
aagtggcagc tggataaatg gctaaacaaa gttaatcccc acaagcctcc tattctgatc      2880
caaaatgaaa gccacgggtc agagagcaat cagtactaca acccggtgaa agaggacgtc      2940
caggactgtg ggaaagtccc cgacgtttgc agcccagcc tgagagagaa ggagatcaag      3000
agcacttgca aggaggagca aaggccaagg acagccaaca aggcccctgg gagtaaaggc      3060
gtgaagcaga gtccccgccc cgcggccgtg gccgtggcgg tgagcgcagc cgccccgcca      3120
cccgcagtgc cctgtgcgcc cgcggagaac gcgcccgcgc ctgcccggag gtccgcgggc      3180
aagaagccca ccaggcgcac cgagaggacc tcagccgggg acggcgccaa ctgccaccgg      3240
cccgaggagc ccgcggccgc ggacgcgctg gggacgagcg tggtggtccc cccggagccc      3300
accaaaacca ggccctgtgg caacaacaga gcgagccacc gcaaggagct gcgctcctcc      3360
gtgacctgcg agaagcgccg cacgcggggg ctaagcagga tcgtccccaa atccaaggag      3420
ttcattgaga cagagtcgtc atcttcatcc tcctcctcgg actccgacct ggagtccgag      3480
caggaggagt accctctgtc caaagcacag accgtggctg cctctgcctc ctccgggaat      3540
gatcagaggc tgaaggaggc cgctgccaac gggggcagtg tcctagggc ccctgtaggc      3600 tccatcaacg ccaggaccac cagtgacatc gccaaggagc tggaggagca gttctacaca      3660 ctggtccccct ttggccggaa cgaacttctc tccctctaa aggacagtga tgagatcagg      3720
tctctctggg tcaaaatcga cctgacctc ctgtccagga tcccagaaca cctgccccag      3780
gagccagggg tattgagcgc ccctgccacc aaggactctg agagcgcacc gcccagccac      3840
acctcggaca cacctgcaga aaaggctttg ccaaaatcca agaggaaacg caagtgtgac      3900
aacgaagacg actacaggga gatcaagaag tcccagggag agaaagacag ctcttcaaga      3960
ctggccacct ccaccagtaa tactttgtct gcaaaccact gcaacatgaa catcaacagt      4020
gtggcaatac caataaataa aaatgaaaaa atgcttcggt cgcccatctc accctctct      4080 gatgcatcta aacacaaata caccagcgag gacttaactt cttccagccg acctaatggc      4140
```

-continued

```
aacagtttgt ttacttcagc ctcttccagc aaaaagccta aggccgacag ccagctgcag      4200
cctcacggcg gagacctcac gaaagcagct cacaacaatt ctgaaaacat tcccctccac      4260
aagtcacggc cgcagacgaa gccgtggtct ccaggctcca acggccacag ggactgcaag      4320
aggcagaaac ttgtcttcga tgatatgcct cgcagtgccg attattttat gcaagaagct      4380
aaacgaatga agcataaagc agatgcaatg gtggaaaagt ttggaaaggc tttgaactat      4440
gctgaagcag cattgtcgtt tatcgagtgt ggaaatgcaa tggaacaagg ccccatggaa      4500
tccaaatctc cttatacgat gtattcagaa acagtagagc tcatcaggta tgctatgaga      4560
ctaaaaaccc actcaggccc caatgccaca ccagaagaca aacaactggc tgcattatgt      4620
taccgatgcc tggccctcct gtactggcgg atgtttcgac tcaaaaggga ccacgctgta      4680
aagtattcaa aagcactaat cgactatttc aagaactcat ctaaagccgc ccaagcccca      4740
tctccgtggg gggccagtgg aaagagcact ggaacccat cccccatgtc tcccaacccc      4800
tctcccgcca gctccgtggg gtctcaggg agcctctcca acgccagcgc cctgtccccg      4860
tcgaccatcg tcagcatccc acagcgcatc caccagatgg cggccaacca cgtcagcatc      4920
accaacagca tcctgcacag ctacgactac tgggagatgg ccgacaacct ggccaaggaa      4980
aaccgagaat tcttcaacga cctggatctg ctcatggggc cggtcaccct gcacagcagc      5040
atggagcacc tggtccagta ctcccaacag ggcctgcact ggctgcggaa cagcgcccac      5100
ctgtcatag                                                            5109
```

```
<210> SEQ ID NO 25
<211> LENGTH: 3213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggtcagct ggggtcgttt catctgcctg gtcgtggtca ccatggcaac cttgtccctg        60
gcccggccct ccttcagttt agttgaggat accacattag agccagaaga gccaccaacc       120
aaataccaaa tctctcaacc agaagtgtac gtggctgcgc caggggagtc gctagaggtg       180
cgctgcctgt tgaaagatgc cgccgtgatc agttggacta aggatggggt gcacttgggg       240
cccaacaata ggacagtgct tattggggag tacttgcaga taaagggcgc cacgcctaga       300
gactccggcc tctatgcttg tactgccagt aggactgtag acagtgaaac ttggtacttc       360
atggtgaatg tcacagatgc catctcatcc ggagatgatg aggatgacac cgatggtgcg       420
gaagattttg tcagtgagaa cagtaacaac aagagagcac catactggac caacacagaa       480
aagatggaaa agcggctcca tgctgtgcct gcggccaaca ctgtcaagtt tcgctgccca       540
gccgggggga acccaatgcc aaccatgcgg tggctgaaaa acgggaagga gtttaagcag       600
gagcatcgca ttggaggcta caaggtacga aaccagcact ggagcctcat tatggaaagt       660
gtggtcccat ctgacaaggg aaattatacc tgtgtagtgg agaatgaata cgggtccatc       720
aatcacacgt accacctgga tgttgtggag cgatcgcctc accggcccat cctccaagcc       780
ggactgccgg caaatgcctc cacagtggtc ggaggagacg tagagtttgt ctgcaaggtt       840
tacagtgatg cccagcccca catccagtgg atcaagcacg tggaaaagaa cggcagtaaa       900
tacgggcccg acgggctgcc ctacctcaag gttctcaagg ccgccggtgt taacaccacg       960
gacaaagaga ttgaggttct ctatattcgg aatgtaactt ttgaggacgc tggggaatat      1020
```

-continued

```
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320 aacacccgc tggtgaggat aacaacacgc ctctcttcaa cggcagacac ccccatgctg   1380
gcaggggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgtttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaactttta agctgctgaa ggaaggacac   2160
agaatggata gccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gatggcagat gatcagggct gtattgaaga gcaggggtt   2340 gaggattcag caaatgaaga ttcagtggat gctaagccag accggtcctc gtttgtaccg   2400
tccctcttca gtaagaagaa gaaaaatgtc accatgcgat ccatcaagac cacccgggac   2460
cgagtgccta catatcagta caacatgaat tttgaaaagc tgggcaaatg catcataata   2520
aacaacaaga actttgataa agtgacaggt atgggcgttc gaaacggaac agacaaagat   2580
gccgaggcgc tcttcaagtg cttccgaagc ctgggttttg acgtgattgt ctataatgac   2640
tgctcttgtg ccaagatgca agatctgctt aaaaaagctt ctgaagagga ccatacaaat   2700
gccgcctgct cgcctgcat cctcttaagc catggagaag aaaatgtaat ttatgggaaa   2760
gatggtgtca caccaataaa ggatttgaca gcccacttta gggggggatag atgcaaaacc   2820 cttttagaga aacccaaact cttcttcatt caggcttgcc gagggaccga gcttgatgat   2880
ggcatccagg ccgactcggg gcccatcaat gacacagatg ctaatcctcg atacaagatc   2940
ccagtggaag ctgacttcct cttcgcctat tccacggttc caggctatta ctcgtggagg   3000
agcccaggaa gaggctcctg gtttgtgcaa gccctctgct ccatcctgga ggagcacgga   3060
aaagacctgg aaatcatgca gatcctcacc agggtgaatg acagagttgc caggcacttt   3120
gagtctcagt ctgatgaccc acacttccat gagaagaagc agatcccctg tgtggtctcc   3180
atgctcacca aggaactcta cttcagtcaa tag                                3213
```

<210> SEQ ID NO 26
<211> LENGTH: 3423
<212> TYPE: DNA

-continued

```
<213> ORGANISM: Artificial Sequence
<220> FEATURE:
<223> OTHER INFORMATION: Description of Artificial Sequence: Synthetic
      polynucleotide

<400> SEQUENCE: 26
atggtcagct ggggtcgttt catctgcctg gtcgtggtca ccatggcaac cttgtccctg        60
gcccggccct ccttcagttt agttgaggat accacattag agccagaaga gccaccaacc       120
aaataccaaa tctctcaacc agaagtgtac gtggctgcgc cagggagtc gctagaggtg         180 cgctgcctgt tgaaagatgc cgccgtgatc agttggacta aggatggggt gcacttgggg       240
cccaacaata ggacagtgct tattggggag tacttgcaga taaagggcgc cacgcctaga       300
gactccggcc tctatgcttg tactgccagt aggactgtag acagtgaaac ttggtacttc       360
atggtgaatg tcacagatgc catctcatcc ggagatgatg aggatgacac cgatggtgcg       420
gaagattttg tcagtgagaa cagtaacaac aagagagcac catactggac caacacagaa       480
aagatggaaa agcggctcca tgctgtgcct gcggccaaca ctgtcaagtt tcgctgccca       540
gccgggggga acccaatgcc aaccatgcgg tggctgaaaa acgggaagga gtttaagcag       600
gagcatcgca ttggaggcta caaggtacga aaccagcact ggagcctcat tatggaaagt       660
gtggtcccat ctgacaaggg aaattatacc tgtgtagtgg agaatgaata cgggtccatc       720
aatcacacgt accacctgga tgttgtggag cgatcgcctc accggcccat cctccaagcc       780
ggactgccgg caaatgcctc cacagtggtc ggaggagacg tagagtttgt ctgcaaggtt       840
tacagtgatg cccagcccca catccagtgg atcaagcacg tggaaaagaa cggcagtaaa       900
tacgggcccg acgggctgcc ctacctcaag gttctcaagg ccgccggtgt taacaccacg       960
gacaaagaga ttgaggttct ctatattcgg aatgtaactt ttgaggacgc tggggaatat      1020
acgtgcttgg cgggtaattc tattgggata tcctttcact ctgcatggtt gacagttctg      1080
ccagcgcctg gaagagaaaa ggagattaca gcttccccag actacctgga gatagccatt      1140
tactgcatag gggtcttctt aatcgcctgt atggtggtaa cagtcatcct gtgccgaatg      1200
aagaacacga ccaagaagcc agacttcagc agccagccgg ctgtgcacaa gctgaccaaa      1260
cgtatccccc tgcggagaca ggtaacagtt tcggctgagt ccagctcctc catgaactcc      1320 aacacccgc tggtgaggat aacaacacgc ctctcttcaa cggcagacac ccccatgctg      1380
gcaggggtct ccgagtatga acttccagag gacccaaaat gggagtttcc aagagataag      1440
ctgacactgg gcaagcccct gggagaaggt tgctttgggc aagtggtcat ggcggaagca      1500
gtgggaattg acaaagacaa gcccaaggag gcggtcaccg tggccgtgaa gatgttgaaa      1560
gatgatgcca cagagaaaga cctttctgat ctggtgtcag agatggagat gatgaagatg      1620
attgggaaac acaagaatat cataaatctt cttggagcct gcacacagga tgggcctctc      1680
tatgtcatag ttgagtatgc ctctaaaggc aacctccgag aatacctccg agcccggagg      1740
ccacccggga tggagtactc ctatgacatt aaccgtgttc ctgaggagca gatgaccttc      1800
aaggacttgg tgtcatgcac ctaccagctg gccagaggca tggagtactt ggcttcccaa      1860
aaatgtattc atcgagattt agcagccaga aatgttttgg taacagaaaa caatgtgatg      1920
aaaatagcag actttggact cgccagagat atcaacaata tagactatta caaaaagacc      1980
accaatgggc ggcttccagt caagtggatg gctccagaag ccctgtttga tagagtatac      2040
actcatcaga gtgatgtctg gtccttcggg gtgttaatgt gggagatctt cactttaggg      2100
ggctcgccct acccagggat tcccgtggag gaacttttta agctgctgaa ggaaggacac      2160
```

-continued

```
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga gcaagccagg gctgagcagg aagaagaatt cattagtaac    2340
actttattca agaaaattca ggctttgcag aaggagaaag aaacccttgc tgtaaattat    2400
gagaaagaag aagaattcct cactaatgag ctctccagaa aattgatgca gttgcagcat    2460
gagaaagccg aactagaaca gcatcttgaa caagagcagg aatttcaggt caacaaactg    2520
atgaagaaaa ttaaaaaact ggagaatgac accatttcta agcaacttac attagaacag    2580
ttgagacggg agaagattga ccttgaaaat acattggaac aagaacaaga agcactagtt    2640
aatcgcctct ggaaaaggat ggataagctt gaagctgaaa agcgaatcct gcaggaaaaa    2700
ttagaccagc ccgtctctgc tccaccatcg cctagagata tctccatgga gattgattct    2760
ccagaaaata tgatgcgtca catcaggttt ttaaagaatg aagtggaacg gctgaagaag    2820
caactgagag ctgctcagtt acagcattca gagaaatgg cacagtatct ggaggaggaa    2880
cgtcacatga gagaagagaa cttgaggctc cagaggaagc tgcagaggga gatggagaga    2940
agagaagccc tctgtcgaca gctctccgag agtgagtcca gcttagaaat ggacgacgaa    3000
aggtatttta atgagatgtc tgcacaagga ttaagacctc gcactgtgtc cagcccgatc    3060
ccttacacac cttctccgag ttcaagcagg cctatatcac ctggtctatc atatgcaagt    3120
cacacggttg gtttcacgcc accaacttca ctgactagct ctggaatgtc ttattacaat    3180
tccccgggtc ttcacgtgca gcacatggga acatcccatg gtatcacaag gccttcacca    3240
cggagaagca acagtcctga caaattcaaa cggcccacgc cgcctccatc tcccaacaca    3300
cagaccccag tccagccacc tccgcctcca cctccgccac ccatgcagcc cacggtcccc    3360
tcagcagcca cctcgcagcc tactccttcg caacattcgg cgcacccctc ctcccagcct    3420
taa                                                                  3423
```

<210> SEQ ID NO 27
<211> LENGTH: 5229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atggtcagct ggggtcgttt catctgcctg gtcgtggtca ccatggcaac cttgtccctg     60
gcccggccct ccttcagttt agttgaggat accacattag agccagaaga gccaccaacc    120
aaataccaaa tctctcaacc agaagtgtac gtggctgcgc caggggagtc gctagaggtg    180
cgctgcctgt tgaaagatgc cgccgtgatc agttggacta aggatggggt gcacttgggg    240
cccaacaata ggacagtgct tattggggag tacttgcaga taaagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420 gaagatttg tcagtgagaa cagtaacaac aagagagcac atactggac caacacagaa    480 aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttgaggctca aaggtacga aaccagcact ggagcctcat tatggaaagt    660
gtggtcccat ctgacaaggg aaattatacc tgtgtagtgg agaatgaata cgggtccatc    720
```

-continued

```
aatcacacgt accacctgga tgttgtggag cgatcgcctc accggcccat cctccaagcc   780
ggactgccgg caaatgcctc cacagtggtc ggaggagacg tagagtttgt ctgcaaggtt   840
tacagtgatg cccagcccca catccagtgg atcaagcacg tggaaaagaa cggcagtaaa   900
tacgggcccg acgggctgcc ctacctcaag gttctcaagg ccgccggtgt taacaccacg   960
gacaaagaga ttgaggttct ctatattcgg aatgtaactt ttgaggacgc tggggaatat  1020
acgtgcttgg cgggtaattc tattgggata tcctttcact ctgcatggtt gacagttctg  1080
ccagcgcctg gaagagaaaa ggagattaca gcttccccag actacctgga gatagccatt  1140
tactgcatag gggtcttctt aatcgcctgt atggtggtaa cagtcatcct gtgccgaatg  1200
aagaacacga ccaagaagcc agacttcagc agccagccgg ctgtgcacaa gctgaccaaa  1260
cgtatccccc tgcggagaca ggtaacagtt tcggctgagt ccagctcctc catgaactcc  1320
aacaccccgc tggtgaggat aacaacacgc ctctcttcaa cggcagacac ccccatgctg  1380
gcaggggtct ccgagtatga acttccagag acccaaaat gggagtttcc aagagataag  1440
ctgacactgg gcaagcccct gggagaaggt tgctttgggc aagtggtcat ggcggaagca  1500
gtgggaattg acaaagacaa gcccaaggag gcggtcaccg tggccgtgaa gatgttgaaa  1560
gatgatgcca cagagaaaga cctttctgat ctggtgtcag agatggagat gatgaagatg  1620
attgggaaac acaagaatat cataaatctt cttggagcct gcacacagga tgggcctctc  1680
tatgtcatag ttgagtatgc ctctaaaggc aacctccgag aatacctccg agcccggagg  1740
ccacccggga tggagtactc ctatgacatt aaccgtgttc ctgaggagca gatgaccttc  1800
aaggacttgg tgtcatgcac ctaccagctg gccagaggca tggagtactt ggcttcccaa  1860
aaatgtattc atcgagattt agcagccaga aatgtttttgg taacagaaaa caatgtgatg  1920
aaaatagcag actttggact cgccagagat atcaacaata tagactatta caaaaagacc  1980
accaatgggc ggcttccagt caagtggatg gctccagaag ccctgtttga tagagtatac  2040
actcatcaga gtgatgtctg gtccttcggg gtgttaatgt gggagatctt cactttaggg  2100
ggctcgccct acccagggat tcccgtggag gaactttta agctgctgaa ggaaggacac  2160
agaatggata agccagccaa ctgcaccaac gaactgtaca tgatgatgag ggactgttgg  2220
catgcagtgc cctcccagag accaacgttc aagcagttgg tagaagactt ggatcgaatt  2280
ctcactctca caaccaatga gacacaactt cgaaaccagc taattcatga gttgatgcac  2340
cctgtattga gtggagaact gcagcctcgg tccatttcag tagaagggag ctccctctta  2400
ataggcgcct ctaactcttt agtggcagat cacttacaaa gatgtggcta tgaatattca  2460
ctttctgttt tctttccaga aagtggtttg gcaaagaaa aggtatttac tatgcaggat  2520
ctattacaac tcattaaaat caaccctact tccagtctct acaaatcact ggtttcagga  2580
tctgataaag aaaatcaaaa aggttttctt atgcattttt taaaagaatt ggcagaatat  2640
catcaagcta aagagagttg taatatggaa actcagacaa gttcgacatt taacagagat  2700
tctctggctg agaagcttca gcttattgat gatcagtttg cagatgctta ccctcagcgt  2760
atcaagttcg aatctttaga aataaagcta aatgagtata agagagaaat agaagagcaa  2820
cttcgggcag aaatgtgtca aaagttgaag ttttttaaag ataccgagat agcaaaaatt  2880
aaaatggaag caaaaaaaaa gtatgaaaag gagttaacca tgttccagaa tgattttgaa  2940
aaagcttgtc aagcaaatc tgaagctctc gttcttcggg aaaagagtac ccttgaaaga  3000
attcacaagc accaagagat tgaaacaaaa gaaatttatg ctcaaaggca acttttacta  3060
aaagatatgg atttgctaag aggaagagaa gcagagctga agcaaagagt tgaagctttt  3120
```

```
gaattgaacc agaagctcca ggaagaaaaa cataaaagca taactgaggc acttaggaga    3180
caggagcaga atataaagag ttttgaggag acctatgacc gaaagctcaa gaatgaactt    3240
ctaaagtatc aacttgaact gaaggatgac tacatcatta gaactaatcg actgattgaa    3300
gatgaaagga agaataaaga aaaagctgtt catttgcaag aggagctcat agctattaat    3360
tcaaaaaagg aggaactcaa tcaatctgta aatcgtgtga aagaacttga gcttgaatta    3420
gagtctgtca aagcccagtc tttggcaata acaaaacaaa accatatgct gaatgaaaag    3480
gttaaagaga tgagtgatta ttcactacta aaagaagaga aactggagct tctggcacaa    3540
aataaattac ttaaacaaca actggaagag agtagaaatg aaaacctgcg tctcctaaac    3600
cgcctagctc agccggctcc tgaacttgca gtctttcaga aagaactacg gaaagccgaa    3660
aaggctatag tggttgagca tgaggagttc gaaagctgca ggcaagctct gcacaaacaa    3720
ctgcaagacg aaattgagca ttctgcacag ctgaaggccc agattctagg ttacaaagct    3780
tctgtaaaga gtttaactac tcaggttgcc gatttaaaat tgcaactgaa gcaaactcag    3840
acagccctag agaatgaagt gtactgcaat ccaaagcagt ctgtgatcga tcgttctgtc    3900
aatggattaa taaatggcaa tgtggtgcct tgcaatggtg agataagtgg ggatttcttg    3960
aacaatcctt ttaaacagga aaacgttcta gcacgtatgg ttgcatcaag gatcacaaat    4020
tatccaactg catgggtgga gggtagttcc cctgattctg accttgagtt tgtagccaat    4080
actaaggcaa gggtcaaaga gcttcagcaa gaggccgaac gcttggaaaa ggctttcaga    4140
agttaccatc ggagagtcat taaaaactct gccaaaagcc cactagcagc aaagagccca    4200
ccatctctgc acttgctgga agccttcaaa aacattactt ccagttcccc ggaaagacat    4260
atttttggag aggacagagt tgtctctgag cagcctcaag tgggcacact tgaagaaagg    4320
aatgacgtcg tggaagcact gacaggcagt gcagcctcga ggctccgcgg gggcacttcc    4380
tccagacgcc tctcttccac accccttcca aaagcaaaaa gaagcctcga aagtgaaatg    4440
tatctggaag gtctgggcag atcacacatt gcttcccca gtccttgtcc tgacagaatg    4500
cccctaccat cacccactga gtctaggcac agcctctcca tccctcctgt ctccagccct    4560
ccggagcaga aagtgggtct ttatcgaaga caaactgaac ttcaagacaa aagtgaattt    4620
tcagatgtgg acaagctagc ttttaaggat aatgaggagt ttgaatcatc ttttgaatct    4680
gcagggaaca tgccaaggca gttggaaatg ggcgggcttt ctcctgccgg ggatatgtct    4740
catgtggacg ctgctgcagc tgctgtgccc ctctcatatc agcacccaag tgtagatcag    4800
aaacaaattg aagaacaaaa ggaagaagaa aaaatacggg aacagcaagt gaaagaacga    4860
aggcagagag aagaaagaag gcagagtaac ctacaagaag ttttagaaag ggaacgaaga    4920
gaactagaaa aactgtatca ggaaaggaag atgattgaag aatcactgaa gattaaaata    4980
aaaaaggaat tagaaatgga aaatgaatta gaaatgagta atcaagaaat aaaagacaaa    5040
tctgctcaca gtgaaaatcc tttagagaaa tacatgaaaa tcatccagca ggagcaagac    5100
caggagtcgg cagataagag ctcaaaaaag atggtccaag aaggctccct agtggacacg    5160
ctgcaatcta gtgacaaagt cgaaagttta acaggctttt ctcatgaaga actagacgac    5220
tcttggtaa                                                           5229
```

FGFR/PD-1 COMBINATION THERAPY FOR THE TREATMENT OF CANCER

CROSS REFERENCE TO RELATED APPLICATIONS

This application is a continuation of U.S. application Ser. No. 16/661,671, filed Oct. 23, 2019, which is a continuation of U.S. application Ser. No. 15/079,136, filed on Mar. 24, 2016 (which issued as U.S. Pat. No. 10,478,494), which claims priority to U.S. Provisional Application No. 62/142, 569, filed on Apr. 3, 2015. The entire disclosure of each of the previous applications are hereby incorporated by reference herein.

SEQUENCE LISTING

The instant application contains a Sequence Listing which has been submitted electronically in ASCII format and is hereby incorporated by reference in its entirety. Said ASCII copy, created on Mar. 22, 2016, is named PRD3366USNP_SL.txt and is 53,086 bytes in size.

TECHNICAL FIELD

Provided herein are combination therapies for the treatment of cancer. In particular, the disclosed methods are directed to treatment of cancer in a patient comprising administering an antibody that blocks the interaction between PD-1 and PD-L1 and a fibroblast growth factor receptor (FGFR) inhibitor.

BACKGROUND

For cancer patients failing the main therapeutic option (front-line therapy) for that cancer type, there is often no accepted standard of care for second and subsequent-line therapy, unless a particular genetic abnormality is identified and a specific therapy is available. Fibroblast growth factor receptors (FGFRs) are a family of receptor tyrosine kinases involved in regulating cell survival, proliferation, migration and differentiation. FGFR alterations have been observed in some cancers. To date, there are no approved therapies that are efficacious in patients with FGFR alterations.

SUMMARY

Disclosed herein are methods of using a combination therapy comprising an antibody that blocks the interaction between PD-1 and PD-L1 and an FGFR inhibitor to treat cancer in the patient. In some embodiments, the methods comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if one or more FGFR variants are present in a biological sample from the patient.

In other embodiments, the methods of treating cancer in a patient comprise: administering to the patient a pharmaceutically effective amount of an antibody that blocks the interaction between PD-1 and PD-L1; monitoring the efficacy of the antibody; and, if the antibody is not efficacious, evaluating a biological sample from the patient for a presence of one or more FGFR variants and administering to the patient a pharmaceutically effective amount of an FGFR inhibitor if the one or more FGFR variants are present in the sample.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings.

DETAILED DESCRIPTION OF ILLUSTRATIVE EMBODIMENTS

Figure 1:
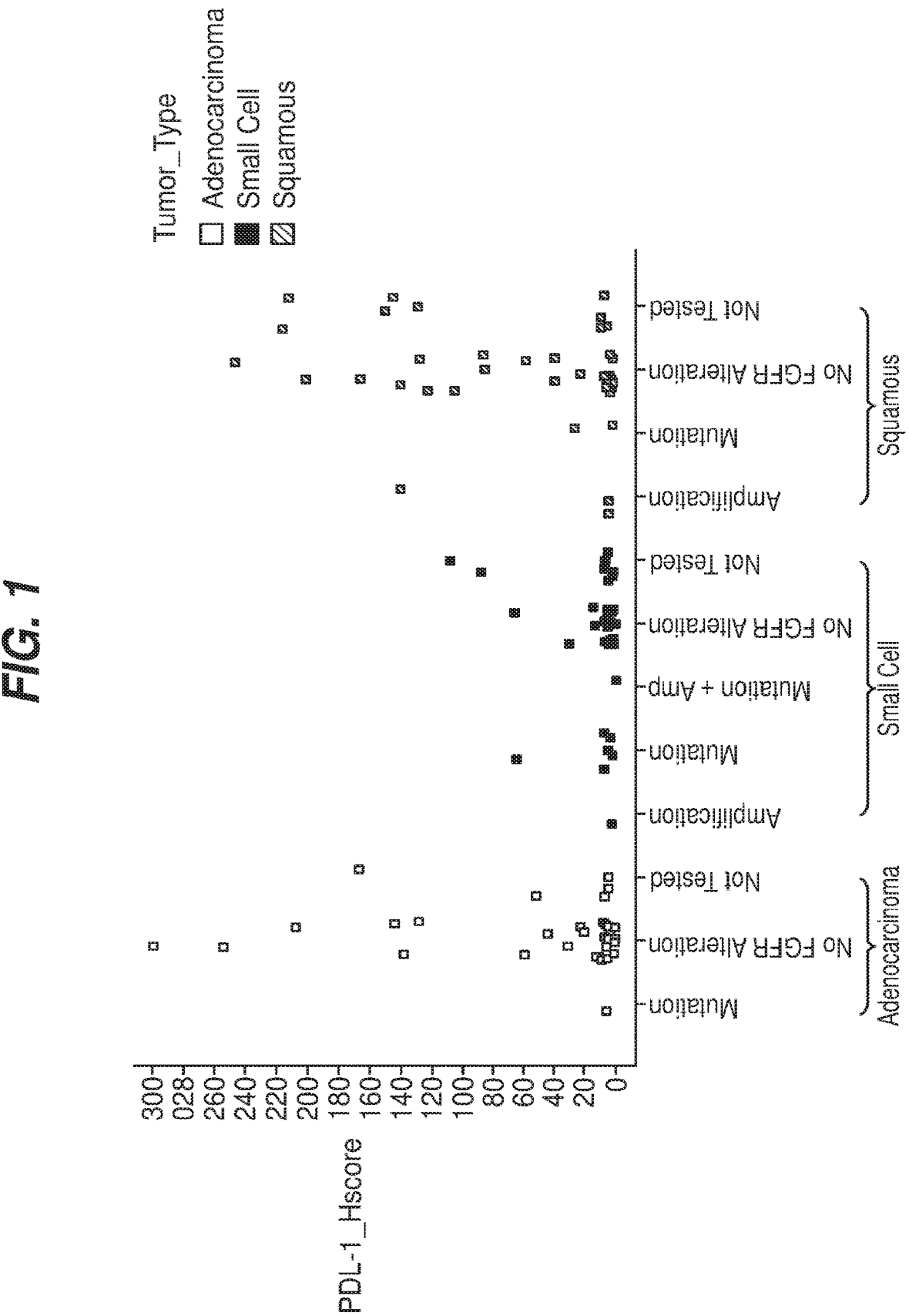
FIG. 1 illustrates PD-L1 expression in a 120 lung cancer samples set by histology and FGFR mutant and amplification status. PD-L1 H-scores (Y-axis) were plotted for NSCLC adenocarcinoma (left), small cell lung cancer (middle), and NSCLC squamous (right). The FGFR mutation and/or amplification status versus the PD-L1 staining for each of the 120 samples is shown. Mutation—an FGFR mutation was identified; No FGFR Alteration—no mutation or fusion was detected; Amplification—an FGFR gene amplification was identified; Mutation+Amp—samples positive for both FGFR mutation and gene amplification; Not Tested—IHC for PD-L1 was performed, but sample was not tested on Foundation Medicine panel.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

The following abbreviations are used throughout the disclosure: FFPE (formalin-fixed, paraffin-embedded); NSCLC (non-small-cell lung carcinoma); SCLC (small-cell lung cancer); FGFR (fibroblast growth factor receptor); PD-1 (programmed cell death 1); PD-L1 (programmed death-ligand 1); FGFR3:TACC3 (fusion between genes encoding FGFR3 and transforming acidic coiled-coil containing protein); FGFR3:BAIAP2L1 (fusion between genes encoding FGFR3 and brain-specific angiogenesis inhibitor 1-associated protein 2-like protein 1); FGFR2:AFF3 (fusion between genes encoding FGFR2 and AF4/FMR2 family, member 3); FGFR2:BICC1 (fusion between genes encoding FGFR2 and bicaudal C homolog 1); FGFR2: CASP7 (fusion between genes encoding FGFR2 and caspase 7); FGFR2: CCDC6 (fusion between genes encoding FGFR2 and coiled-coil domain containing 6); FGFR2:OFD1 (fusion between genes encoding FGFR2 and oral-facial-digital syndrome 1).

The term "antibody" refers to (a) immunoglobulin polypeptides, i.e., polypeptides of the immunoglobulin family that contain an antigen binding site that specifically binds to a specific antigen (e.g., PD-1 or PD-L1), including all immunoglobulin isotypes (IgG, IgA, IgE, IgM, IgD, and IgY), classes (e.g. IgG1, IgG2, IgG3, IgG4, IgA1, IgA2), subclasses, and various monomeric and polymeric forms of each isotype, unless otherwise specified, and (b) conservatively substituted variants of such immunoglobulin polypeptides that immunospecifically bind to the antigen (e.g., PD-1 or PD-L1). Antibodies are generally described in, for example, Harlow & Lane, Antibodies: A Laboratory Manual (Cold Spring Harbor Laboratory Press, 1988). Unless otherwise apparent from the context, reference to an antibody also includes antibody derivatives as described in more detail below.

"Antibody fragments" comprise a portion of a full length antibody, generally the antigen-binding or variable region thereof, such as Fab, Fab', F(ab')₂, and Fv fragments; diabodies; linear antibodies; single-chain antibody molecules; and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

An "antibody derivative" means an antibody, as defined above, that is modified by covalent attachment of a heterologous molecule such as, e.g., by attachment of a heterologous polypeptide (e.g., a cytotoxin) or therapeutic agent (e.g., a chemotherapeutic agent), or by glycosylation, deglycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

"Biological sample" refers to any sample from a patient in which cancerous cells can be obtained and protein expression can be evaluated and/or RNA can be isolated. Suitable biological samples include, but are not limited to, blood, lymph fluid, bone marrow, sputum, a solid tumor sample, or any combination thereof. In some embodiments, the biological sample can be formalin-fixed paraffin-embedded tissue (FFPET).

As used here, "block(s) the interaction" refers to the ability of an anti-PD-1 antibody or an anti-PD-L1 antibody to inhibit or reduce binding of PD-L1 to PD-1, such that signaling/functioning through PD-1 is abolished or diminished.

As used herein, "FGFR variant" refers to an alteration in the wild type FGFR gene, including, but not limited to, FGFR fusion genes, FGFR mutations (e.g., FGFR3 R248C, FGFR3 S249C, FGFR3 G370C, or FGFR3 Y373C), FGFR amplifications, or any combination thereof. "FGFR fusion" or "FGFR fusion gene" refers to a gene encoding a portion of FGFR (e.g., FGRF2 or FGFR3) and one of the herein disclosed fusion partners created by a translocation between the two genes.

As used herein, "patient" is intended to mean any animal, in particular, mammals. Thus, the methods are applicable to human and nonhuman animals, although most preferably with humans. "Patient" and "subject" may be used interchangeably herein.

"Pharmaceutically effective amount" refers to an amount of an antibody that blocks the interaction between PD-1 and PD-L1 and an amount of an FGFR inhibitor that treats the patient.

As used herein, "treating" and like terms refer to reducing the severity and/or frequency of cancer symptoms, eliminating cancer symptoms and/or the underlying cause of said symptoms, reducing the frequency or likelihood of cancer symptoms and/or their underlying cause, and improving or remediating damage caused, directly or indirectly, by cancer.

Disclosed herein are methods of treating cancer in a patient comprising: administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if one or more FGFR variants are present in a biological sample from the patient.

PD-1 is a cell surface receptor expressed on the surface of CD4+ and CD8+ T cells, B cells, and myeloid cells. The ligands of PD-1, PD-L1 and PD-L2, are expressed on immune cells; in addition, PD-L1 is also expressed on cancer cells. When engaged by its ligands, PD-1 downregulates the immune response by reducing T cell proliferation, cytokine production and effector function. Antibodies against PD-1 (anti-PD-1 antibodies) and/or its ligands (anti-PD-L1 antibodies, for example) can block the interaction between PD-1 and PD-L1, thereby inhibiting the downregulation of the immune response. The disclosed methods comprise administering to the patient a pharmaceutically effective amount of an antibody that blocks the interaction between PD-1 and PD-L1. In some embodiments, the methods can comprise administering to the patient a pharmaceutically effective amount of an anti-PD-1 antibody. In some embodiments, the methods can comprise administering to the patient a pharmaceutically effective amount of an anti-PD-L1 antibody. In some embodiments, the methods can comprise administering to the patient a pharmaceutically effective amount of an anti-PD-1 antibody and an anti-PD-L1 antibody.

Exemplary anti-PD-1 antibodies include, but are not limited to, OPDIVO® (nivolumab) (Bristol-Myers Squibb) and KEYTRUDA® (pembrolizumab) (Merck). Exemplary anti-PD-L1 antibodies include, but are not limited to, MPDL3208A (Roche) and MEDI4736 (AstraZeneca).

Exemplary FGFR inhibitors are described in U.S. Publ. No. 2013/0072457 A1 (incorporated herein by reference) and include N-(3,5-dimethoxyphenyl)-N'-(1-methylethyl)-N-[3-(1-methyl-1H-pyrazol-4-yl)quinoxalin-6-yl]ethane-1,2-diamine (referred to herein "JNJ-42756493"), including any tautomeric or stereochemically isomeric forms thereof, N-oxides thereof, pharmaceutically acceptable salts thereof, or solvates thereof (suitable R groups are also disclosed in U.S. Publ. No. 2013/0072457 A1). Thus, in some embodiments, the FGFR inhibitor can be the compound of formula (I):

6

(I)

or a pharmaceutically acceptable salt thereof. In some aspects, the pharmaceutically acceptable salt is a HCl salt.

The antibody that blocks the interaction between PD-1 and PD-L1 and the FGFR inhibitor can be administered as a single therapeutic agent or can be co-administered as individual agents. When administered as individual agents, the antibody and FGFR inhibitor can be administered contemporaneously or sequentially in either order. In some embodiments, the antibody that blocks the interaction between PD-1 and PD-L1 and the FGFR inhibitor can be administered contemporaneously. In some embodiments, the antibody that blocks the interaction between PD-1 and PD-L1 can be administered sequentially. In some aspects, for example, the antibody that blocks the interaction between PD-1 and PD-L1 can be administered first, followed by administration of the FGFR inhibitor. In other aspects, the FGFR inhibitor can be administered first, followed by administration of the antibody that blocks the interaction between PD-1 and PD-L1. When administered sequentially, the antibody and FGFR inhibitor can be administered within seconds, minutes, hours, days, or weeks of each other.

The pharmaceutically effective amount of the antibody that blocks the interaction between PD-1 and PD-L1 and FGFR inhibitor will be dependent on several factors including, but not limited to, stage and severity of the cancer, as well as other factors relating to the health of the patient. Those skilled in the art would know how to determine the pharmaceutically effective amount.

The disclosed methods are suitable for treating cancer in a patient if one or more FGFR variants are present in a biological sample from the patient. In some embodiments, the FGFR variant can be one or more FGFR fusion genes. In some embodiments, the FGFR variant can be one or more FGFR mutations. In some embodiments, the FGFR variant can be one or more FGFR amplifications. In some embodiments, a combination of the one or more FGFR variants can be present in the biological sample from the patient. For example, in some embodiments, the FGFR variants can be one or more FGFR fusion genes and one or more FGFR mutations. In some embodiments, the FGFR variants can be one or more FGFR fusion genes and one or more FGFR amplifications. In some embodiments, the FGFR variants can be one or more FGFR mutations and one or more FGFR amplifications. In yet other embodiments, the FGFR variants can be one or more FGFR fusion genes, mutations, and amplifications.

Exemplary FGFR fusion genes are provided in Table 1 and include, but are not limited to: FGFR2:AFF3; FGFR2:BICC1; FGFR2:CASP7; FGFR2:CCDC6; FGFR2:OFD1; FGFR3:BAIAP2L1; FGFR3:TACC3-Intron; FGFR3:

TACC3V1; FGFR3:TACC3V3; or a combination thereof. The sequences of the FGFR fusion genes are disclosed in Table 6.

TABLE 1

Exemplary FGFR fusion genes

| Fusion Gene | FGFR Exon | Partner Exon |
|---|---|---|
| FGFR2 | | |
| FGFR2:AFF3 | 19 | 8 |
| FGFR2:BICC1 | 19 | 3 |
| FGFR2:CASP7 | 19 | 4 |
| FGFR2:CCDC6 | 19 | 2 |
| FGFR2:OFD1 | 19 | 3 |
| FGFR3 | | |
| FGFR3:BAIAP2L1 | 18 | 2 |
| FGFR3:TACC3 Intron | 18 | 4 |
| FGFR3:TACC3 v1 | 18 | 11 |
| FCFR3:TACC3 v3 | 18 | 10 |

The methods can further comprise evaluating the presence of one or more FGFR variants in the biological sample before the administering step. Suitable methods for evaluating a biological sample for the presence of one or more FGFR variants are disclosed elsewhere herein.

The disclosed methods can be dependent upon PD-L1 expression in the cancer or can be carried out irrespectively of PD-L1 expression in the cancer. In some embodiments, for example, the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if one or more FGFR variants are present in a biological sample from the patient and PD-L1 expression in the biological sample from the patient is at a specified level or within a specified range. In some aspects, for example, the methods can be carried out if the PD-L1 expression is high in the biological sample. Accordingly, in some embodiments the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if PD-L1 expression is high and one or more FGFR variants are present in a biological sample from the patient. Alternatively, the methods can be carried out if the PD-L1 expression is low in the biological sample. Accordingly, the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if PD-L1 expression is low and one or more FGFR variants are present in a biological sample from the patient. The methods can be carried out if the PD-L1 expression is moderate. Accordingly, the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if PD-L1 expression is moderate and one or more FGFR variants are present in a biological sample from the patient. As discussed elsewhere herein, PD-L1 expression levels can be based upon a numerical H-score (low includes an H-score of about 0 to about 99; moderate includes an H-score of about 100 to about 199; and high includes an H-score of about 200 to about 300) or can be based upon a comparison to a reference value.

In other embodiments, the methods can be carried out irrespectively of PD-L1 expression in the biological sample from the patient and can be based on the presence of one or more FGFR variants without factoring in PD-L1 expression.

The methods can further comprise evaluating PD-L1 expression in the biological sample from the patient. Exemplary methods of evaluating PD-L1 expression are disclosed elsewhere herein. PD-L1 expression can be evaluated before, during, or after the administering step.

In some embodiments, the methods can comprise evaluating the presence of one or more FGFR variants and PD-L1 expression in the biological sample from the patient before the administering step.

Suitable biological samples evaluating PD-L1 expression, evaluating the presence of one or more FGFR variants, or for evaluating both PD-L1 expression and the presence of one or more FGFR variants include, but are not limited to, blood, lymph fluid, bone marrow, a solid tumor sample, or any combination thereof.

The disclosed methods can be used to treat a variety of cancer types including, but not limited to, lung cancer, bladder cancer, gastric cancer, breast cancer, ovarian cancer, head and neck cancer, esophageal cancer, glioblastoma, or any combination thereof. In some embodiments, the methods can be used to treat lung cancer. The lung cancer can be non-small cell lung cancer (NSCLC) adenocarcinoma, NSCLC squamous cell carcinoma, small cell lung cancer, or any combination thereof. Thus, in some aspects, the methods can be used to treat NSCLC adenocarcinoma. In other aspects, the methods can be used to treat NSCLC squamous cell carcinoma. In yet other aspects, the methods can be used to treat small cell lung cancer. In some embodiments, the methods can be used to treat bladder cancer. In some embodiments, the methods can be used to treat gastric cancer. In some embodiments, the methods can be used to treat breast cancer. In some embodiments, the methods can be used to treat ovarian cancer. In some embodiments, the methods can be used to treat head and neck cancer. In some embodiments, the methods can be used to treat esophageal cancer. In some embodiments, the methods can be used to treat glioblastoma. In some embodiments, the methods can be used to treat any combination of the above cancers.

Also disclosed are methods of treating cancer in a patient comprising: administering to the patient a pharmaceutically effective amount of an antibody that blocks the interaction between PD-1 and PD-L1; monitoring the efficacy of the antibody; and if the antibody is not efficacious, evaluating a biological sample from the patient for a presence of one or more FGFR variants and administering to the patient a pharmaceutically effective amount of an FGFR inhibitor if the one or more FGFR variants are present in the sample.

The efficacy of the antibody can be monitored by, for example, evaluating the patient's symptoms for progression of the cancer, evaluating the severity of the cancer symptoms, evaluating the frequency of the cancer symptoms, measuring tumor size, or any combination thereof. Without intent to be limiting, progression or failure to reduce the progression of the cancer, increased severity or no change in severity of the cancer symptoms, increased frequency or no change in the frequency of the cancer symptoms, increased size or no change in size of the tumor, or any combination thereof, can be indications that the antibody is not efficacious.

In some embodiments, the methods can comprise administering to the patient a pharmaceutically effective amount of an anti-PD-1 antibody. In some embodiments, the methods can comprise administering to the patient a pharmaceutically effective amount of an anti-PD-L1 antibody. In some embodiments, the methods can comprise administering to the patient a pharmaceutically effective amount of an anti-PD-1 antibody and an anti-PD-L1 antibody. Exemplary anti-PD-1 antibodies include, but are not limited to, OPDIVO® (nivolumab) (Bristol-Myers Squibb) and KEYTRUDA® (pembrolizumab) (Merck). Exemplary anti-PD-L1 antibodies include, but are not limited to, MPDL3208A (Roche) and MEDI4736 (AstraZeneca).

Exemplary FGFR inhibitors include those disclosed above, including N-(3,5-dimethoxyphenyl)-N'-(1-methyl-ethyl)-N-[3-(1-methyl-1H-pyrazol-4-yl)quinoxalin-6-yl] ethane-1,2-diamine (referred to herein "JNJ-42756493"), including any tautomeric or stereochemically isomeric forms thereof, N-oxides thereof, pharmaceutically acceptable salts thereof, or solvates thereof (suitable R groups are also disclosed in U.S. Publ. No. 2013/0072457 A1). In some embodiments, the FGFR inhibitor can be the compound of formula (I):

(I)

or a pharmaceutically acceptable salt thereof. In some aspects, the pharmaceutically acceptable salt is a HCl salt.

The pharmaceutically effective amount of the antibody and FGFR inhibitor will be dependent on several factors including, but not limited to, stage and severity of the cancer, as well as other factors relating to the health of the patient. Those skilled in the art would know how to determine the pharmaceutically effective amount.

The disclosed methods are suitable for treating cancer in a patient if one or more FGFR variants are present in a biological sample from the patient. In some embodiments, the FGFR variant can be one or more FGFR fusion genes. In some embodiments, the FGFR variant can be one or more FGFR mutations. In some embodiments, the FGFR variant can be one or more FGFR amplifications. In some embodiments, a combination of the one or more FGFR variants can be present in the biological sample from the patient. For example, in some embodiments, the FGFR variants can be one or more FGFR fusion genes and one or more FGFR mutations. In some embodiments, the FGFR variants can be one or more FGFR fusion genes and one or more FGFR amplifications. In some embodiments, the FGFR variants can be one or more FGFR mutations and one or more FGFR amplifications. In yet other embodiments, the FGFR variants can be one or more FGFR fusion genes, mutations, and amplifications. Exemplary FGFR fusion genes are provided in Table 1 and include, but are not limited to: FGFR2:AFF3; FGFR2:BICC1; FGFR2:CASP7; FGFR2:CCDC6; FGFR2: OFD1; FGFR3:BAIAP2L1; FGFR3:TACC3-Intron; FGFR3:TACC3V1; FGFR3:TACC3V3; or a combination thereof.

Suitable methods for evaluating a biological sample for the presence of one or more FGFR variants are disclosed elsewhere herein.

The disclosed methods can be dependent upon PD-L1 expression in the biological sample or can be carried out irrespectively of PD-L1 expression in the cancer. In some aspects, for example, if the antibody is not efficacious, the methods can comprise measuring an expression level of PD-L1 in the biological sample and administering to the patient a pharmaceutically effective amount of an FGFR inhibitor if the PD-L1 expression is at a specified level or within a specified range. Methods of evaluating PD-L1 expression are disclosed elsewhere herein. The methods can be carried out if the PD-1 expression in the biological sample is low. In some embodiments, for example, the evaluating step can further comprise measuring an expression level of PD-L1 in the biological sample and the second administering step can comprise administering the FGFR inhibitor if the expression level of PD-L1 is low. In some aspects, methods of treating cancer in a patient comprise: administering to the patient a pharmaceutically effective amount of an antibody that blocks the interaction between PD-1 and PD-L1; monitoring the efficacy of the antibody; and if the antibody is not efficacious, evaluating a biological sample from the patient for a presence of one or more FGFR variants and measuring an expression level of PD-L1 in the biological sample, and administering to the patient a pharmaceutically effective amount of an FGFR inhibitor if the one or more FGFR variants are present and if the expression level of PD-L1 is low in the sample.

The methods can be carried out if the PD-1 expression in the biological sample is moderate. Thus, the evaluating step can further comprise measuring an expression level of PD-L1 in the biological sample and the second administering step can comprise administering the FGFR inhibitor if the expression level of PD-L1 is moderate. The methods can be carried out if the PD-1 expression in the biological sample is high. For example, the evaluating step can further comprise measuring an expression level of PD-L1 in the biological sample and the second administering step can comprise administering the FGFR inhibitor if the expression level of PD-L1 is high.

As discussed elsewhere herein, PD-L1 expression levels can be based upon a numerical H-score (low includes an H-score of about 0 to about 99; moderate includes an H-score of about 100 to about 199; and high includes an H-score of about 200 to about 300) or can be based upon a comparison to a reference value.

In other embodiments, the methods can be carried out irrespectively of PD-L1 expression in the cancer and can be based on the presence of one or more FGFR variants in the biological sample without factoring in PD-L1 expression.

Suitable biological samples include, but are not limited to, blood, lymph fluid, bone marrow, a solid tumor sample, or any combination thereof.

The disclosed methods can be used to treat a variety of cancer types including, but not limited to, lung cancer, bladder cancer, gastric cancer, breast cancer, ovarian cancer, head and neck cancer, esophageal cancer, glioblastoma, or any combination thereof. In some embodiments, the methods can be used to treat lung cancer. The lung cancer can be non-small cell lung cancer (NSCLC) adenocarcinoma, NSCLC squamous cell carcinoma, small cell lung cancer, or any combination thereof. Thus, in some aspects, the methods can be used to treat NSCLC adenocarcinoma. In other aspects, the methods can be used to treat NSCLC squamous cell carcinoma. In yet other aspects, the methods can be used to treat small cell lung cancer. In some embodiments, the methods can be used to treat bladder cancer. In some embodiments, the methods can be used to treat gastric cancer. In some embodiments, the methods can be used to treat breast cancer. In some embodiments, the methods can be used to treat ovarian cancer. In some embodiments, the methods can be used to treat head and neck cancer. In some embodiments, the methods can be used to treat esophageal cancer. In some embodiments, the methods can be used to treat glioblastoma. In some embodiments, the methods can be used to treat any combination of the above cancers.

Evaluating a Sample for the Presence of One or More FGFR Variants

The following methods for evaluating a biological sample for the presence of one or more FGFR variants apply equally to any of the above disclosed methods of treatment.

Suitable methods for evaluating a biological sample for the presence of one or more FGFR variants are described in the methods section herein and in U.S. Provisional Patent App. No. 62/056,159, which is incorporated herein in its entirety. For example, and without intent to be limiting, evaluating a biological sample for the presence of one or more FGFR variants can comprise any combination of the following steps: isolating RNA from the biological sample; synthesizing cDNA from the RNA; and amplifying the cDNA (preamplified or non-preamplified). In some embodiments, evaluating a biological sample for the presence of one or more FGFR variants can comprise: amplifying cDNA from the patient with a pair of primers that bind to and amplify one or more FGFR variants; and determining whether the one or more FGFR variants are present in the sample. In some aspects, the cDNA can be pre-amplified. In some aspects, the evaluating step can comprise isolating RNA from the sample, synthesizing cDNA from the isolated RNA, and pre-amplifying the cDNA.

Suitable primer pairs for performing an amplification step include, but are not limited to, those disclosed in U.S. Provisional Patent App. No. 62/056,159, as exemplified below:

```
FGFR3TACC3 V1
Forward:
                                        (SEQ ID NO: 1)
GACCTGGACCGTGTCCTTACC Reverse:
                                        (SEQ ID NO: 2)
CTTCCCCAGTTCCAGGTTCTT FGFR3TACC3 V3
Forward:
                                        (SEQ ID NO: 3)
AGGACCTGGACCGTGTCCTT Reverse:
                                        (SEQ ID NO: 4)
TATAGGTCCGGTGGACAGGG FGFR3TACC3 Intron
Forward:
                                        (SEQ ID NO: 5)
GGCCATCCTGCCCCC
```

12

-continued

```
Reverse:
                                        (SEQ ID NO: 6)
GAGCAGTCCAGGTCAGCCAG FGFR3BAIAP2L1
Forward:
                                        (SEQ ID NO: 7)
CTGGACCGTGTCCTTACCGT Reverse:
                                        (SEQ ID NO: 8)
GCAGCCCAGGATTGAACTGT FGFR2BICC1
Forward:
                                        (SEQ ID NO: 9)
TGGATCGAATTCTCACTCTCACA Reverse:
                                        (SEQ ID NO: 10)
GCCAAGCAATCTGCGTATTTG FGFR2AFF3
Forward:
                                        (SEQ ID NO: 11)
TGGTAGAAGACTTGGATCGAATTCT Reverse:
                                        (SEQ ID NO: 12)
TCTCCCGGATTATTTCTTCAACA FGFR2CASP7
Forward:
                                        (SEQ ID NO: 13)
GCTCTTCAATACAGCCCTGATCA Reverse:
                                        (SEQ ID NO: 14)
ACTTGGATCGAATTCTCACTCTCA FGFR2CCDC6
Forward:
                                        (SEQ ID NO: 15)
TGGATCGAATTCTCACTCTCACA Reverse:
                                        (SEQ ID NO: 16)
GCAAAGCCTGAATTTTCTTGAATAA FGFR2OFD1
Forward:
                                        (SEQ ID NO: 17)
AGGGTGCATCAACTCATGAATTAG Reverse:
                                        (SEQ ID NO: 18)
ACTTGGATCGAATTCTCACTCTCA
```

The presence of one or more FGFR variants can be evaluated at any suitable time point including upon diagnosis, following tumor resection, following first-line therapy, during clinical treatment, or any combination thereof.

Evaluating PD-L1 Expression in the Cancer

The following methods for evaluating PD-L1 expression in a biological sample apply equally to any of the above disclosed methods of treatment.

In some embodiments, the disclosed methods can be dependent upon PD-L1 expression in the biological sample from the patient. Thus, administering to the patient a pharmaceutically effective amount of an antibody that blocks the interaction between PD-1 and PD-L1 and a pharmaceutically effective amount of an FGFR inhibitor may be based upon PD-L1 expression and the presence of one or more FGFR variants in the biological sample from the patient. The methods can comprise evaluating PD-L1 expression in a biological sample from the patient. The biological sample from which PD-L1 expression is evaluated can be the same biological sample from which the presence of one or more FGFR variants are evaluated, or the biological samples from which PD-L1 expression is evaluated can be a different biological sample from which the presence of one or more FGFR variants are evaluated. "Same biological sample" refers to a single sample from which both PD-L1 expression and FGFR variants are evaluated. "Different biological sample" includes the same source of sample (blood, lymph fluid, bone marrow, a solid tumor sample, etc.) taken at different time points or different sources of sample. For example, a blood sample can be obtained from the patient, evaluated for PD-L1 expression or the presence of one or more FGFR variants, and at a later time point, another blood sample can be obtained from the patient and evaluated for the presence of one or more FGFR variants or PD-L1 expression. Conversely, a blood sample can be obtained from the patient and evaluated for PD-L1 expression and/or the presence of one or more FGFR variants and a solid tumor sample can be obtained from the patient and evaluated for the presence of one or more FGFR variants and/or PD-L1 expression.

In some embodiments, the level of PD-L1 expression can be converted into a numerical H-score (as described in the methods section herein). The level of PD-L1 expression can be converted into a numerical H-score of: low PD-L1 expression, which includes an H-score of about 0 to about 99; moderate PD-L1 expression, which includes an H-score of about 100 to about 199; or high PD-L1 expression, which includes an H-score of about 200 to about 300. Treating the patient can be based upon these H-scores. For example, if the treatment methods are carried out on a patient with a low H-score, that patient would have PD-L1 expression corresponding to an H-score of about 0 to about 99. If the treatment methods are carried out on a patient with a moderate H-score, that patient would have PD-L1 expression corresponding to an H-score of about 100 to about 199. If the treatment methods are carried out on a patient with a high H-score, that patient would have PD-L1 expression corresponding to an H-score of about 200 to about 300.

In other embodiments, the level of PD-L1 expression can be compared to a reference PD-L1 expression level. In a preferred embodiment, the reference PD-L1 expression level can be predetermined. For example, a reference data set may be established using samples from unrelated patients with low, moderate and high PD-L1 expression levels. This data set can represent a standard by which relative PD-L1 expression levels are compared among patients and/or quantified using the H-Score method. In some embodiments, the reference PD-L1 expression level can be determined by comparing a patient population that is administered the antibody that blocks the interaction between PD-1 and PD-L1 to a patient population that is administered placebo. The PD-L1 expression level for each patient in the respective populations can be determined in accordance with the methods described herein. Clinical outcomes (e.g., progression-free survival or overall survival) for the patient populations can be monitored. Clinical outcomes for the patient populations relative to PD-L1 expression levels can then be compared. The reference PD-L1 expression level can correspond to the PD-L1 expression level above which the patient population that is administered the antibody that blocks the interaction between PD-1 and PD-L1 demonstrates a statistically significant improvement in at least one clinical outcome relative to the patient population that is administered placebo. A patient PD-L1 expression level that is less than the reference PD-L1 expression level, particularly when combined with the presence of one or more FGFR variants in a patient sample, can be indicative that the patient will benefit from treatment with the antibody that that blocks the interaction between PD-1 and PD-L1 in combination with an FGFR inhibitor. For example, in some embodiments, the methods can comprise administering an antibody that blocks the interaction between PD-1 and PD-L1 and an FGFR inhibitor, wherein the antibody that blocks the interaction between PD-1 and PD-L1 and the FGFR inhibitor are administered if one or more FGFR variants are present in a biological sample from the patient and the PD-L1 expression in the biological sample is less than a reference PD-L1 expression level, wherein the reference PD-L1 expression level corresponds to a PD-L1 expression level above which treatment with the antibody that blocks the interaction between PD-1 and PD-L1 alone is likely to be efficacious.

Methods for determining PD-L1 expression include, but are not limited to, immunohistochemistry (IHC), Western Blotting, microscopy, immunoprecipitation, BCA assays, spectrophotometry, or any combination thereof. Exemplary methods for evaluating PD-L1 expression are described in the methods section herein.

PD-L1 expression can be evaluated at any suitable time point including upon diagnosis, following tumor resection, following first-line therapy, during clinical treatment, or any combination thereof.

The following examples are provided to further describe some of the embodiments disclosed herein. The examples are intended to illustrate, not to limit, the disclosed embodiments.

Examples

Methods

PD-L1 Immunohistochemistry

PD-L1 immunohistochemistry (IHC) was performed at a CRO (QualTek, Newtown, PA). Samples were stained using a CD274 PD-L1 (RUO) assay. Slides stained with a CD274 PD-L1 (RUO) assay were examined in random order and/or in blinded fashion by a board-certified clinical pathologist, the Medical Director of QualTek Clinical Laboratories (CAP/CLIA facility). The entire tissue section was evaluated for CD274 PD-L1. Only viable tissue was evaluated; areas of necrosis or obviously poorly fixed areas of tissue were not evaluated.

The tumor H-Score was calculated from the intensity of CD274 PD-L1 membrane reactivity on a four-point semi-quantitative scale (0: null, negative or non-specific staining of cell membranes; 1+: low or weak intensity staining of cell membranes; 2+: medium or moderate intensity staining of cell membranes; and 3+: high or strong intensity staining of cell membranes) and the estimated percentage of CD274 PD-L1 positive tumor cells (0-100%) for each discrete intensity value.

Tumor CD274 PD-L1 membrane reactivity was captured by a standard H-Score–the tumor H-Score minimum of 0 and the tumor H-Score maximum of 300: Tumor H-Score= ([% positive cells at 1+]*1)+([% positive cells at 2+]*2)+ ([% positive cells at 3+]*3)

Next-Generation Sequencing (NGS)

NGS for FGFR mutations and gene amplification was performed by Foundation Medicine, Cambridge, MA using the FoundationOne panel (http://www.foundationmedicine. com).

FGFR Fusions

FGFR fusions were determined using a proprietary qRT-PCR assay developed by Janssen Oncology Translational Research as described in U.S. Provisional Application No. 62/056,159.

Results

PD-L1 Expression in Tumors with FGFR Fusions and Mutations

To determine the overlap of PD-L1 expression with FGFR alterations, immunohistochemistry (IHC) for PD-L1 was performed on human tumor tissue samples which were subsequently assessed for FGFR alterations. FGFR amplifications and mutations were identified using next-generation sequencing (Foundation Medicine panel, FMI). FGFR fusions were screened for using a Janssen-developed qRT-PCR assay.

Correlation of FGFR Mutations and Amplification with PD-L1

PD-L1 expression was first assessed in a set of 120 commercially sourced lung FFPE tumor tissues comprised of forty of each of the following lung tumor histologies; non-small-cell lung carcinoma (NSCLC) adenocarcinoma; NSCLC squamous cell carcinoma; and small-cell lung cancer (SCLC). FGFR mutations and gene amplification were detected using the Foundation Medicine panel. PD-L1 staining versus FGFR status was plotted for each tumor type (FIG. 1). PD-L1 expression was largely reserved to tumors without FGFR mutations or amplifications. Out of nine samples with FGFR mutations, no PD-L1 staining was observed in seven samples (78%). Two of the nine samples showed very low PD-L1 staining with H-scores of 20 and 70, respectively. Of four samples with FGFR gene amplification, one sample showed moderate-high PD-L1 staining (H-score=140), with three having almost no staining (H-score=4, n=1). No staining was observed in the one tumor sample harboring both an FGFR mutation and FGFR gene amplification. FGFR mutation and amplification status was unknown for 24 tumor samples, of which nine exhibited PD-L1 staining with H-scores ranging from 55 to 220.

FGFR Fusions and PD-L1 Expression in Bladder and NSCLC

Figure 2:
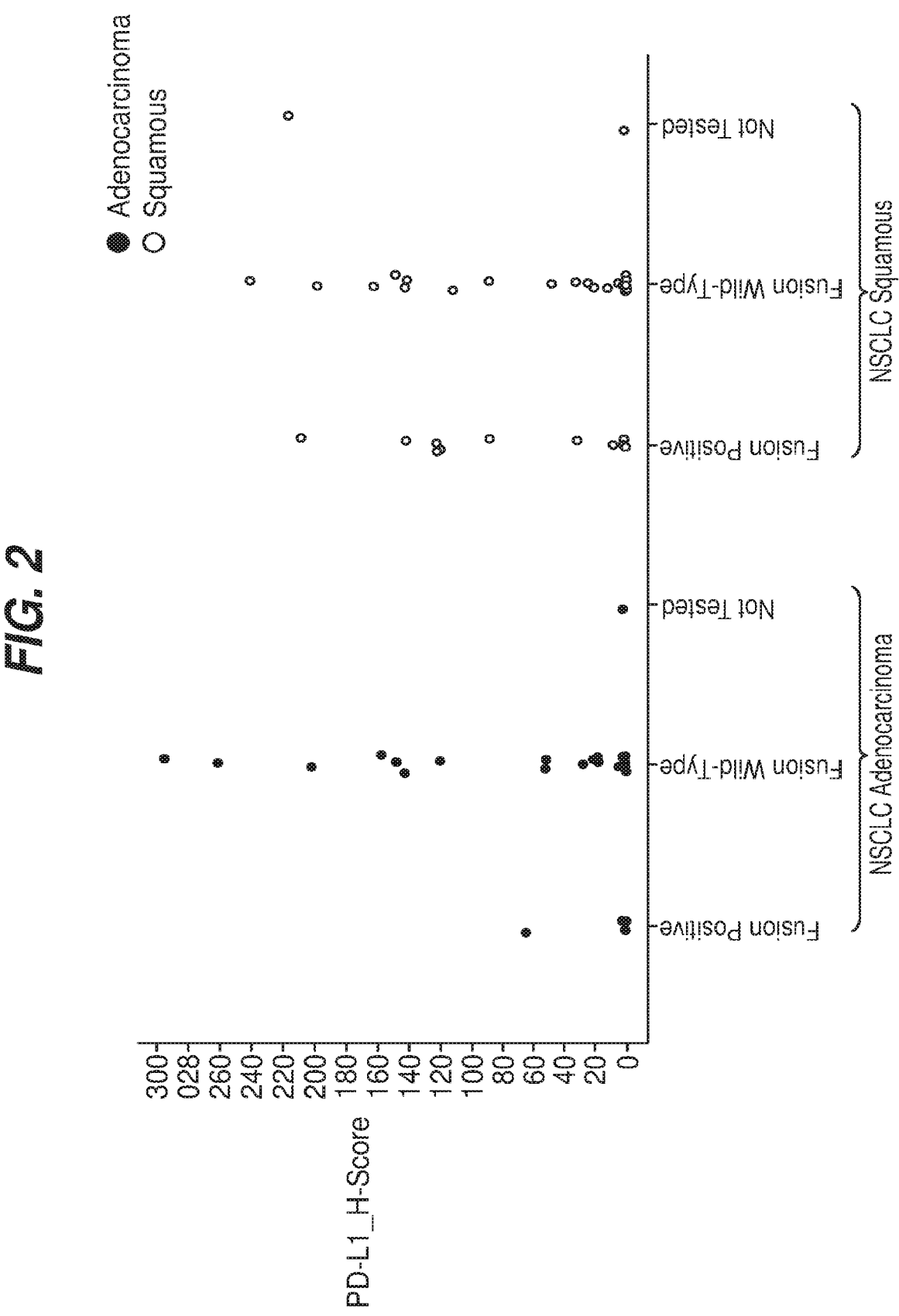
FIG. 2 illustrates PD-L1 expression in an 80 non-small-cell lung carcinoma (NSCLC) sample set by FGFR fusion status by NSCLC histology. PD-L1 H-scores (Y-axis) were plotted for NSCLC adenocarcinoma (left), and NSCLC squamous (right). The FGFR fusion status versus the PD-L1 staining for each of the 80 samples is shown. Fusion Positive—an FGFR fusion was detected; Fusion Wild-Type—no FGFR fusion was detected; Not Tested—insufficient sample for testing or QC failure.

The set of 120 lung FFPE tumor tissues was subsequently screened for FGFR fusions using a Janssen-developed qRT-PCR assay (as described in U.S. Provisional Application No. 62/056,159) detecting nine fusions (Table 1). Results for PD-L1 expression by FGFR fusion status for the NSCLC tumor samples (n=80) are shown in FIG. 2. Twenty-three percent (7/31) of NSCLC adenocarcinoma samples, and 52% (13/25) of NSCLC squamous cell carcinoma tumor samples were positive for FGFR fusions. All fusion-positive adenocarcinoma samples exhibited no or low PD-L1 expression, 6/7 (86%) or 1/7 (14%), respectively (Table 2). Fusion-negative adenocarcinoma samples showed a range of PD-L1 from no expression (12/31, 39%), low (12/31, 39%), moderate (4/31, 13%), to high PD-L1 (3/31, 10%) (Table 2). Fusion-positive squamous cell carcinoma sample PD-L1 H-scores were equally distributed across the no expression, low, moderate, or high expression categories (4/31, 31% each respectively) (Table 3). Fusion-negative squamous samples also showed a range of H-scores from no expression (6/25, 24%), low (11/25, 44%), moderate (5/25, 20%), and high expression (3/25, 12%) (Table 3).

TABLE 2

| NSCLC Adenocarcinoma - PD-L1 H-Scores by FGFR fusion status | | | | | | |
|---|---|---|---|---|---|---|
| NSCLC Adeno- | | | H-Score Range | | | |
| carcinoma | 0 | 1-25 | 26-50 | 51-99 | 100-199 | 200-300 |
| Category: | No | | Low | | Mod. | High |
| Fusion Positive | 6 (86%) | — | — | 1 (14%) | — | — |
| Fusion Negative | 12 (39%) | 9 (29%) | 2 (6%) | 1 (3%) | 4 (13%) | 3 (10%) |

TABLE 3

| NSCLC Squamous Cell Carcinoma - PD-L1 H-Scores by FGFR fusion status | | | | | | |
|---|---|---|---|---|---|---|
| NSCLC Squamous | | | H-Score Range | | | |
| | 0 | 1-25 | 26-50 | 51-99 | 100-199 | 200-300 |
| Category: | No | | Low | | Mod. | High |
| Fusion Positive | 4 (31%) | 2 (15%) | 1 (8%) | 1 (8%) | 4 (31%) | 1 (8%) |
| Fusion Negative | 6 (24%) | 8 (32%) | 2 (8%) | 1 (4%) | 5 (20%) | 3 (12%) |

Forty-five commercially sourced bladder tumors were sequenced for mutations by the Foundation Medicine panel (FMI), stained for PD-L1 expression, and screened for FGFR gene fusions using the Janssen qRT-PCR assay. Forty-two of 45 samples (93%) were positive for FGFR fusions. Five samples (11%) were positive for an FGFR mutation (FGFR3-R248C or FGFR3-S249C), all of which were also positive for FGFR fusions. PD-L1 staining H-scores for samples with FGFR alterations are summarized in Table 4, and listed in Table 5. For FGFR fusion positive samples, 22/37 (59%) were negative for PD-L1 staining. Ten FGFR fusion-positive samples (27%) expressed low levels of PD-L1, and five samples (14%) showed high PD-L1 expression. All samples with both FGFR mutations and FGFR fusions in the same tumor sample (n=5) were negative for PD-L1 staining. Overall, PD-L1 staining was absent in 64% (27/42) of bladder samples with FGFR alterations, keeping in mind that almost all of the tumors in this sample set were positive for FGFR fusions.

FGFR mutation and PD-L1 expression data were available for seven commercially sourced metastatic NSCLC samples with FGFR fusions (Janssen). No PD-L1 staining was observed in 4/7 (57%) of samples. Two samples exhibited very low PD-L1 staining, H-scores of 4 and 15. One sample showed moderate PD-L1 with an H-score of 160. Interestingly, the FGFR fusion-positive sample with moderate PD-L1 staining harbored an FGFR4 V550I mutation—an FGFR gatekeeper residue mutation with potential to confer resistance to tyrosine kinase inhibitors.

Overall these data show that the majority of commercially available tumor samples harboring FGFR alterations have very little expression or do not express PD-L1.

TABLE 4

| PD-L1 staining in FGFR fusion positive bladder samples | | | | | | |
|---|---|---|---|---|---|---|
| | H-Score Range | | | | | |
| n = 42 | 0 | 1-25 | 26-50 | 51-99 | 100-199 | 200-300 |
| Category: | No | | Low | | Mod. | High |
| Fusion Positive | 22 | 8 | — | 2 | — | 5 |
| Fusion + Mutation | 5 | — | — | — | — | — |

TABLE 4-continued

| PD-L1 staining in FGFR fusion positive bladder samples | | | | | | |
|---|---|---|---|---|---|---|
| | H-Score Range | | | | | |
| n = 42 | 0 | 1-25 | 26-50 | 51-99 | 100-199 | 200-300 |
| % of Total FGFR + Samples Expressing per Category | 64% | 19% | 0% | 5% | 0% | 12% |

TABLE 5

| PD-L1 expression, FGFR fusion and mutation status in commercial bladder and NSCLC tumor samples | | | | |
|---|---|---|---|---|
| Janssen Sample ID | Tumor Type | FGFR Fusion Gene(s) | FGFR Mutation | H-Score (0-300) |
| 2329 | Bladder | None | None | 300 |
| 2425 | Bladder | FGFR3:BAIA/FGFR2:CASP7/ FGFR2:OFD1 | None | 300 |
| F26993.C3a | Bladder | FGFR3:BAIA/FGFR2:AFF/ FGFR2:CASP7/FGFR2:CCDC6 | None | 300 |
| F5244.E22b | Bladder | FGFR2:CASP7 | None | 300 |
| F28052.E14a | Bladder | FGFR2:BICC1/FGFR2:AFF3/ FGFR2:CCDC6 | None | 280 |
| F27999.D25 | Bladder | FGFR3:BAIA/FGFR2:CCDC6 | None | 250 |
| F7799.H25b | Bladder | FGFR3:BAIAP2L/FGFR2:CASP7/ FGFR2:OFD | None | 70 |
| F28057.D1a | Bladder | FGFR3:BAIA | None | 60 |
| F15377.A2 | Bladder | FGFR2:AFF3 | None | 21 |
| F28137.G3b | Bladder | FGFR3:TACC3v3/FGFR2:AFF3 | None | 20 |
| F7538.A1b | Bladder | FGFR3:BAIAP2L/FGFR2:BICC1/ FGFR:AFF3/FGFR2:CASP7 | None | 20 |
| F26375.A2 | Bladder | FGFR3:BAIA/FGFR2:AFF/ FGFR2:CASP7 | None | 18 |
| F7830.G3ba | Bladder | FGFR2:CASP7 | None | 10 |
| F7860.B2b | Bladder | FGFR2:AFF3FGFR2:CASP7 | None | 10 |
| F27338.C4a | Bladder | FGFR3:BAIA/FGFR2:CASP7 | None | 6 |
| F5242.G10ba | Bladder | FGFR2:CASP7 | None | 3 |
| 2319 | Bladder | FGFR2:CASP7 | None | 0 |
| 2321 | Bladder | None | None | 0 |
| 2346 | Bladder | FGFR3:BAIA/FGFR2:CASP7/ FGFR2:OFD1 | None | 0 |
| 2347 | Bladder | FGFR3:BAIAP2L1/FGFR2:CCDC6 | FGFR3-S249C | 0 |
| 2362 | Bladder | FGFR3:TACC3v1/FGFR3:TACC3v3/ FGFR3:BAIA/FGFR2:BICC1/ FGFR2:AFF3/FGFR2:CASP7/ FGFR2:CCDC6 | FGFR3-S249C | 0 |
| 2376 | Bladder | FGFR3:TACC3, v1/ FGFR2:BICC1/FGFR2:CASP7 | None | 0 |
| 2381 | Bladder | FGFR3:BAIA/FGFR2:AFF3/ FGFR2:CASP7 | FGFR3-R248C | 0 |
| 2430 | Bladder | FGFR3:BAIA/FGFR2:CASP7 | None | 0 |
| 2434 | Bladder | FGFR3:BAIA | None | 0 |
| 2458 | Bladder | FGFR3:BAIA/FGFR2:AFF3/ FGFR2:CASP7 | FGFR3-R248C | 0 |
| 2455 | Bladder | None | None | 0 |
| 2473 | Bladder | FGFR2:AFF3/FGFR2:OFD1 | None | 0 |
| 2480 | Bladder | FGFR2:OFD1 | None | 0 |
| 2518 | Bladder | FGFR3:BAIA/FGFR2:AFF3/ FGFR2:CASP7/FGFGFR2:OFD1 | None | 0 |
| 2533 | Bladder | FGFR2:OFD1 | None | 0 |
| 2541 | Bladder | FGFR2:CASP7/FGFR2:OFD1 | None | 0 |
| 2561 | Bladder | FGFR3:BAIA/FGFR2:BICC1/ FGFR2:AFF3/FGFR2:CASP7 | None | 0 |
| 2563 | Bladder | FGFR2:OFD1 | None | 0 |
| 4916 | Bladder | FGFR2:OFD1 | None | 0 |
| F27064.CFS | Bladder | FGFR3:BAIA/FGFR2:AFF/ FGFR2:CASP7 | None | 0 |
| F28132.Ba | Bladder | FGFR3:TACC3v1/FGFR3:BAIAP2L/ FGFR2:BICC1/FGFR2:CCDC6 | None | 0 |
| F7269.C2 | Bladder | FGFR3:BAIAP2L/FGFR2:CASP7 | None | 0 |
| F7271.AFSb | Bladder | FGFR2:AFF3/FGFR2:CASP7 | None | 0 |

TABLE 5-continued

| Janssen Sample ID | Tumor Type | FGFR Fusion Gene(s) | FGFR Mutation | H-Score (0-300) |
|---|---|---|---|---|
| | | PD-L1 expression, FGFR fusion and mutation status in commercial bladder and NSCLC tumor samples | | |
| F7467.D1bb | Bladder | FGFR2:AFF3/FGFR2:CASP7/ FGFR2:CCDC6 | None | 0 |
| F7484.BFSc | Bladder | FGFR2:AFF3 | None | 0 |
| F7502.D1b | Bladder | FGFR2:AFF3/FGFR2:CASP7 | FGFR3-S249C | 0 |
| F7789.DFSb | Bladder | FGFR3:BAIAP2L/FGFR2:CASP7 | FGFR2-M537I | 0 |
| F7876.D1bb | Bladder | FGFR3:BAIAP2L/FGFR2:OFD1 | None | 0 |
| I-7290.E13a | Bladder | FGFR2:CASP7 | None | 0 |
| CNT06GK | NSCLC | FGFR3:TACC3intron | FGFR4-V550I | 160 |
| CNT0RHX | NSCLC | FGFR3:BAIAP2L | None | 15 |
| CNT0RFD | NSCLC | FGFR2:BICC1 | None | 4 |
| CNT06FI | NSCLC | FGFR2:AFF3 | None | 0 |
| CNT06FJ | NSCLC | FGFR2:CCDC6 | None | 0 |
| CNT06G5 | NSCLC | FGFR3:TACC3v1/ FGFR3:TACC3intron/FGFR2:AFF3 | None | 0 |
| CNT0RFX | NSCLC | FGFR3:BAIAP2L/FGFR2:CASP7 | None | 0 |

FGFR In Vitro Experiments

Figure 3:
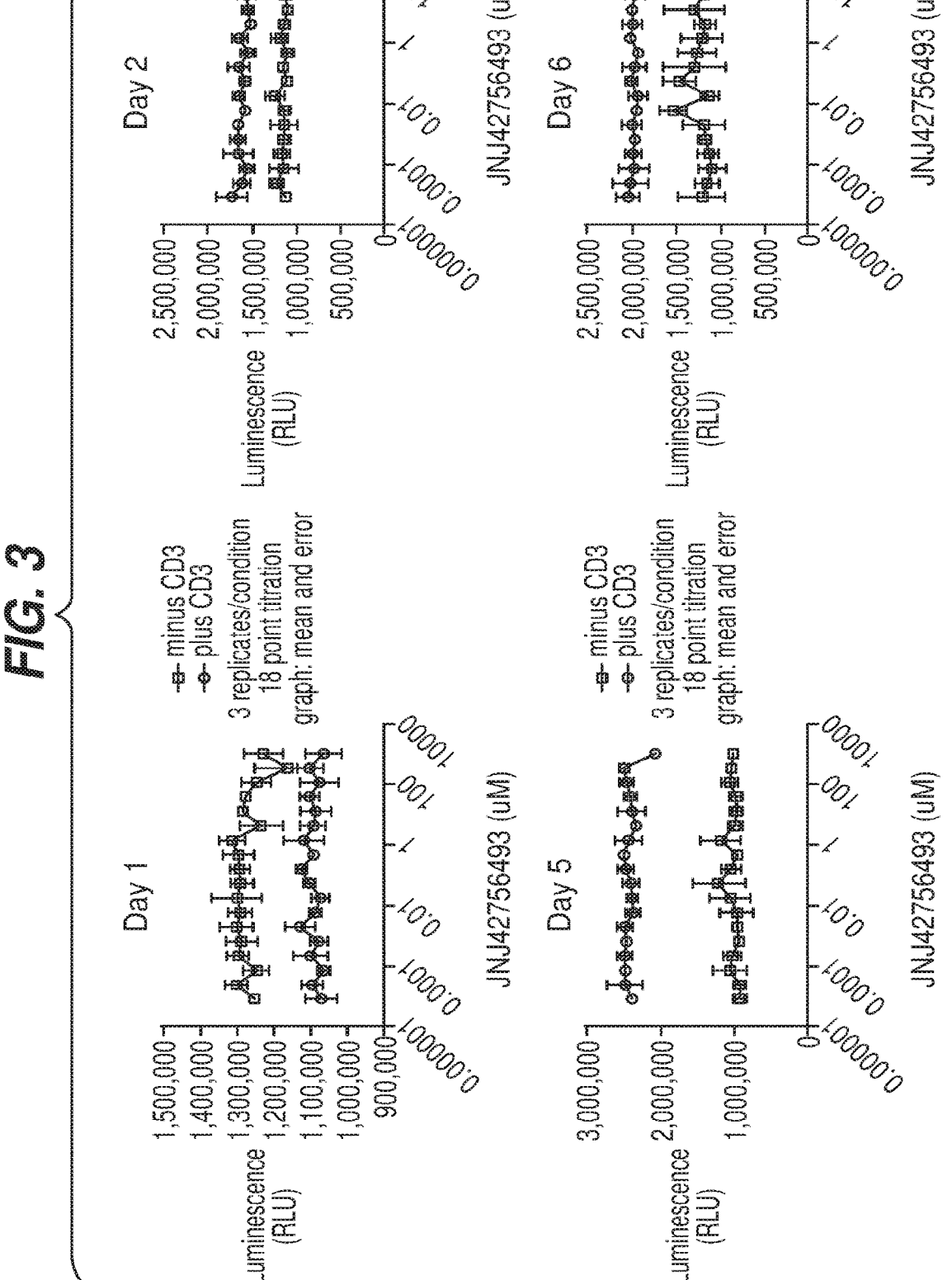
FIG. 3 illustrates the effect of JNJ42756493 on immune cell viability. Normal donor peripheral blood mononuclear cells (PBMCs), either unstimulated or stimulated with anti-CD3 antibodies, were treated with increasing concentrations of JNJ42756493 (0.0000077, 0.000023, 0.000070, 0.00021, 0.00063, 0.00188, 0.00565, 0.01694, 0.051, 0.152, 0.457, 1.372, 4.115, 12.346, 37.037, 111.111, 333.333, and 1000 nM). On days 1, 2, 5 and 6 after plating, cell viability was assessed by CellTiter-Glo (Promega).

To determine the effects of JNJ427564493 on immune cell viability in vitro, peripheral blood mononuclear cells (PBMCs) from normal donors were stimulated with anti-CD3 antibodies to activate T cells, in the presence of increasing concentrations of JNJ42756493. Unstimulated PBMCs were also included to determine if JNJ42756493 affected unactivated immune populations. Cell viability was assessed at four different time points, over 6 days. FIG. 3 shows the luminescence signal, as a measurement of cell viability, in the presence of increasing concentrations of JNJ42756493 (up to 1 μM) at days 1, 2, 5 and 6 post-treatment. For both the stimulated and unstimulated groups, at all time points tested, cell viability remained constant with increasing concentrations of compound. These data suggest that the addition of JNJ42756493 does not impair immune cell viability.

Figure 4:
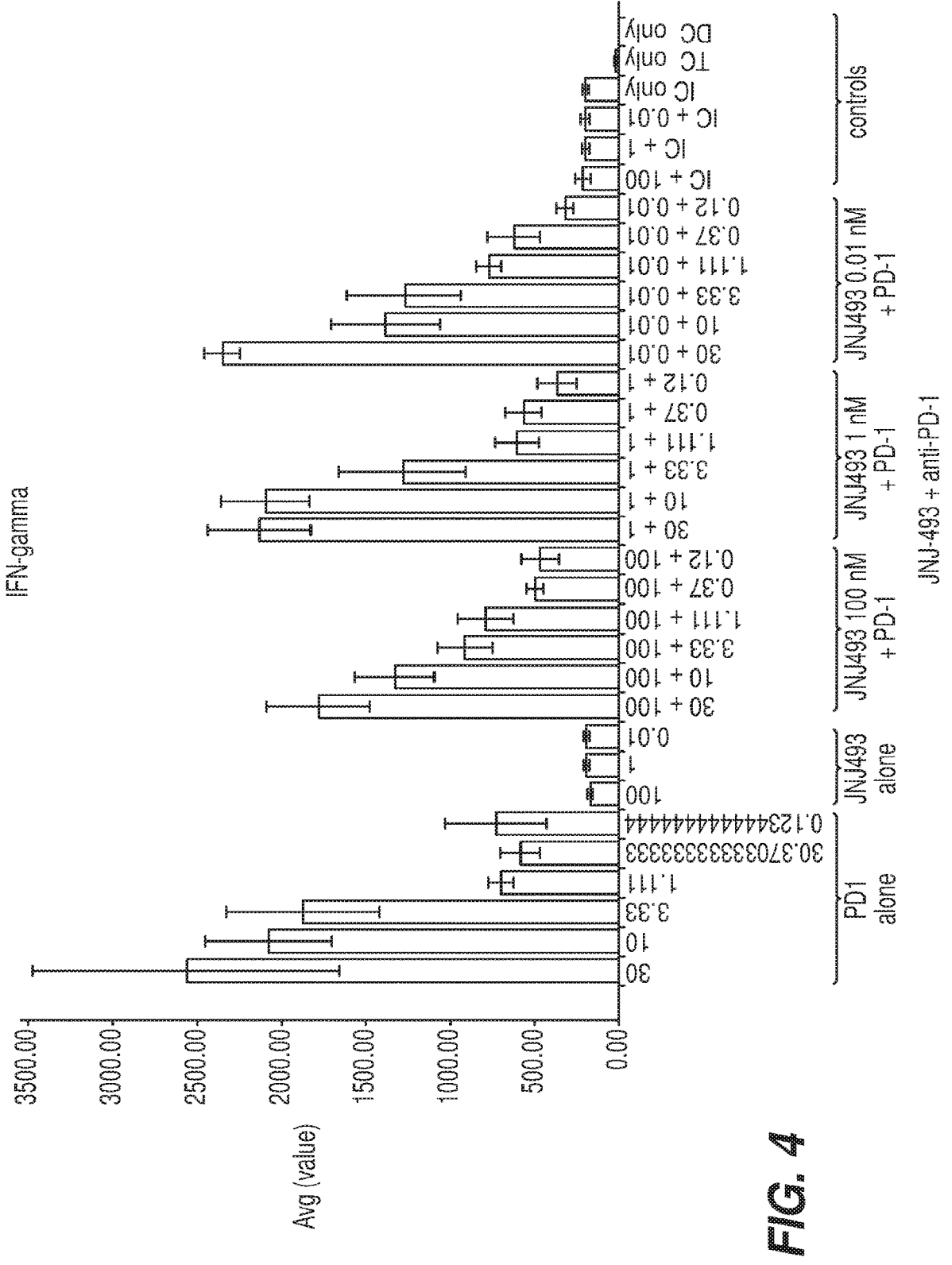
FIG. 4 illustrates the effect of JNJ42756493 on IFN-$\gamma$ levels induced by anti-PD-1 antibodies in a Mixed Lymphocyte Reaction (MLR) Assay. Cultures of CD4$^+$ T and allogeneic dendritic cells were treated with anti-PD-1 antibodies (concentrations left to right—30, 10, 3.33, 1.11, 0.37, 0.12 nM). JNJ42756493 was added at 100, 1, or 0.01 nM alone (concentrations left to right), together with anti-PD-1 antibodies (100, 1, or 0.01 nM JNJ42756493 together with 30, 10, 3.33, 1.11, 0.37, or 0.12 nM of anti-PD-1 antibody), or in the presence of isotype control (IC). 5 days after treatment, IFN-$\gamma$ levels in the supernatant were measured by Meso Scale Discovery (MSD).

JNJ42756493 was next tested to analyze the impact on the activity of anti-PD-1 antibodies in two in vitro functional assays: Mixed Lymphocyte Reaction (MLR); and Cytomegalovirus antigen assay (CMV). For the MLR assay, CD4⁺ T cells are stimulated with allogeneic dendritic cells, leading to T cell activation and IFN-γ secretion. In this assay, anti-PD-1 antibodies caused dose-dependent increases in IFN-γ levels (FIG. 4, PD-1 alone). When T cells and DCs were treated with 0.01, 1 or 100 nM of JNJ42756493, IFN-γ levels were similar to those observed in the untreated samples (FIG. 4, JNJ-493 alone vs controls), suggesting that FGFR inhibition does not affect T cell activation. Furthermore, combinations of JNJ42756493 with anti-PD-1 antibodies caused similar IFN-γ secretion as observed with anti-PD-1 treatment alone (FIG. 4, JNJ-493+anti-PD-1 compared to PD-1 alone). These results suggest that JNJ42756493 does not impair the functional activity of anti-PD-1 antibodies in the MLR assay.

Figure 5:
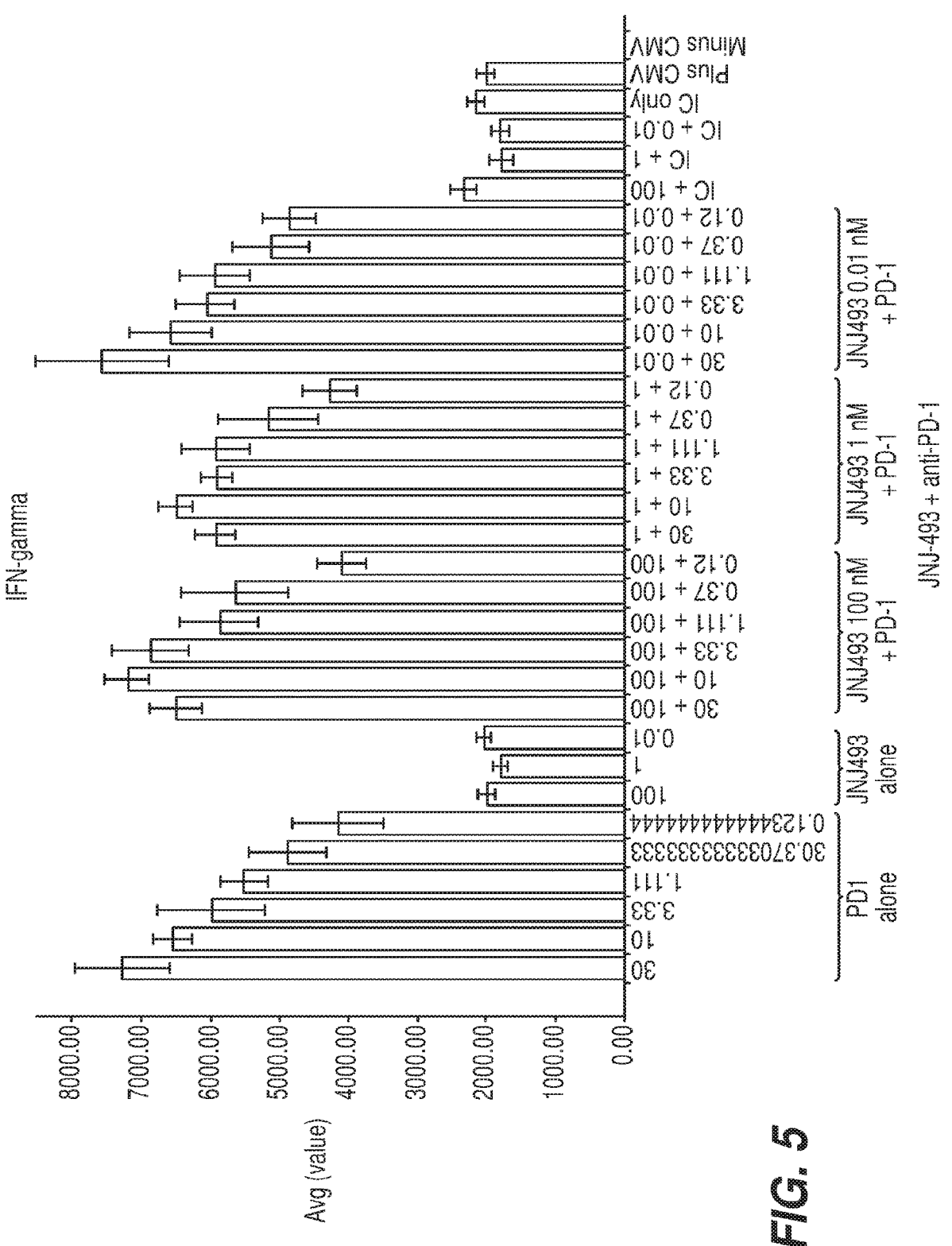
FIG. 5 illustrates the effect of JNJ42756493 on IFN-$\gamma$ levels induced by anti-PD-1 antibodies in a Cytomegalovirus antigen assay (CMV) Assay. Peripheral blood mononuclear cells (PMBCs) were stimulated with CMV antigen and treated with anti-PD-1 antibodies (concentration left to right—30, 10, 3.33, 1.11, 0.37, 0.12 nM) as indicated. JNJ42756493 was added at 100, 1, or 0.01 nM alone (concentrations left to right), together with anti-PD-1 antibodies (100, 1, or 0.01 nM JNJ42756493 together with 30, 10, 3.33, 1.11, 0.37, or 0.12 nM of anti-PD-1 antibody), or in the presence of isotype control (IC). 6 days after treatment, IFN-γ levels in the supernatant were measured by MSD.

In the CMV assay, PBMCs from CMV-reactive donors were stimulated by the addition of CMV antigen. CMV-reactive T cells are active, expand and secrete pro-inflammatory cytokines such as IFN-γ. In the presence of anti-PD-1 antibodies, significantly higher levels of IFN-γ were secreted upon CMV stimulation (FIG. 5, PD-1 alone). In contrast, JNJ42756493 alone had no impact on cytokine levels (FIG. 5, JNJ-493 alone). Similarly, JNJ42756493 combinations with anti-PD-1 antibodies led to similar increases of IFN-γ as seen with anti-PD-1 alone (FIG. 5, JNJ42756493+anti-PD-1 compared to PD-1 alone). These data show that JNJ42756493 does not affect the activity of anti-PD-1 antibodies in the CMV assay.

Those skilled in the art will appreciate that numerous changes and modifications can be made to the preferred embodiments and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

Nucleotide Sequence of FGFR Fusion Genes

The nucleotide sequences for the FGFR fusion cDNA are provided in Table 6. The underlined sequences correspond to either FGFR3 or FGFR2, the sequences in black represent the fusion partners and the sequence in italic fonts represent the intron sequence of the FGFR3 gene.

TABLE 6

| FGFR3:TACC3 v1 (2850 base pairs) (SEQ ID NO: 19) | >ATGGGCGCCCCTGCCTGCGCCCTCGCGCTCTGCGTGGCCGTGGCCATCGTGGCC GGCGCCTCCTCGGAGTCCTTGGGGACGGAGCAGCGCGTCGTGGGGCGAGCGGCA GAAGTCCCGGGCCCAGAGCCCGGCCAGCAGGAGCAGTTGGTCTTCGGCAGCGGG GATGCTGTGGAGCTGAGCTGTCCCCCGCCCGGGGGTGGTCCCATGGGGCCCACTG TCTGGGTCAAGGATGGCACAGGGCTGGTGCCCTCGGAGCGTGTCCTGGTGGGGC CCCAGCGGCTGCAGGTGCTGAATGCCTCCCACGAGGACTCCGGGGCCTACAGCT GCCGGCAGCGGCTCACGCAGCGCGTACTGTGCCACTTCAGTGTGCGGGTGACAG ACGCTCCATCCTCGGGAGATGACGAAGACGGGGAGGGACGAGGCTGAGGACACA GGTGTGGACACAGGGGCCCCTTACTGGACACGGCCCGAGCGGATGGACAAGAAG CTGCTGGCCGTGCCGGCCGCCAACACCGTCCGCTTCCGCTGCCCAGCCGCTGGCA ACCCCACTCCCTCCATCTCCTGGCTGAAGAACGGCAGGGAGTTCCGCGGCGAGC ACCGCATTGGAGGCATCAAGCTGCGGCATCAGCAGTGGAGCCTGGTCATGGAAA GCGTGGTGCCCTCGGACCGCGGCAACTACACCTGCGTCGTGGAGAACAAGTTTG |
|---|---|

TABLE 6-continued

```
GCAGCATCCGGCAGACGTACACGCTGGACGTGCTGGAGCGCTCCCCGCACCGGC
CCATCCTGCAGGCGGGGCTGCCGGCCAACCAGACGGCGGTGCTGGGCAGCGACG
TGGAGTTCCACTGCAAGGTGTACAGTGACGCACAGCCCCACATCCAGTGGCTCA
AGCACGTGGAGGTGAATGGCAGCAAGGTGGGCCCGGACGGCACACCCTACGTTA
CCGTGCTCAAGACGGCGGGCGCTAACACCACCGACAAGGAGCTAGAGGTTCTCT
CCTTGCACAACGTCACCTTTGAGGACGCCGGGGAGTACACCTGCCTGGCGGGCA
ATTCTATTGGGTTTTCTCATCACTCTGCGTGGCTGGTGGTGCTGCCAGCCGAGGA
GGAGCTGGTGGAGGCTGACGAGGCGGGCAGTGTGTATGCAGGCATCCTCAGCTA
CGGGGTGGGCTTCTTCCTGTTCATCCTGGTGGTGGCGGCTGTGACGCTCTGCCGC
CTGCGCAGCCCCCCCAAGAAAGGCCTGGGCTCCCCCACCGTGCACAAGATCTCCC
GCTTCCCGCTCAAGCGACAGGTGTCCCTGGAGTCCAACGCGTCCATGAGCTCCAA
CACACCACTGGTGCGCATCGCAAGGCTGTCCTCAGGGGAGGGCCCCACGCTGGC
CAATGTCTCCGAGCTCGAGCTGCCTGCCGACCCCAAATGGGAGCTGTCTCGGGCC
CGGCTGACCCTGGGCAAGCCCCTTGGGGAGGGCTGCTTCGGCCAGGTGGTCATG
GCGGAGGCCATCGGCATTGACAAGGACCGGGCCGCCAAGCCTGTCACCGTAGCC
GTGAAGATGCTGAAAGACGATGCCACTGACAAGGACCTGTCGGACCTGGTGTCT
GAGATGGAGATGATGAAGATGATCGGGAAACACAAAAACATCATCAACCTGCTG
GGCGCCTGCACGCAGGGCGGGCCCCTGTACGTGCTGGTGGAGTACGCGGCCAAG
GGTAACCTGCGGGAGTTTCTGCGGGCGCGGCGGCCCCCGGGCCTGGACTACTCCT
TCGACACCTGCAAGCCGCCCGAGGAGCAGCTCACCTTCAAGGACCTGGTGTCCTG
TGCCTACCAGGTGGCCCGGGGCATGGAGTACTTGGCCTCCCAGAAGTGCATCCAC
AGGGACCTGGCTGCCCGCAATGTGCTGGTGACCGAGGACAACGTGATGAAGATC
GCAGACTTCGGGCTGGCCCGGGACGTGCACAACCTCGACTACTACAAGAAGACG
ACCAACGGCCGGCTGCCCGTGAAGTGGATGGCGCCTGAGGCCTTGTTTGACCGA
GTCTACACTCACCAGAGTGACGTCTGGTCCTTTGGGGTCCTGCTCTGGGAGATCT
TCACGCTGGGGGGGCTCCCCGTACCCCGGCATCCCTGTGGAGGAGCTCTTCAAGCT
GCTGAAGGAGGGCCACCGCATGGACAAGCCCGCCAACTGCACACACGACCTGTA
CATGATCATGCGGGAGTGCTGGCATGCCGCGCCCTCCCAGAGGCCCACCTTCAAG
CAGCTGGTGGAGGACCTGGACCGTGTCCTTACCGTGACGTCCACCGACGTAAAG
GCGACACAGGAGGAGAACCGGGAGCTGAGGAGCAGGTGTGAGGAGCTCCACGG
GAAGAACCTGGAACTGGGGAAGATCATGGACAGGTTCGAAGAGGTTGTGTACCA
GGCCATGGAGGAAGTTCAGAAGCAGAAGGAACTTTCCAAAGCTGAAATCCAGAA
AGTTCTAAAAGAAAAAGACCAACTTACCACAGATCTGAACTCCATGGAGAAGTC
CTTCTCCGACCTCTTCAAGCGTTTTGAGAAACAGAAAGAGGTGATCGAGGGCTAC
CGCAAGAACGAAGAGTCACTGAAGAAGTGCGTGGAGGATTACCTGGCAAGGATC
ACCCAGGAGGGCCAGAGGTACCAAGCCCTGAAGGCCCACGCGGAGGAGAAGCT
GCAGCTGGCAAACGAGGAGATCGCCCAGGTCCGGAGCAAGGCCCAGGCGGAAG
CGTTGGCCCTCCAGGCCAGCCTGAGGAAGGAGCAGATGCGCATCCAGTCGCTGG
AGAAGACAGTGGAGCAGAAGACTAAAGAGAACGAGGAGCTGACCAGGATCTGC
GACGACCTCATCTCCAAGATGGAGAAGATCTGA
```

FGFR3:TACC3 v3
(2955 base pairs)
(SEQ ID NO: 20)

```
>ATGGGCGCCCCTGCCTGCGCCCTCGCGCTCTGCGTGGCCGTGGCCATCGTGGCC
GGCGCCTCCTCGGAGTCCTTGGGGACGGAGCAGCGCGTCGTGGGGCGAGCGGCA
GAAGTCCCGGGCCCAGAGCCCGGCCAGCAGGAGCAGTTGGTCTTCGGCAGCGGG
GATGCTGTGGAGCTGAGCTGTCCCCCGCCCGGGGGTGGTCCCATGGGGCCCACTG
TCTGGGTCAAGGATGGCACAGGGCTGGTGCCCTCGGAGCGTGTCCTGGTGGGGC
CCCAGCGGCTGCAGGTGCTGAATGCCTCCCACGAGGACTCCGGGGCCTACAGCT
GCCGGCAGCGGCTCACGCAGCGCGTACTGTGCCACTTCAGTGTGCGGGTGACAG
ACGCTCCATCCTCGGGAGATGACGAAGACGGGGAGGACGAGGCTGAGGACACA
GGTGTGGACACAGGGGCCCCTTACTGGACACGGCCCGAGCGGGATGGACAAGAAG
CTGCTGGCCGTGCCGGCCGCCAACACCGTCCGCTTCCGCTGCCCAGCCGCTGGCA
ACCCCACTCCCTCCATCTCCTGGCTGAAGAACGGCAGGGAGTTCCGCGGCGAGC
ACCGCATTGGAGGCATCAAGCTGCGGCATCAGCAGTGGAGCCTGGTCATGGAAA
GCGTGGTGCCCTCGGACCGCGGCAACTACACCTGCGTCGTGGAGAACAAGTTTG
GCAGCATCCGGCAGACGTACACGCTGGACGTGCTGGAGCGCTCCCCGCACCGGC
CCATCCTGCAGGCGGGGCTGCCGGCCAACCAGACGGCGGTGCTGGGCAGCGACG
TGGAGTTCCACTGCAAGGTGTACAGTGACGCACAGCCCCACATCCAGTGGCTCA
AGCACGTGGAGGTGAATGGCAGCAAGGTGGGCCCGGACGGCACACCCTACGTTA
CCGTGCTCAAGACGGCGGGCGCTAACACCACCGACAAGGAGCTAGAGGTTCTCT
CCTTGCACAACGTCACCTTTGAGGACGCCGGGGAGTACACCTGCCTGGCGGGCA
ATTCTATTGGGTTTTCTCATCACTCTGCGTGGCTGGTGGTGCTGCCAGCCGAGGA
GGAGCTGGTGGAGGCTGACGAGGCGGGCAGTGTGTATGCAGGCATCCTCAGCTA
CGGGGTGGGCTTCTTCCTGTTCATCCTGGTGGTGGCGGCTGTGACGCTCTGCCGC
CTGCGCAGCCCCCCCAAGAAAGGCCTGGGCTCCCCCACCGTGCACAAGATCTCCC
GCTTCCCGCTCAAGCGACAGGTGTCCCTGGAGTCCAACGCGTCCATGAGCTCCAA
CACACCACTGGTGCGCATCGCAAGGCTGTCCTCAGGGGAGGGCCCCACGCTGGC
CAATGTCTCCGAGCTCGAGCTGCCTGCCGACCCCAAATGGGAGCTGTCTCGGGCC
CGGCTGACCCTGGGCAAGCCCCTTGGGGAGGGCTGCTTCGGCCAGGTGGTCATG
GCGGAGGCCATCGGCATTGACAAGGACCGGGCCGCCAAGCCTGTCACCGTAGCC
GTGAAGATGCTGAAAGACGATGCCACTGACAAGGACCTGTCGGACCTGGTGTCT
GAGATGGAGATGATGAAGATGATCGGGAAACACAAAAACATCATCAACCTGCTG
GGCGCCTGCACGCAGGGCGGGCCCCTGTACGTGCTGGTGGAGTACGCGGCCAAG
GGTAACCTGCGGGAGTTTCTGCGGGCGCGGCGGCCCCCGGGCCTGGACTACTCCT
TCGACACCTGCAAGCCGCCCGAGGAGCAGCTCACCTTCAAGGACCTGGTGTCCTG
TGCCTACCAGGTGGCCCGGGGCATGGAGTACTTGGCCTCCCAGAAGTGCATCCAC
AGGGACCTGGCTGCCCGCAATGTGCTGGTGACCGAGGACAACGTGATGAAGATC
GCAGACTTCGGGCTGGCCCGGGACGTGCACAACCTCGACTACTACAAGAAGACG
ACCAACGGCCGGCTGCCCGTGAAGTGGATGGCGCCTGAGGCCTTGTTTGACCGA
GTCTACACTCACCAGAGTGACGTCTGGTCCTTTGGGGTCCTGCTCTGGGAGATCT
TCACGCTGGGGGGGCTCCCCGTACCCCGGCATCCCTGTGGAGGAGCTCTTCAAGCT
```

TABLE 6-continued

GCTGAAGGAGGGCCACCGCATGGACAAGCCCGCCAACTGCACACACGACCTGTA
CATGATCATGCGGGAGTGCTGGCATGCCGCGCCCTCCCAGAGGCCCACCTTCAAG
CAGCTGGTGGAGGACCTGGACCGTGTCCTTACCGTGACGTCCACCGACGTGCCAG
GCCCACCCCCAGGTGTTCCCGCGCCTGGGGGCCCACCCCTGTCCACCGGACCTAT
AGTGGACCTGCTCCAGTACAGCCAGAAGGACCTGGATGCAGTGGTAAAGGCGAC
ACAGGAGGAGAACCGGGAGCTGAGGAGCAGGTGTGAGGAGCTCCACGGGAAGA
ACCTGGAACTGGGGAAGATCATGGACAGGTTCGAAGAGGTTGTGTACCAGGCCA
TGGAGGAAGTTCAGAAGCAGAAGGAACTTTCCAAAGCTGAAATCCAGAAAGTTC
TAAAAGAAAAAGACCAACTTACCACAGATCTGAACTCCATGGAGAAGTCCTTCT
CCGACCTCTTCAAGCGTTTTGAGAAACAGAAAGAGGTGATCGAGGGCTACCGCA
AGAACGAAGAGTCACTGAAGAAGTGCGTGGAGGATTACCTGGCAAGGATCACCC
AGGAGGGCCAGAGGTACCAAGCCCTGAAGGCCCACGCGGAGGAGAAGCTGCAG
CTGGCAAACGAGGAGATCGCCCAGGTCCGGAGCAAGGCCCAGGCGGAAGCGTTG
GCCCTCCAGGCCAGCCTGAGGAAGGAGCAGATGCGCATCCAGTCGCTGGAGAAG
ACAGTGGAGCAGAAGACTAAAGAGAACGAGGAGCTGACCAGGATCTGCGACGA
CCTCATCTCCAAGATGGAGAAGATCTGA

FGFR3  
Intron:TACC3  
(4462 base pairs)  
(SEQ ID NO: 21)

>ATGGGCGCCCTGCCTGCGCCCTCGCGCTCTGCGTGGCCGTGGCCATCGTGGCC
GGCGCCTCCTCGGAGTCCTTGGGGACGGAGCAGCGCGTCGTGGGGCGAGCGGCA
GAAGTCCCGGGCCCAGAGCCCGGCCAGCAGGAGCAGTTGGTCTTCGGCAGCGGG
GATGCTGTGGAGCTGAGCTGTCCCCCGCCCGGGGGTGGTCCCATGGGGCCCACTG
TCTGGGTCAAGGATGGCACAGGGCTGGTGCCCTCGGAGCGTGTCCTGGTGGGGC
CCCAGCGGCTGCAGGTGCTGAATGCCTCCCACGAGGACTCCGGGGCCTACAGCT
GCCGGCAGCGGCTCACGCAGCGCGTACTGTGCCACTTCAGTGTGCGGGTGACAG
ACGCTCCATCCTCGGGAGATGACGAAGACGGGGAGGACGAGGCTGAGGACACA
GGTGTGGACACAGGGGCCCCTTACTGGACACGGCCCGAGCGGATGGACAAGAAG
CTGCTGGCCGTGCCGGCCGCCAACACCGTCCGCTTCCGCTGCCCAGCCGCTGGCA
ACCCCACTCCCTCCATCTCCTGGCTGAAGAACGGCAGGGAGTTCCGCGGCGAGC
ACCGCATTGGAGGCATCAAGCTGCGGCATCAGCAGTGGAGCCTGGTCATGGAAA
GCGTGGTGCCCTCGGACCGCGGCAACTACACCTGCGTCGTGGAGAACAAGTTTG
GCAGCATCCGGCAGACGTACACGCTGGACGTGCTGGAGCGCTCCCCGCACCGGC
CCATCCTGCAGGCGGGGCTGCCGGCCAACCAGACGGCGGTGCTGGGCAGCGACG
TGGAGTTCCACTGCAAGGTGTACAGTGACGCACAGCCCCACATCCAGTGGCTCA
AGCACGTGGAGGTGAATGGCAGCAAGGTGGGCCCGGACGGCACACCCTACGTTA
CCGTGCTCAAGACGGCGGGGCGCTAACACCACCGACAAGGAGCTAGAGGTTCTCT
CCTTGCACAACGTCACCTTTGAGGACGCGGGGAGTACACCTGCCTGGCGGGCA
ATTCTATTGGGTTTTCTCATCACTCTGCGTGGCTGGTGGTGCTGCCAGCCGAGGA
GGAGCTGGTGGAGGCTGACGAGGCGGGCAGTGTGTATGCAGGCATCCTCAGCTA
CGGGGTGGGCTTCTTCCTGTTCATCCTGGTGGTGGCGGCTGTGACGCTCTGCCGC
CTGCGCAGCCCCCCCAAGAAAGGCCTGGGCTCCCCCACCGTGCACAAGATCTCCC
GCTTCCCGCTCAAGCGACAGGTGTCCCTGGAGTCCAACGCGTCCATGAGCTCCAA
CACACCACTGGTGCGCATCGCAAGGCTGTCCTCAGGGGAGGGCCCCACGCTGGC
CAATGTCTCCGAGCTCGAGCTGCCTGCCGACCCCAAATGGGAGCTGTCTCGGGCC
CGGCTGACCCTGGGCAAGCCCCTTGGGGAGGGCTGCTTCGGCCAGGTGGTCATG
GCGGAGGCCATCGGCATTGACAAGGACCGGGCCGCCAAGCCTGTCACCGTAGCC
GTGAAGATGCTGAAAGACGATGCCACTGACAAGGACCTGTCGGACCTGGTGTCT
GAGATGGAGATGATGAAGATGATCGGGAAACACAAAAAACATCATCAACCTGCTG
GGCGCCTGCACGCAGGGCGGGCCCCTGTACGTGCTGGTGGAGTACGCGGCCAAG
GGTAACCTGCGGGAGTTTCTGCGGGCGCGGCGGCCCCCCGGGCCTGGACTACTCCT
TCGACACCTGCAAGCCGCCCGAGGAGCAGCTCACCTTCAAGGACCTGGTGTCCTG
TGCCTACCAGGTGGCCCGGGGCATGGAGTACTTGGCCTCCCAGAAGTGCATCCAC
AGGGACCTGGCTGCCCGCAATGTGCTGGTGACCGAGGACAACGTGATGAAGATC
GCAGACTTCGGGCTGGCCCGGGACGTGCACAACCTCGACTACTACAAGAAGACG
ACCAACGGCCGGCTGCCCGTGAAGTGGATGGCGCCTGAGGCCTTGTTTGACCGA
GTCTACACTCACCAGAGTGACGTCTGGTCCTTTGGGGTCCTGCTCTGGGAGATCT
TCACGCTGGGGGGCTCCCCGTACCCCGGCATCCCTGTGGAGGAGCTCTTCAAGCT
GCTGAAGGAGGGCCACCGCATGGACAAGCCCGCCAACTGCACACACGACCTGTA
CATGATCATGCGGGAGTGCTGGCATGCCGCGCCCTCCCAGAGGCCCACCTTCAAG
CAGCTGGTGGAGGACCTGGACCGTGTCCTTACCGTGACGTCCACCGAC
*gtgagtgctggctctggcctggtgccaccgcctatgccctccccctgccgtc*
*cccggccatcctgccccccagagtgctgaggtgtggggcgggccctt*
TCTGGCCCAGGTGCCCTGGCTGACCTGGACTGCTCAAGCTCTTCCCAGAGCCCA
GGAAGTTCTGAGAACCAAATGGTGTCTCCAGGAAAAGTGTCTGGCAGCCCTGAG
CAAGCCGTGGAGGAAAACCTTAGTTCCTATTCCTTAGACAGAAGAGTGACACCC
GCCTCTGAGACCCTAGAAGACCCTTGCAGGACAGAGTCCCAGCACAAAGCGGAG
ACTCCGCACGGAGCCGAGGAAGAATGCAAAGCGGAGACTCCGCACGGAGCCGA
GGAGGAATGCCGGCACGGTGGGGTCTGTGCTCCCGCAGCAGTGGCCACTTCGCC
TCCTGGTGCAATCCCTAAGGAAGCCTGCGGAGGAGCACCCCTGCAGGGTCTGCCT
GGCGAAGCCCTGGGCTGCCCTGCGGGTGTGGGCACCCCCGTGCCAGCAGATGGC
ACTCAGACCCTTACCTGTGCACACACCTCTGCTCCTGAGAGCACAGCCCCAACCA
ACCACCTGGTGGCTGGCAGGGCCATGACCCTGAGTCCTCAGGAAGAAGTGGCTG
CAGGCCAAATGGCCAGCTCCTCGAGGAGCGGACCTGTAAAACTAGAATTTGATG
TATCTGATGGCGCCACCAGCAAAAGGGCACCCCCACCAAGGAGACTGGGAGAGA
GGTCCGGCCTCAAGCCTCCCTTGAGGAAAGCAGCAGTGAGGCAGCAAAAGGCCC
CGCAGGAGGTGGAGGAGGACGACGTAGGAGGCGGAGCAGGAGGACCCCCCC
ATGCCAGCTTCTCGGGGCTCTTACCACCTCGACTGGGACAAAATGGATGACCCAA
ACTTCATCCCGTTCGGAGGTGACACCCAAGTCTGGTTGCAGTGAGGCCCAGCCCC
AGAAAGCCCTGAGACCAGGCTGGGCCAGCCAGCGGCTGAACAGTTGCATGCTGG
GCCTGCCACGGAGGAGCCAGGTCCCTGTCTGAGCCAGCAGCTGCATTCAGCCTCA
GCGGAGGACACGCCTGTGGTGCAGTTGGCAGCCGAGACCCCAACAGCAGAGAGC AAGGAGAGAGCCTTGAACTCTGCCAGCACCTCGCTTCCCACAAGCTGTCCAGGC
AGTGAGCCAGTGCCCACCCATCAGCAGGGGCAGCCTGCCTTGGAGCTGAAAGAG
GAGAGCTTCAGAGACCCCGCTGAGGTTCTAGGCACGGGCGCGGAGGTGGATTAC
CTGGAGCAGTTTGGAACTTCCTCGTTTAAGGAGTCGGCCTTGAGGAAGCAGTCCT
TATACCTCAAGTTCGACCCCCTCCTGAGGGACAGTCCTGGTAGACCAGTGCCCGT
GGCCACCGAGACCAGCAGCATGCACGGTGCAAATGAGACTCCCTCAGGACGTCC
GCGGGAAGCCAAGCTTGTGGAGTTCGATTTCTTGGGAGCACTGGACATTCCTGTG
CCAGGCCCACCCCCAGGTGTTCCCGCGCCTGGGGGCCCACCCCTGTCCACCGGAC
CTATAGTGGACCTGCTCCAGTACAGCCAGAAGGACCTGGATGCAGTGGTAAAGG
CGACACAGGAGGAGAACCGGGAGCTGAGGAGCAGGTGTGAGGAGCTCCACGGG
AAGAACCTGGAACTGGGGAAGATCATGGACAGGTTCGAAGAGGTTGTGTACCAG
GCCATGGAGGAAGTTCAGAAGCAGAAGGAACTTTCCAAAGCTGAAATCCAGAAA
GTTCTAAAAGAAAAAGACCAACTTACCACAGATCTGAACTCCATGGAGAAGTCC
TTCTCCGACCTCTTCAAGCGTTTTGAGAAACAGAAAGAGGTGATCGAGGGCTACC
GCAAGAACGAAGAGTCACTGAAGAAGTGCGTGGAGGATTACCTGGCAAGGATCA
CCCAGGAGGGCCAGAGGTACCAAGCCCTGAAGGCCCACGCGGAGGAGAAGCTG
CAGCTGGCAAACGAGGAGATCGCCCAGGTCCGGAGCAAGGCCCCAGGCGGAAGC
GTTGGCCCTCCAGGCCAGCCTGAGGAAGGAGCAGATGCGCATCCAGTCGCTGGA
GAAGACAGTGGAGCAGAAGACTAAAGAGAACGAGGAGCTGACCAGGATCTGCG
ACGACCTCATCTCCAAGATGGAGAAGATCTGA FGFR3:BAIAP2L1
(3765 base pairs)
(SEQ ID NO: 22)

>ATGGGCGCCCCTGCCTGCGCCCTCGCGCTCTGCGTGGCCGTGGCCATCGTGGCC
GGCGCCTCCTCGGAGTCCTTGGGGACGGGAGCAGCGCGTCGTGGGGCGAGCGGCA
GAAGTCCCGGGCCCAGAGCCCGGCCAGCAGGAGCAGTTGGTCTTCGGCAGCGGG
GATGCTGTGGAGCTGAGCTGTCCCCCGCCCGGGGGTGGTCCCATGGGGCCCACTG
TCTGGGTCAAGGATGGCACAGGGCTGGTGCCCTCGGAGCGTGTCCTGGTGGGGC
CCCAGCGGCTGCAGGTGCTGAATGCCTCCCACGAGGACTCCGGGGCCTACAGCT
GCCGGCAGCGGCTCACGCAGCGCGTACTGTGCCACTTCAGTGTGCGGGTGACAG
ACGCTCCATCCTCGGGAGATGACGAAGACGGGGAGGACGAGGCTGAGGACACA
GGTGTGGACACAGGGGCCCCTTACTGGACACGGCCCGAGCGGATGGACAAGAAG
CTGCTGGCCGTGCCGGCCGCCAACACCGTCCGCTTCCGCTGCCCAGCCGCTGGCA
ACCCCACTCCCTCCATCTCCTGGCTGAAGAACGGCAGGGAGTTCCGCGGCGAGC
ACCGCATTGGAGGCATCAAGCTGCGGCATCAGCAGTGGAGCCTGGTCATGGAAA
GCGTGGTGCCCTCGGACCGCGGCAACTACACCTGCGTCGTGGAGAACAAGTTTG
GCAGCATCCGGCAGACGTACACGCTGGACGTGCTGGAGCGCTCCCCGCACCGGC
CCATCCTGCAGGCGGGGCTGCCGGCCAACCAGACGGCGGTGCTGGGCAGCGACG
TGGAGTTCCACTGCAAGGTGTACAGTGACGCACAGCCCCACATCCAGTGGCTCA
AGCACGTGGAGGTGAATGGCAGCAAGGTGGGCCCGGACGGCACACCCTACGTTA
CCGTGCTCAAGTCCTGGATCAGTGAGAGTGTGGAGGCCGACGTGCGCCTCCGCCT
GGCCAATGTGTCGGAGCGGGACGGGGGCGAGTACCTCTGTCGAGCCACCAATTT
CATAGGCGTGGCCGAGAAGGCCTTTTGGCTGAGCGTTCACGGGCCCCGAGCAGC
CGAGGAGGAGCTGGTGGAGGCTGACGAGGCGGGCAGTGTGTATGCAGGCATCCT
CAGCTACGGGGTGGGCTTCTTCCTGTTCATCCTGGTGGTGGCGGCTGTGACGCTC
TGCCGCCTGCGCAGCCCCCCCAAGAAAGGCCTGGGCTCCCCCACCGTGCACAAG
ATCTCCCGCTTCCCGCTCAAGCGACAGGTGTCCCTGGAGTCCAACGCGTCCATGA
GCTCCAACACACCACTGGTGCGCATCGCAAGGCTGTCCTCAGGGGAGGGCCCCA
CGCTGGCCAATGTCTCCGAGCTCGAGCTGCCTGCCGACCCCAAATGGGAGCTGTC
TCGGGCCCGGCTGACCCTGGGCAAGCCCCTTGGGGAGGGCTGCTTCGGCCAGGT
GGTCATGGCGGAGGCCATCGGCATTGACAAGGACCGGGCCGCCAAGCCTGTCAC
CGTAGCCGTGAAGATGCTGAAAGACGATGCCACTGACAAGGACCTGTCGGACCT
GGTGTCTGAGATGGAGATGATGAAGATGATCGGGAAACACAAAAACATCATCAA
CCTGCTGGGCGCCTGCACGCAGGGCGGGCCCCTGTACGTGCTGGTGGAGTACGC
GGCCAAGGGTAACCTGCGGGAGTTTCTGCGGGCGCGGCGGCCCCCGGGCCTGGA
CTACTCCTTCGACACCTGCAAGCCGCCCGAGGAGCAGCTCACCTTCAAGGACCTG
GTGTCCTGTGCCTACCAGGTGGCCCGGGGCATGGAGTACTTGGCCTCCCAGAAGT
GCATCCACAGGGACCTGGCTGCCCGCAATGTGCTGGTGACCGAGGACAACGTGA
TGAAGATCGCAGACTTCGGGCTGGCCCGGGACGTGCACAACCTCGACTACTACA
AGAAGACGACCAACGGCCGGCTGCCCGTGAAGTGGATGGCGCCTGAGGCCTTGT
TTGACCGAGTCTACACTCACCAGAGTGACGTCTGGTCCTTTGGGGTCCTGCTCTG
GGAGATCTTCACGCTGGGGGGGCTCCCCGTACCCCGGCATCCCTGTGGAGGAGCTC
TTCAAGCTGCTGAAGGAGGGCCACCGCATGGACAAGCCCGCCAACTGCACACAC
GACCTGTACATGATCATGCGGGAGTGCTGGCATGCCGCGCCCTCCCAGAGGCCC
ACCTTCAAGCAGCTGGTGGAGGACCTGGACCGTGTCCTTACCGTGACGTCCACCG
ACAATGTTATGGAACAGTTCAATCCTGGGCTGCGAAATTTAATAAACCTGGGGA
AAAATTATGAGAAAGCTGTAAACGCTATGATCCTGGCAGGAAAAGCCTACTACG
ATGGAGTGGCCAAGATCGGTGAGATTGCCACTGGGTCCCCCGTGTCAACTGAACT
GGGACATGTCCTCATAGAGATTTCAAGTACCCACAAGAAACTCAACGAGAGTCT
TGATGAAAATTTTAAAAAATTCCACAAAGAGATTATCCATGAGCTGGAGAAGAA
GATAGAACTTGACGTGAAATATATGAACGCAACTCTAAAAAGATACCAAACAGA
ACACAAGAATAAATTAGAGTCTTTGGAGAAATCCCAAGCTGAGTTGAAGAAGAT
CAGAAGGAAAAGCCAAGGAAGCCGAAACGCACTCAAATATGAACACAAAGAAA
TTGAGTATGTGGAGACCGTTACTTCTCGTCAGAGTGAAATCCAGAAATTCATTGC
AGATGGTTGCAAAGAGGCTCTGCTTGAAGAGAAGAGGGCGCTTCTGCTTTCTGGTT
GATAAGCACTGTGGCTTTGCAAACCACATACATTATTATCACTTACAGTCTGCAG
AACTACTGAATTCCAAGCTGCCTCGGTGGCCAGGAGACCTGTGTTGATGCCATCAA
AGTGCCAGAGAAAATCATGAATATGATCGAAGAAATAAAGACCCCAGCCTCTAC
CCCCGTGTCTGGAACTCCTCAGGCTTCACCCATGATCGAGAGAAGCAATGTGGTT
AGGAAAGATTACGACACCCTTTCTAAATGCTCACCAAAGATGCCCCCCGCTCCTT
CAGGCAGAGCATATACCAGTCCCTTGATCGATATGTTTAATAACCCAGCCACGGC
TGCCCCGAATTCACAAAGGGTAAATAATTCAACAGGTACTTCCGAAGATCCCAGT

TABLE 6-continued

```
TTACAGCGATCAGTTTCGGTTGCAACGGGACTGAACATGATGAAGAAGCAGAAA
GTGAAGACCATCTTCCCGCACACTGCGGGCTCCAACAAGACCTTACTCAGCTTTG
CACAGGGAGATGTCATCACGCTGCTCATCCCCGAGGAGAAGGATGGCTGGCTCT
ATGGAGAACACGACGTGTCCAAGGCGAGGGGTTGGTTCCCGTCGTCGTACACGA
AGTTGCTGGAAGAAAATGAGACAGAAGCAGTGACCGTGCCCACGCCAAGCCCCA
CACCAGTGAGAAGCATCAGCACCGTGAACTTGTCTGAGAATAGCAGTGTTGTCAT
CCCCCCACCCGACTACTTGGAATGCTTGTCCATGGGGGCAGCTGCCGACAGGAG
AGCAGATTCGGCCAGGACGACATCCACCTTTAAGGCCCCAGCGTCCAAGCCCGA
GACCGCGGCTCCTAACGATGCCAACGGGACTGCAAAGCCGCCTTTTCTCAGCGG
AGAAAACCCCTTTGCCACTGTGAAACTCCGCCCGACTGTGACGAATGATCGCTCG
GCACCCATCATTCGATGA
```

FGFR2:BICC1              >ATGGTCAGCTGGGGTCGTTTCATCTGCCTGGTCGTGGTCACCATGGCAACCTTGT
(4989 base pairs)        CCCTGGCCCGGCCCTCCTTCAGTTTAGTTGAGGATACCACATTAGAGCCAGAAGA
(SEQ ID NO: 23)          GCCACCAACCAAATACCAAATCTCTCAACCAGAAGTGTACGTGGCTGCGCCAGG
```
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATGA
ATACGGGTCCATCAATCACACGTACCACCTGGATGTTGTGGAGCGATCGCCTCAC
CGGCCCATCCTCCAAGCCGGACTGCCGGCAAATGCCTCCACAGTGGTCGGAGGA
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGATCATGGAGGAAACAAATACGCAGATTGCTTGGCCATCAAAA
CTGAAGATCGGAGCCAAATCCAAGAAAGATCCCCATATTAAGGTTTCTGGAAAG
AAAGAAGATGTTAAAGAAGCCAAGGAAATGATCATGTCTGTCTTAGACACAAAA
AGCAATCGAGTCACACTGAAGATGGATGTTTCACATACAGAACATTCACATGTA
ATCGGCAAAGGTGGCAACAATATTAAAAAAGTGATGGAAGAAACCGGATGCCAT
ATCCACTTTCCAGATTCCAACAGGAATAACCAAGCAGAAAAAAGCAACCAGGTA
TCTATAGCGGGACAACCAGCAGGAGTAGAATCTGCCCGAGTTAGAATTCGGGAG
CTGCTTCCTTTGGTGCTGATGTTTGAGCTACCAATTGCTGGAATTCTTCAACCGGT
TCCTGATCCTAATTCCCCCTCTATTCAGCATATATCACAAACGTACAATATTTCAG
TATCATTTAAACAGCGTTCCCGAATGTATGGTGCTACTGTCATAGTACGAGGGTC
TCAGAATAACACTAGTGCTGTGAAGGAAGGAACTGCCATGCTGTTAGAACATCTT
GCTGGGAGCTTAGCATCAGCTATTCCTGTGAGCACACAACTAGATATTGCAGCTC
AACATCATCTCTTTATGATGGGTCGAAATGGGAGCAACATCAAACATATCATGCA
GAGAACAGGTGCTCAGATCCACTTTCCTGATCCCAGTAATCCACAAAAGAAATCT
ACCGTCTACCTCCAGGGCACCATTGAGTCTGTCGTCTTGCAAGGCAATATCTCA
TGGGTTGTCTTCCTCTTGTGTTGATGTTTGATATGAAGGAAGAAATTGAAGTAGA
TCCACAATTCATTGCGCAGTTGATGGAACAGCTTGATGTCTTCATCAGTATTAAA
CCAAAGCCCAAACAGCCAAGCAAGTCTGTGATTGTGAAAAGTGTTGAGCGAAAT
GCCTTAAATATGTATGAAGCAAGGAAATGTCTCCTCGGACTTGAAAGCAGTGGG
GTTACCATAGCAACCAGTCCATCCCCAGCATCCTGCCCTGCCGGCCTGGCATGTC
CCAGCCTGGATATCTTAGCTTCAGCAGGCCTTGGACTCACTGACTAGGTCTTTT
GGGACCCACCACCTTATCTCTGAACACTTCAACAACCCCAAACTCACTCTTGAAT
GCTCTTAATAGCTCAGTCAGTCCTTTGCAAAGTCCAAGTTCTGGTACACCCAGCC
CCACATTATGGGCACCCCCACTTGCTAATACTTCAAGTGCCACAGGTTTTTCTGCT
ATACCACACCTTATGATTCCATCTACTGCCCAAGCCACATTAACTAATATTTTGTT
GTCTGGAGTGCCCACCTATGGGCACACAGCTCCATCTCCCCCTCCTGGCTTGACT
```

TABLE 6-continued

```
CCTGTTGATGTCCATATCAACAGTATGCAGACCGAAGGCAAAAAAATCTCTGCTG
CTTTAAATGGACATGCACAGTCTCCAGATATAAAATATGGTGCAATATCCACTTC
ATCACTTGGAGAAAAAGTGCTGAGTGCAAATCACGGGGATCCGTCCATCCAGAC
AAGTGGGTCTGAGCAGACATCTCCCAAATCAAGCCCCACTGAAGGTTGTAATGA
TGCTTTTGTTGAAGTAGGCATGCCTCGAAGTCCTTCCCATTCTGGGAATGCTGGT
GACTTGAAACAGATGATGTGTCCCTCCAAGGTTTCCTGTGCCAAAAGGCAGACA
GTGGAACTATTGCAAGGCACGAAAAACTCACACTTACACAGCACTGACAGGTTG
CTCTCAGACCCTGAACTGAGTGCTACCGAAAGCCCTTTGGCTGACAAGAAGGCTC
CAGGGAGTGAGCGCGCTGCAGAGAGGGCAGCAGCTGCCCAGCAAAACTCCGAA
AGGGCCCACCTTGCTCCACGGTCATCATATGTCAACATGCAGGCATTTGACTATG
AACAGAAGAAGCTATTAGCCACCAAAGCTATGTTAAAGAAACCAGTGGTGACGG
AGGTCAGAACGCCCACAAATACCTGGAGTGGCCTGGGTTTTTCTAAATCCATGCC
AGCTGAAACTATCAAGGAGTTGAGAAGGGCCAATCATGTGTCCTATAAGCCCAC
AATGACAACCACTTATGAGGGCTCATCCATGTCCCTTTCACGGTCCAACAGTCGT
GAGCACTTGGGAGGTGGAAGCGAATCTGATAACTGGAGAGACCGAAATGGAATT
GGACCTGGAAGTCATAGTGAATTTGCAGCTTCTATTGGCAGCCCTAAGCGTAAAC
AAAACAAATCAACGGAACACTATCTCAGCAGTAGCAATTACATGGACTGCATTT
CCTCGCTGACAGGAAGCAATGGCTGTAACTTAAATAGCTCTTTCAAAGGTTCTGA
CCTCCCTGAGCTCTTCAGCAAACTGGGCCTGGGCAAATACACAGATGTTTTCCAG
CAACAAGAGATCGATCTTCAGACATTCCTCACTCTCACAGATCAGGATCTGAAGG
AGCTGGGAATAACTACTTTTGGTGCCAGGAGGAAAATGCTGCTTGCAATTTCAGA
ACTAAATAAAAACCGAAGAAAGCTTTTTGAATCGCCAAATGCACGCACCTCTTTC
CTGGAAGGTGGAGCGAGTGGAAGGCTACCCCGTCAGTATCACTCAGACATTGCT
AGTGTCAGTGGCCGCTGGTAG
```

FGFR2:AFF3
(5109 base pairs)
(SEQ ID NO: 24)

```
>ATGGTCAGCTGGGGTCGTTTCATCTGCCTGGTCGTGGTCACCATGGCAACCTTGT
CCCTGGCCCGGCCCTCCTTCAGTTTAGTTGAGGATACCACATTAGAGCCAGAAGA
GCCACCAACCAAATACCAAATCTCTCAACCAGAAGTGTACGTGGCTGCGCCAGG
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATAGA
ATACGGGTCCATCAATCACACGTACCACCTGGATGTTGTGGAGCGATCGCCTCAC
CGGCCCATCCTCCAAGCCGGACTGCCGGCAAATGCCTCCACAGTGGTCGGAGGA
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGGAGTAGATCTGGAGAAACCAACAGCTGTGTTGAAGAAATA
ATCCGGGAGATGACCTGGCTTCCACCCACTTTCTGCTATTCAAGCACCTGGCAAAG
TGGAACCAACCAAATTTCCATTTCCAAATAAGGACTCTCAGCTTGTATCCTCTGG
ACACAATAATCCAAAGAAAGGTGATGCAGAGCCAGAGAGTCCAGACAGTGGCA
CATCGAATACATCAATGCTGGAAGATGACCTTAAGCTAAGCAGTGATGAAGAGG
AGAATGAACAGCAGGCAGCTCAGAGAACGGCTCTCCGCGCTCTCTCTGACAGCG
CCGTGGTCCAGCAGCCCAACTGCAGAACCTCGGTGCCTTCCAGCAAGGGCAGCA
GCAGCAGCAGCAGCAGCGGCAGCAGCAGCTCCTCCAGCGACTCAGAGAGCAGCT
CCGGATCTGACTCGGAGACCGAGAGCAGCTCCAGCGAGAGTGAGGGCAGCAAGC
CCCCCCACTTCTCCAGCCCCGAGGCTGAACCGGCATCCTCTAACAAGTGGCAGCT
GGATAAATGGCTAAACAAAGTTAATCCCCACAAGCCTCCTATTCTGATCCAAAAT
GAAAGCCACGGGTCAGAGAGCAATCAGTACTACAACCCCGGTGAAAGAGGACGTC
CAGGACTGTGGGAAAGTCCCCGACGTTTGCCAGCCCAGCCTGAGAGAGAAGGAG
```

TABLE 6-continued

ATCAAGAGCACTTGCAAGGAGGAGCAAAGGCCAAGGACAGCCAACAAGGCCCC
TGGGAGTAAAGGCGTGAAGCAGAAGTCCCCGCCCGCGGCCGTGGCCGTGGCGGT
GAGCGCAGCCGCCCCGCCACCCGCAGTGCCCTGTGCGCCCGCGGAGAACGCGCC
CGCGCCTGCCCGGAGGTCCGCGGGCAAGAAGCCCACCAGGCGCACCGAGAGGAC
CTCAGCCGGGGACGGCGCCAACTGCCACCGGCCCGAGGAGCCCGCGGCCGCGGA
CGCGCTGGGGACGAGCGTGGTGGTCCCCCCGGAGCCCACCAAAACCAGGCCCTG
TGGCAACAACAGAGCGAGCCACCGCAAGGAGCTGCGCTCCTCCGTGACCTGCGA
GAAGCGCCGCACGCGGGGGCTAAGCAGGATCGTCCCCAAATCCAAGGAGTTCAT
TGAGACAGAGTCGTCATCTTCATCCTCCTCCTCGGACTCCGACCTGGAGTCCGAG
CAGGAGGAGTACCCTCTGTCCAAAGCACAGACCGTGGCTGCCTCTGCCTCCTCCG
GGAATGATCAGAGGCTGAAGGAGGCCGCTGCCAACGGGGGCAGTGGTCCTAGGG
CCCCTGTAGGCTCCATCAACGCCAGGACCACCAGTGACATCGCCAAGGAGCTGG
AGGAGCAGTTCTACACACTGGTCCCCTTTGGCCGGAACGAACTTCTCTCCCCTCT
AAAGGACAGTGATGAGATCAGGTCTCTCTGGGTCAAAATCGACCTGACCCTCCTG
TCCAGGATCCCAGAACACCTGCCCCAGGAGCCAGGGGTATTGAGCGCCCCTGCC
ACCAAGGACTCTGAGAGCGCACCGCCCAGCCACACCTCGGACACACCTGCAGAA
AAGGCTTTGCCAAAATCCAAGAGGAAACGCAAGTGTGACAACGAAGACGACTAC
AGGGAGATCAAGAAGTCCCAGGGAGAGAAAGACAGCTCTTCAAGACTGGCCACC
TCCACCAGTAATACTTTGTCTGCAAACCACTGCAACATGAACATCAACAGTGTGG
CAATACCAATAAATAAAAATGAAAAAATGCTTCGGTCGCCCATCTCACCCCTCTC
TGATGCATCTAAACACAAATACACCAGCGAGGACTTAACTTCTTCCAGCCGACCT
AATGGCAACAGTTTGTTTACTTCAGCCTCTTCCAGCAAAAAGCCTAAGGCCGACA
GCCAGCTGCAGCCTCACGGCGGAGACCTCACGAAAGCAGCTCACAACAATTCTG
AAAACATTCCCCTCCACAAGTCACGGCCGCAGACGAAGCCGTGGTCTCCAGGCT
CCAACGGCCACAGGGACTGCAAGAGGCAGAAACTTGTCTTCGATGATATGCCTC
GCAGTGCCGATTATTTTATGCAAGAAGCTAAACGAATGAAGCATAAAGCAGATG
CAATGGTGGAAAGTTTGGAAAGGCTTTGAACTATGCTGAAGCAGCATTGTCGTT
TATCGAGTGTGGAAATGCAATGGAACAAGGCCCCATGGAATCCAAATCTCCTTAT
ACGATGTATTCAGAAACAGTAGAGCTCATCAGGTATGCTATGAGACTAAAAACC
CACTCAGGCCCCAATGCCACACCAGAAGACAAACAACTGGCTGCATTATGTTAC
CGATGCCTGGCCCTCCTGTACTGGCGGATGTTTCGACTCAAAAGGGACCACGCTG
TAAAGTATTCAAAAGCACTAATCGACTATTTCAAGAACTCATCTAAAGCCGCCCA
AGCCCCATCTCCGTGGGGGGCCAGTGGAAAGAGCACTGGAACCCCATCCCCCAT
GTCTCCCAACCCCTCTCCCGCCAGCTCCGTGGGGTCTCAGGGCAGCCTCTCCAAC
GCCAGCGCCCTGTCCCCGTCGACCATCGTCAGCATCCCACAGCGCATCCACCAGA
TGGCGGCCAACCACGTCAGCATCACCAACAGCATCCTGCACAGCTACGACTACT
GGGAGATGGCCGACAACCTGGCCAAGGAAAACCGAGAATTCTTCAACGACCTGG
ATCTGCTCATGGGGCCGGTCACCCTGCACAGCAGCATGGAGCACCTGGTCCAGTA
CTCCCAACAGGGCCTGCACTGGCTGCGGAACAGCGCCCACCTGTCATAG

FGFR2:CASP7  >ATGGTCAGCTGGGGTCGTTTCATCTGCCTGGTCGTGGTCACCATGGCAACCTTGT
(3213 base pairs)  CCCTGGCCCGGCCCTCCTTCAGTTTAGTTGAGGATACCACCATTAGAGCCAGAAGA
(SEQ ID NO: 25)  GCCACCAACCAAATACCAAATCTCTCAACCAGAAGTGTACGTGGCTGCGCCAGG
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATGA
ATACGGGTCCATCAATCACACGTACCACCTGGATGTTGTGGAGCGATCGCCTCAC
CGGCCCATCCTCCAAGCCGGACTGCCGGCAAATGCCTCCACAGTGGTCGGAGGA
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA TABLE 6-continued

```
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGATGGCAGATGATCAGGGCTGTATTGAAGAGCAGGGGGTTGAG
GATTCAGCAAATGAAGATTCAGTGGATGCTAAGCCAGACCAGGTCCTCGTTTGTAC
CGTCCCTCTTCAGTAAGAAGAAGAAAAATGTCACCATGCGATCCATCAAGACCA
CCCGGGACCGAGTGCCTACATATCAGTACAACATGAATTTTGAAAAGCTGGGCA
AATGCATCATAATAAACAACAAGAACTTTGATAAAGTGACAGGTATGGGCGTTC
GAAACGGAACAGACAAAGATGCCGAGGCGCTCTTCAAGTGCTTCCGAAGCCTGG
GTTTTGACGTGATTGTCTATAATGACTGCTCTTGTGCCAAGATGCAAGATCTGCTT
AAAAAAGCTTCTGAAGAGGACCATACAAATGCCGCCTGCTTCGCCTGCATCCTCT
TAAGCCATGGAGAAGAAAATGTAATTTATGGGAAAGATGGTGTCACACCAATAA
AGGATTTGACAGCCCACTTTAGGGGGGATAGATGCAAAACCCTTTTAGAGAAAC
CCAAACTCTTCTTCATTCAGGCTTGCCGAGGGACCGAGCTTGATGATGGCATCCA
GGCCGACTCGGGGCCCATCAATGACACAGATGCTAATCCTCGATACAAGATCCC
AGTGGAAGCTGACTTCCTCTTCGCCTATTCCACGGTTCCAGGCTATTACTCGTGG
AGGAGCCCAGGAAGAGGCTCCTGGTTTGTGCAAGCCCTCTGCTCCATCCTGGAGG
AGCACGGAAAAGACCTGGAAATCATGCAGATCCTCACCAGGGTGAATGACAGAG
TTGCCAGGCACTTTGAGTCTCAGTCTGATGACCCACACTTCCATGAGAAGAAGCA
GATCCCCTGTGTGGTCTCCATGCTCACCAAGGAACTCTACTTCAGTCAATAG
```

FGFR2:CCDC6
(3423 base pairs)
(SEQ ID NO: 26)

```
>ATGGTCAGCTGGGGTCGTTTCATCTGCCTGGTCGTGGTCACCATGGCAACCTTGT
CCCTGGCCCGGCCCTCCTTCAGTTTAGTTGAGGATACCACATTAGAGCCAGAAGA
GCCACCAACCAAATACCAAATCTCTCAACCAGAAGTGTACGTGGCTGCGCCAGG
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATGA
ATACGGGTCCATCAATCACACGTACCACCTGGATGTTGTGGAGCGATCGCCTCAC
CGGCCCATCCTCCAAGCCGGACTGCCGGCAAATGCCTCCACAGTGGTCGGAGGA
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGCAAGCCAGGGCTGAGCAGGAAGAAGAATTCATTAGTAACACT
TTATTCAAGAAAATTCAGGCTTTGCAGAAGGAGAAAGAAACCCTTGCTGTAAATT
ATGAGAAAGAAGAAGAATTCCTCACTAATGAGCTCTCCAGAAAATTGATGCAGT
TGCAGCATGAGAAAGCCGAACTAGAACAGCATCTTGAACAAGAGCAGGAATTTC
AGGTCAACAAACTGATGAAGAAAATTAAAAAAACTGGAGAATGACACCATTTCTA
AGCAACTTACATTAGAACAGTTGAGACGGGAGAAGATTGACCTTGAAAATACAT
TGGAACAAGAACAAGAAGCACTAGTTAATCGCCTCTGGAAAAGGATGGATAAGC
TTGAAGCTGAAAAGCGAATCCTGCAGGAAAAATTAGACCAGCCCGTCTCTGCTC
CACCATCGCCTAGAGATATCTCCATGGAGATTGATTCTCCAGAAAATATGATGCG
TCACATCAGGTTTTTAAAGAATGAAGTGGAACGGCTGAAGAAGCAACTGAGAGC
TGCTCAGTTACAGCATTCAGAGAAAATGGCACAGTATCTGGAGGAGGAACGTCA
CATGAGAGAAGAGAACTTGAGGCTCCAGAGGAAGCTGCAGAGGGAGATGGAGA
GAAGAGAAGCCCTCTGTCGACAGCTCTCCGAGAGTGAGTCCAGCTTAGAAATGG
ACGACGAAAGGTATTTTAATGAGATGTCTGCACAAGGATTAAGACCTCGCACTGT
GTCCAGCCCGATCCCTTACACACACCTTCTCCGAGTTCAAGCAGGCCTATATCACCT
GGTCTATCATATGCAAGTCACACGGTTGGTTTCACGCCACCAACTTCACTGACTA
GAGCTGGAATGTCTTATTACAATTCCCCGGGTCTTCACGTGCAGCACATGGGAAC
ATCCCATGGTATCACAAGGCCTTCACCACGGAGAAGCAACAGTCCTGACAAATT
```

TABLE 6-continued

```
CAAACGGCCCACGCCGCCTCCATCTCCCAACACACAGACCCCAGTCCAGCCACCT
CCGCCTCCACCTCCGCCACCCATGCAGCCCACGGTCCCCTCAGCAGCCACCTCGC
AGCCTACTCCTTCGCAACATTCGGCGCACCCCTCCTCCCAGCCTTAA
```

FGFR2:OFD1
(5229 base pairs)
(SEQ ID NO: 27)

```
>ATGGTCAGCTGGGGTCGTTTCATCTGCCTGGTCGTGGTCACCATGGCAACCTTGT
CCCTGGCCCGGCCCTCCTTCAGTTTAGTTGAGGATACCACATTAGAGCCAGAAGA
GCCACCAACCAAATACCAAATCTCTCAACCAGAAGTGTACGTGGCTGCGCCAGG
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATGA
ATACGGGTCCATCAATCACACGTACCACCTGGATGTTGTGGAGCGATCGCCTCAC
CGGCCCATCCTCCAAGCCGGACTGCCGGCAAATGCCTCCACAGTGGTCGGAGGA
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACCTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGACACAACTTCGAAACCAGCTAATTCATGAGTTGATGCACCCT
GTATTGAGTGGAGAACTGCAGCCTCGGTCCATTTCAGTAGAAGGGAGCTCCCTCT
TAATAGGCGCCTCTAACTCTTTAGTGGCAGATCACTTACAAAGATGTGGCTATGA
ATATTCACTTTCTGTTTTCTTTCCAGAAAGTGGTTTGGCAAAAGAAAAGGTATTTA
CTATGCAGGATCTATTACAACTCATTAAAATCAACCCTACTTCCAGTCTCTACAA
ATCACTGGTTTCAGGATCTGATAAAGAAAATCAAAAAGGTTTTCTTATGCATTTT
TTAAAAGAATTGGCAGAATATCATCAAGCTAAAGAGAGTTGTAATATGGAAACT
CAGACAAGTTCGACATTTAACAGAGATTCTCTGGCTGAGAAGCTTCAGCTTATTG
ATGATCAGTTTGCAGATGCTTACCCTCAGCGTATCAAGTTCGAATCTTTAGAAAT
AAAGCTAAATGAGTATAAGAGAGAAATAGAAGAGCAACTTCGGGCAGAAATGT
GTCAAAAGTTGAAGTTTTTTAAAGATACCGAGATAGCAAAAATTAAAATGGAAG
CAAAAAAAAAGTATGAAAAGGAGTTAACCATGTTCCAGAATGATTTTGAAAAAG
CTTGTCAAGCAAAATCTGAAGCTCTCGTTCTTCGGGAAAAGAGTACCCTTGAAAG
AATTCACAAGCACCAAGAGATTGAAACAAAAGAAATTTATGCTCAAAGGCAACT
TTTACTAAAAGATATGGATTTGCTAAGAGGAAGAGAAGCAGAGCTGAAGCAAAG
AGTTGAAGCTTTTGAATTGAACCAGAAGCTCCAGGAAGAAAAACATAAAAGCAT
AACTGAGGCACTTAGGAGACAGGAGCAGAATATAAAGAGTTTTGAGGAGACCTA
TGACCGAAAGCTCAAGAATGAACTTCTAAAGTATCAACTTGAACTGAAGGATGA
CTACATCATTAGAACTAATCGACTGATTGAAGATGAAAGGAAGAATAAAGAAA
AGCTGTTCATTTGCAAGAGGAGCTCATAGCTATTAATTCAAAAAAGGAGGAACT
CAATCAATCTGTAAATCGTGTGAAAGAACTTGAGCTTGAATTAGAGTCTGTCAAA
GCCCAGTCTTTGGCAATAACAAAACAAAACCATATGCTGAATGAAAAGGTTAAA
GAGATGAGTGATTATTCACTACTAAAGAAGAGAAACTGGAGCTTCTGGCACAA
AATAAATTACTTAAACAACAACTGGAAGAGAGTAGAAATGAAAACCTGCGTCTC
CTAAACCGCCTAGCTCAGCCGGCTCCTGAACTTGCAGTCTTTCAGAAAGAACTAC
GGAAAGCCGAAAAGGCTATAGTGGTTGAGCATGAGGAGTTCGAAAGCTGCAGGC
AAGCTCTGCACAAACAACTGCAAGACGAAATTGAGCATTCTGCACAGCTGAAGG
CCCAGATTCTAGGTTACAAAGCTTCTGTAAAGAGTTTAACTACTCAGGTTGCCGA
TTTAAAATTGCAACTGAAGCAAACTCAGACAGCCCCTAGAGAATGAAGTGTACTG
CAATCCAAAGCAGTCTGTGATCGATCGTTCTGTCAATGGATTAATAAATGGCAAT
GTGGCGCCTTGCAATGGTGAGATAAGTGGGGATTTCTTGAACAATCCTTTTAAAC
AGGAAAACGTTCTAGCACGTATGGTTGCATCAAGGATCACAAATTATCCAACTGC
ATGGGTGGAGGGTAGTTCCCCTGATTCTGACCTTGAGTTTGTAGCCAATACTAAG
GCAAGGGTCAAAGAGCTTCAGCAAGAGGCCGAACGCTTGGAAAAAGGCTTTCAGA
```

TABLE 6-continued

```
AGTTACCATCGGAGAGTCATTAAAAACTCTGCCAAAAGCCCACTAGCAGCAAAG
AGCCCACCATCTCTGCACTTGCTGGAAGCCTTCAAAAACATTACTTCCAGTTCCC
CGGAAAGACATATTTTTGGAGAGGACAGAGTTGTCTCTGAGCAGCCTCAAGTGG
GCACACTTGAAGAAAGGAATGACGTCGTGGAAGCACTGACAGGCAGTGCAGCCT
CGAGGCTCCGCGGGGGCACTTCCTCCAGACGCCTCTCTTCCACACCCCTTCCAAA
AGCAAAAAGAAGCCTCGAAAGTGAAATGTATCTGGAAGGTCTGGGCAGATCACA
CATTGCTTCCCCCAGTCCTTGTCCTGACAGAATGCCCCTACCATCACCCACTGAGT
CTAGGCACAGCCTCTCCATCCCTCCTGTCTCCAGCCCTCCGGAGCAGAAAGTGGG
TCTTTATCGAAGACAAACTGAACTTCAAGACAAAAGTGAATTTTCAGATGTGGAC
AAGCTAGCTTTTAAGGATAATGAGGAGTTTGAATCATCTTTTGAATCTGCAGGGA
ACATGCCAAGGCAGTTGGAAATGGGCGGGCTTTCTCCTGCCGGGGATATGTCTCA
TGTGGACGCTGCTGCAGCTGCTGTGCCCCTCTCATATCAGCACCCAAGTGTAGAT
CAGAAACAAATTGAAGAACAAAAGGAAGAAGAAAAAATACGGGAACAGCAAGT
GAAAGAACGAAGGCAGAGAGAAGAAAGAAGGCAGAGTAACCTACAAGAAGTTT
TAGAAAGGGAACGAAGAGAACTAGAAAAACTGTATCAGGAAAGGAAGATGATT
GAAGAATCACTGAAGATTAAAATAAAAAAGGAATTAGAAATGGAAAATGAATT
AGAAATGAGTAATCAAGAAATAAAAGACAAATCTGCTCACAGTGAAAATCCTTT
AGAGAAATACATGAAAATCATCCAGCAGGAGCAAGACCAGGAGTCGGCAGATA
AGAGCTCAAAAAGATGGTCCAAGAAGGCTCCCTAGTGGACACGCTGCAATCTA
GTGACAAAGTCGAAAGTTTAACAGGCTTTTCTCATGAAGAACTAGACGACTCTTG
GTAA
```

The invention claimed is:

1. A method of treating cancer in a patient comprising: administering to the patient a pharmaceutically effective amount of an antibody that blocks the interaction between PD-1 and PD-L1;

monitoring the efficacy of the antibody; and if the antibody is not efficacious, evaluating a biological sample from the patient for a presence of one or more FGFR variants, wherein the one or more FGFR variants comprise an FGFR mutation, and wherein the FGFR mutation is FGFR3 G370C; and
  administering to the patient a pharmaceutically effective amount of an FGFR inhibitor if the one or more FGFR variants are present in the sample, wherein the FGFR inhibitor is the compound of formula (I):

(I)

or a pharmaceutically acceptable salt thereof.

2. The method of claim 1, wherein the evaluating step further comprises measuring an expression level of PD-L1 in a biological sample and wherein the second administering step comprises administering the FGFR inhibitor if:
  the biological sample has a PD-L1 expression corresponding to an H-score of about 0 to about 99; or
  the biological sample has a PD-L1 expression level that is lower than a reference PD-L1 expression level.

3. The method of claim 1, wherein the biological sample is blood, lymph fluid, bone marrow, a solid tumor sample, or any combination thereof.

4. The method of claim 1, wherein the cancer is lung cancer, bladder cancer, gastric cancer, breast cancer, ovarian cancer, head and neck cancer, esophageal cancer, glioblastoma, or any combination thereof.

5. The method of claim 4, wherein the cancer is bladder cancer.

6. The method of claim 1, wherein the one or more FGFR variants further comprise an FGFR fusion gene.

7. The method of claim 1, wherein the one or more FGFR variants comprise at least one additional FGFR mutation, which is FGFR3 R248C.

8. The method of claim 1, wherein the one or more FGFR variants comprise at least one additional FGFR mutation, which is FGFR3 S249C.

9. The method of claim 1, wherein the one or more FGFR variants comprise at least one additional FGFR mutation, which is FGFR3 Y373C.

10. The method of claim 1, wherein the antibody that blocks an interaction between PD-1 and PD-L1 is an anti-PD-1 antibody, an anti-PD-L1 antibody, or a combination thereof.

11. The method of claim 2, wherein the cancer is lung cancer, bladder cancer, gastric cancer, breast cancer, ovarian cancer, head and neck cancer, esophageal cancer, glioblastoma, or any combination thereof.

12. The method of claim 11, wherein the cancer is bladder cancer.

13. The method of claim 2, wherein the one or more FGFR variants further comprise an FGFR fusion gene.

14. The method of claim 2, wherein the one or more FGFR variants comprise at least one additional FGFR mutation, which is FGFR3 R248C.

15. The method of claim 2, wherein the one or more FGFR variants comprise at least one additional FGFR mutation, which is FGFR3 S249C.

16. The method of claim 2, wherein the one or more FGFR variants comprise at least one additional FGFR mutation, which is FGFR3 Y373C.

17. The method of claim 2, wherein the antibody that blocks an interaction between PD-1 and PD-L1 is an anti-PD-1 antibody, an anti-PD-L1 antibody, or a combination thereof.

18. The method of claim 3, wherein the cancer is lung cancer, bladder cancer, gastric cancer, breast cancer, ovarian cancer, head and neck cancer, esophageal cancer, glioblastoma, or any combination thereof.

19. The method of claim 18, wherein the cancer is bladder cancer.

20. The method of claim 3, wherein the one or more FGFR variants further comprise an FGFR fusion gene.

21. The method of claim 3, wherein the one or more FGFR variants comprise at least one additional FGFR mutation, which is FGFR3 R248C.

22. The method of claim 3, wherein the one or more FGFR variants comprise at least one additional FGFR mutation, which is FGFR3 S249C.

23. The method of claim 3, wherein the one or more FGFR variants comprise at least one additional FGFR mutation, which is FGFR3 Y373C.

24. The method of claim 3, wherein the antibody that blocks an interaction between PD-1 and PD-L1 is an anti-PD-1 antibody, an anti-PD-L1 antibody, or a combination thereof.

25. The method of claim 1, wherein the biological sample:
  has a PD-L1 expression corresponding to an H-score of less than 20; or
  has a PD-L1 expression level that is lower than a reference PD-L1 expression level.

26. The method of claim 25, where the biological sample has a PD-L1 expression corresponding to an H-score of less than 20.

27. The method of claim 1, wherein the FGFR inhibitor is the compound of formula (I):

(I)

28. The method of claim 27, wherein the cancer is lung cancer, bladder cancer, gastric cancer, breast cancer, ovarian cancer, head and neck cancer, esophageal cancer, glioblastoma, or any combination thereof.

29. The method of claim 28, wherein the cancer is bladder cancer.

30. The method of claim 29, wherein the one or more FGFR variants further comprise an FGFR fusion gene.

31. The method of claim 29, wherein the one or more FGFR variants comprise at least one additional FGFR mutation, which is FGFR3 R248C.

32. The method of claim 29, wherein the one or more FGFR variants comprise at least one additional FGFR mutation, which is FGFR3 S249C.

33. The method of claim 29, wherein the one or more FGFR variants comprise at least one additional FGFR mutation, which is FGFR3 Y373C.

34. The method of claim 29, wherein the antibody that blocks an interaction between PD-1 and PD-L1 is an anti-PD-1 antibody, an anti-PD-L1 antibody, or a combination thereof.

35. The method of claim 29, wherein the biological sample is a solid tumor sample.

36. The method of claim 3, wherein the biological sample is a solid tumor sample.

\* \* \* \* \*